US012599495B2

(12) United States Patent
Newton et al.

(10) Patent No.: US 12,599,495 B2
(45) Date of Patent: Apr. 14, 2026

(54) MALE EXTERNAL CATHETER WITH ATTACHMENT INTERFACE CONFIGURED TO BIAS AGAINST PENIS

(71) Applicant: PureWick Corporation, El Cajon, CA (US)

(72) Inventors: Camille Rose Newton, Bonsall, CA (US); Raymond John Newton, Bonsall, CA (US); Benjamin Jackson, Statham, GA (US)

(73) Assignee: PUREWICK CORPORATION, Covington, GA (US)

( * ) Notice: Subject to any disclaimer, the term of this patent is extended or adjusted under 35 U.S.C. 154(b) by 0 days.

(21) Appl. No.: 17/645,821

(22) Filed: Dec. 23, 2021

(65) Prior Publication Data

US 2022/0211537 A1    Jul. 7, 2022

Related U.S. Application Data

(60) Provisional application No. 63/133,892, filed on Jan. 5, 2021.

(51) Int. Cl.
| | |
|---|---|
| *A61F 5/453* | (2006.01) |
| *A61F 5/44* | (2006.01) |
| *A61F 5/443* | (2006.01) |

(52) U.S. Cl.
CPC ............ *A61F 5/453* (2013.01); *A61F 5/4404* (2013.01); *A61F 5/443* (2013.01)

(58) Field of Classification Search
CPC ......... A61F 5/453; A61F 5/4404; A61F 5/443
See application file for complete search history.

(56) References Cited

U.S. PATENT DOCUMENTS 737,443 A      8/1903   Mooers
1,015,905 A  *   1/1912   Northrop ................ A61F 5/453
                                                      604/350

(Continued)

FOREIGN PATENT DOCUMENTS

AU        2018216821 A1    8/2019
AU        2021299304 A1    2/2023

(Continued)

OTHER PUBLICATIONS

US 9,908,683 B2, 03/2018, Sandhausen et al. (withdrawn)

(Continued)

*Primary Examiner* — Kai H Weng
*Assistant Examiner* — Katherine-Ph Minh Pham
(74) *Attorney, Agent, or Firm* — Ballard Spahr LLP

(57) ABSTRACT

An example male urine collection device for collection of urine discharged from a subject is disclosed. The male urine collection device includes a receptacle defining an internal volume, the receptacle configured to receive a penis and to collect urine, and a plurality of flaps movable to access the internal volume of the receptacle, the flaps configured to bias against the penis when the penis is at least partially received by the receptacle. In an embodiment, a male urine collection device includes a receptacle defining an internal volume, the receptacle configured to collect urine, and a clamshell having two halves movable with respect to each other via a hinge, the clamshell configured to close around the penis to secure the receptacle about the penis. The clamshell is removably secured to the penis via friction.

17 Claims, 12 Drawing Sheets

(56)　　　　　References Cited

U.S. PATENT DOCUMENTS

| | | |
|---|---|---|
| 1,032,841 A | 7/1912 | Koenig |
| 1,178,644 A | 4/1916 | Johnson |
| 1,387,726 A | 8/1921 | Karge |
| 1,742,080 A | 12/1929 | Jones |
| 1,979,899 A | 11/1934 | Obrien et al. |
| 2,241,010 A | 5/1941 | Chipley |
| 2,262,772 A | 11/1941 | Peder |
| 2,326,881 A | 8/1943 | Packer |
| 2,379,346 A | 6/1945 | Farrell |
| 2,485,555 A | 10/1949 | Bester |
| 2,571,357 A | 10/1951 | Charles |
| 2,613,670 A | 10/1952 | Edward |
| 2,616,426 A | 11/1952 | Adele |
| 2,644,234 A | 7/1953 | Earl |
| 2,648,335 A | 8/1953 | Chambers |
| 2,859,786 A | 11/1958 | Tupper |
| 2,944,551 A | 7/1960 | Carl |
| 2,968,046 A | 1/1961 | Duke |
| 2,971,512 A | 2/1961 | Reinhardt |
| 3,032,038 A | 5/1962 | Swinn |
| 3,077,883 A | 2/1963 | Hill |
| 3,087,938 A | 4/1963 | Hans et al. |
| 3,169,528 A | 2/1965 | Knox et al. |
| 3,171,506 A | 3/1965 | Therkel |
| 3,175,719 A | 3/1965 | Herndon |
| 3,194,238 A | 7/1965 | Breece |
| 3,198,994 A | 8/1965 | Hildebrandt et al. |
| 3,221,742 A | 12/1965 | Egon |
| 3,312,221 A | 4/1967 | Overment |
| 3,312,981 A | 4/1967 | Mcguire et al. |
| 3,349,768 A | 10/1967 | Keane |
| 3,362,590 A | 1/1968 | Gene |
| 3,366,116 A | 1/1968 | Huck |
| 3,398,848 A | 8/1968 | Donovan |
| 3,400,717 A | 9/1968 | Bruce et al. |
| 3,406,688 A | 10/1968 | Bruce |
| 3,424,163 A | 1/1969 | Gravdahl |
| 3,425,471 A | 2/1969 | Yates |
| 3,511,241 A | 5/1970 | Lee |
| 3,512,185 A | 5/1970 | Ellis |
| 3,520,300 A | 7/1970 | Flower |
| 3,528,423 A | 9/1970 | Lee |
| 3,613,123 A | 10/1971 | Langstrom |
| 3,648,700 A | 3/1972 | Warner |
| 3,651,810 A | 3/1972 | Ormerod |
| 3,661,155 A | 5/1972 | Lindan |
| 3,683,918 A | 8/1972 | Pizzella |
| 3,699,815 A | 10/1972 | Holbrook |
| 3,726,277 A | 4/1973 | Hirschman |
| 3,742,952 A | 7/1973 | Magers et al. |
| 3,757,355 A | 9/1973 | Allen et al. |
| 3,788,324 A | 1/1974 | Lim |
| 3,843,016 A | 10/1974 | Bornhorst et al. |
| 3,863,638 A | 2/1975 | Rogers et al. |
| 3,863,798 A | 2/1975 | Kurihara et al. |
| 3,864,759 A | 2/1975 | Horiuchi |
| 3,865,109 A | 2/1975 | Elmore et al. |
| 3,881,486 A | 5/1975 | Fenton |
| 3,881,489 A | 5/1975 | Hartwell |
| 3,915,189 A | 10/1975 | Holbrook et al. |
| 3,998,228 A | 12/1976 | Poidomani |
| 3,999,550 A | 12/1976 | Martin |
| 4,015,604 A | 4/1977 | Csillag |
| 4,020,843 A | 5/1977 | Kanall |
| 4,022,213 A | 5/1977 | Stein |
| 4,027,776 A | 6/1977 | Douglas |
| 4,064,962 A | 12/1977 | Hunt |
| 4,096,897 A | 6/1978 | Cammarata |
| 4,116,197 A | 9/1978 | Bermingham |
| 4,180,178 A | 12/1979 | Turner |
| 4,187,953 A | 2/1980 | Turner |
| 4,194,508 A | 3/1980 | Anderson |
| 4,200,102 A | 4/1980 | Duhamel et al. |
| 4,202,058 A | 5/1980 | Anderson |
| 4,203,503 A | 5/1980 | Bertotti et al. |
| 4,209,076 A | 6/1980 | Bertotti et al. |
| 4,223,677 A | 9/1980 | Anderson |
| 4,233,025 A | 11/1980 | Larson et al. |
| 4,233,978 A | 11/1980 | Hickey |
| 4,246,901 A | 1/1981 | Frosch et al. |
| 4,253,542 A | 3/1981 | Ruspa et al. |
| 4,257,418 A | 3/1981 | Hessner |
| 4,270,539 A | 6/1981 | Frosch et al. |
| 4,281,655 A | 8/1981 | Terauchi |
| 4,292,916 A | 10/1981 | Bradley et al. |
| 4,330,239 A | 5/1982 | Gannaway |
| 4,352,356 A | 10/1982 | Tong |
| 4,360,933 A | 11/1982 | Kimura et al. |
| 4,365,363 A | 12/1982 | Windauer |
| 4,375,841 A | 3/1983 | Vielbig |
| 4,387,726 A | 6/1983 | Denard |
| 4,403,991 A | 9/1983 | Hill |
| 4,425,130 A | 1/1984 | Desmarais |
| 4,446,986 A | 5/1984 | Bowen et al. |
| 4,453,938 A | 6/1984 | Brendling |
| 4,457,314 A | 7/1984 | Knowles |
| 4,476,879 A | 10/1984 | Jackson |
| 4,526,688 A | 7/1985 | Schmidt et al. |
| 4,528,703 A | 7/1985 | Kraus |
| D280,438 S | 9/1985 | Wendt |
| 4,551,141 A | 11/1985 | Mcneil |
| 4,553,968 A | 11/1985 | Komis |
| 4,581,026 A | 4/1986 | Schneider |
| 4,589,516 A | 5/1986 | Inoue et al. |
| 4,601,716 A | 7/1986 | Smith |
| 4,610,675 A | 9/1986 | Triunfol |
| 4,620,333 A | 11/1986 | Ritter |
| 4,626,250 A | 12/1986 | Schneider |
| 4,627,846 A | 12/1986 | Ternstroem |
| 4,631,061 A | 12/1986 | Martin |
| 4,650,477 A | 3/1987 | Johnson |
| 4,655,754 A | 4/1987 | Richmond et al. |
| 4,656,675 A | 4/1987 | Fajnsztajn |
| 4,681,570 A | 7/1987 | Dalton |
| 4,681,577 A | 7/1987 | Stern et al. |
| 4,692,160 A | 9/1987 | Nussbaumer |
| 4,707,864 A | 11/1987 | Ikematsu et al. |
| 4,713,065 A | 12/1987 | Koot |
| 4,713,066 A | 12/1987 | Komis |
| 4,723,953 A | 2/1988 | Pratt et al. |
| 4,735,841 A | 4/1988 | Sourdet |
| 4,743,236 A | 5/1988 | Manschot |
| 4,747,166 A | 5/1988 | Kuntz |
| 4,752,944 A | 6/1988 | Conrads et al. |
| 4,769,215 A | 9/1988 | Ehrenkranz |
| 4,771,484 A | 9/1988 | Mozell |
| 4,772,280 A | 9/1988 | Rooyakkers |
| 4,784,654 A | 11/1988 | Beecher |
| 4,790,830 A | 12/1988 | Hamacher |
| 4,790,835 A | 12/1988 | Elias |
| 4,791,686 A | 12/1988 | Taniguchi et al. |
| 4,795,449 A | 1/1989 | Schneider et al. |
| 4,798,603 A | 1/1989 | Meyer et al. |
| 4,799,928 A | 1/1989 | Crowley |
| 4,804,377 A | 2/1989 | Hanifl et al. |
| 4,812,053 A | 3/1989 | Bhattacharjee |
| 4,813,943 A | 3/1989 | Smith |
| 4,820,291 A | 4/1989 | Terauchi et al. |
| 4,820,297 A | 4/1989 | Kaufman et al. |
| 4,841,728 A | 6/1989 | Jean et al. |
| 4,846,818 A | 7/1989 | Keldahl et al. |
| 4,846,819 A | 7/1989 | Welch |
| 4,846,909 A | 7/1989 | Klug et al. |
| 4,865,595 A | 9/1989 | Heyden |
| 4,880,417 A | 11/1989 | Yabrov et al. |
| 4,882,794 A | 11/1989 | Stewart |
| 4,883,465 A | 11/1989 | Brennan |
| 4,886,498 A | 12/1989 | Newton |
| 4,886,508 A | 12/1989 | Washington |
| 4,886,509 A | 12/1989 | Mattsson |
| 4,889,532 A | 12/1989 | Metz et al. |
| 4,889,533 A | 12/1989 | Beecher |
| 4,890,691 A | 1/1990 | Ching-ho |
| 4,903,254 A | 2/1990 | Haas |

(56)  References Cited

U.S. PATENT DOCUMENTS

| | | |
|---|---|---|
| 4,904,248 A | 2/1990 | Vaillancourt |
| 4,905,692 A | 3/1990 | More |
| 4,936,838 A | 6/1990 | Cross et al. |
| 4,950,262 A | 8/1990 | Takagi |
| 4,955,922 A | 9/1990 | Terauchi |
| 4,957,487 A | 9/1990 | Gerow |
| 4,965,460 A | 10/1990 | Tanaka et al. |
| 4,986,823 A | 1/1991 | Anderson et al. |
| 4,987,849 A | 1/1991 | Sherman |
| 5,002,541 A | 3/1991 | Conkling et al. |
| 5,004,463 A | 4/1991 | Nigay |
| 5,013,308 A | 5/1991 | Sullivan et al. |
| 5,031,248 A | 7/1991 | Kemper |
| 5,045,077 A | 9/1991 | Blake |
| 5,045,283 A | 9/1991 | Patel |
| 5,049,144 A | 9/1991 | Payton |
| 5,053,339 A | 10/1991 | Patel |
| 5,057,092 A | 10/1991 | Webster |
| 5,058,088 A | 10/1991 | Haas et al. |
| 5,071,347 A | 12/1991 | McGuire |
| 5,078,707 A | 1/1992 | Peter |
| 5,084,037 A | 1/1992 | Barnett |
| 5,100,396 A | 3/1992 | Zamierowski |
| 5,112,324 A | 5/1992 | Wallace |
| 5,147,301 A | 9/1992 | Ruvio |
| 5,176,667 A | 1/1993 | Debring |
| 5,195,997 A | 3/1993 | Carns |
| 5,196,654 A | 3/1993 | Diflora et al. |
| 5,203,699 A | 4/1993 | McGuire |
| 5,244,458 A | 9/1993 | Takasu |
| 5,246,454 A | 9/1993 | Peterson |
| 5,267,988 A | 12/1993 | Farkas |
| 5,275,307 A | 1/1994 | Freese |
| 5,282,795 A | 2/1994 | Finney |
| 5,294,983 A | 3/1994 | Ersoz et al. |
| 5,295,983 A | 3/1994 | Kubo |
| 5,300,052 A | 4/1994 | Kubo |
| 5,304,749 A | 4/1994 | Crandell |
| 5,312,383 A | 5/1994 | Kubalak |
| 5,318,550 A | 6/1994 | Cermak et al. |
| 5,330,459 A | 7/1994 | Lavon et al. |
| 5,340,840 A | 8/1994 | Park et al. |
| 5,382,244 A | 1/1995 | Telang |
| 5,409,014 A | 4/1995 | Napoli et al. |
| 5,409,475 A | 4/1995 | Steer |
| 5,411,495 A | 5/1995 | Willingham |
| 5,423,784 A | 6/1995 | Metz |
| 5,456,246 A * | 10/1995 | Schmieding ........... A61B 17/06 |
| | | 606/151 |
| 5,466,229 A | 11/1995 | Elson et al. |
| 5,478,334 A | 12/1995 | Bernstein |
| 5,499,977 A | 3/1996 | Marx |
| 5,543,042 A | 8/1996 | Filan et al. |
| D373,928 S | 9/1996 | Green |
| 5,582,604 A | 12/1996 | Ahr et al. |
| 5,592,950 A | 1/1997 | Kopelowicz |
| 5,593,389 A | 1/1997 | Chang |
| 5,605,161 A | 2/1997 | Cross |
| 5,618,277 A | 4/1997 | Goulter |
| 5,628,735 A | 5/1997 | Skow |
| 5,636,643 A | 6/1997 | Argenta et al. |
| 5,637,104 A | 6/1997 | Ball et al. |
| 5,674,212 A | 10/1997 | Osborn et al. |
| 5,678,564 A | 10/1997 | Lawrence et al. |
| 5,678,654 A | 10/1997 | Uzawa |
| 5,687,429 A | 11/1997 | Rahlff |
| 5,695,485 A | 12/1997 | Duperret et al. |
| 5,700,254 A | 12/1997 | Mcdowall et al. |
| 5,701,612 A | 12/1997 | Daneshvar |
| 5,705,777 A | 1/1998 | Flanigan et al. |
| 5,735,835 A | 4/1998 | Holland |
| 5,752,944 A | 5/1998 | Dann et al. |
| 5,763,333 A | 6/1998 | Suzuki et al. |
| 5,772,644 A | 6/1998 | Bark et al. |
| 5,792,132 A | 8/1998 | Garcia |
| 5,827,243 A | 10/1998 | Palestrant |
| 5,827,247 A | 10/1998 | Kay |
| 5,827,250 A | 10/1998 | Fujioka et al. |
| 5,827,257 A | 10/1998 | Fujioka et al. |
| D401,699 S | 11/1998 | Herchenbach et al. |
| 5,859,393 A | 1/1999 | Cummins et al. |
| 5,865,378 A | 2/1999 | Hollinshead et al. |
| 5,876,393 A | 3/1999 | Ahr et al. |
| 5,887,291 A | 3/1999 | Bellizzi |
| 5,891,125 A | 4/1999 | Plumley |
| 5,894,608 A | 4/1999 | Birbara |
| D409,303 S | 5/1999 | Oepping |
| 5,911,222 A | 6/1999 | Lawrence et al. |
| 5,957,904 A | 9/1999 | Holland |
| 5,968,026 A | 10/1999 | Osborn et al. |
| 5,972,505 A | 10/1999 | Phillips et al. |
| 6,007,526 A | 12/1999 | Passalaqua et al. |
| 6,039,060 A | 3/2000 | Rower |
| 6,050,983 A | 4/2000 | Moore et al. |
| 6,059,762 A | 5/2000 | Boyer et al. |
| 6,063,064 A | 5/2000 | Tuckey et al. |
| 6,098,625 A | 8/2000 | Winkler |
| 6,105,174 A | 8/2000 | Karlsten et al. |
| 6,113,582 A | 9/2000 | Dwork |
| 6,117,163 A | 9/2000 | Bierman |
| 6,123,398 A | 9/2000 | Arai et al. |
| 6,129,718 A | 10/2000 | Wada et al. |
| 6,131,964 A | 10/2000 | Sareshwala |
| 6,152,902 A | 11/2000 | Christian et al. |
| 6,164,569 A | 12/2000 | Hollinshead et al. |
| 6,177,606 B1 | 1/2001 | Etheredge et al. |
| 6,209,142 B1 | 4/2001 | Mattsson et al. |
| 6,220,050 B1 | 4/2001 | Cooksey |
| 6,244,311 B1 | 6/2001 | Hand et al. |
| 6,248,096 B1 | 6/2001 | Dwork et al. |
| 6,263,887 B1 | 7/2001 | Dunn |
| 6,283,246 B1 | 9/2001 | Nishikawa |
| 6,296,627 B1 | 10/2001 | Edwards |
| 6,311,339 B1 | 11/2001 | Kraus |
| 6,336,919 B1 | 1/2002 | Davis et al. |
| 6,338,729 B1 | 1/2002 | Wada et al. |
| 6,352,525 B1 | 3/2002 | Wakabayashi |
| 6,394,988 B1 | 5/2002 | Hashimoto |
| 6,398,742 B1 | 6/2002 | Kim |
| 6,406,463 B1 | 6/2002 | Brown |
| 6,409,712 B1 | 6/2002 | Dutari et al. |
| 6,415,888 B2 | 7/2002 | An et al. |
| 6,416,500 B1 | 7/2002 | Wada et al. |
| 6,423,045 B1 | 7/2002 | Wise et al. |
| 6,428,521 B1 | 8/2002 | Droll |
| 6,428,522 B1 | 8/2002 | Dipalma et al. |
| 6,446,454 B1 | 9/2002 | Lee et al. |
| 6,467,570 B1 | 10/2002 | Herold |
| 6,475,198 B1 | 11/2002 | Lipman et al. |
| 6,479,726 B1 | 11/2002 | Cole et al. |
| 6,491,673 B1 | 12/2002 | Palumbo et al. |
| 6,508,794 B1 | 1/2003 | Palumbo et al. |
| 6,524,292 B1 | 2/2003 | Dipalma et al. |
| 6,540,729 B1 | 4/2003 | Wada et al. |
| 6,547,771 B2 | 4/2003 | Robertson et al. |
| 6,551,293 B1 | 4/2003 | Mitchell |
| 6,569,133 B2 | 5/2003 | Cheng et al. |
| D476,518 S | 7/2003 | Doppelt |
| 6,592,560 B2 | 7/2003 | Snyder et al. |
| 6,610,038 B1 | 8/2003 | Dipalma et al. |
| 6,618,868 B2 | 9/2003 | Minnick |
| 6,620,142 B1 | 9/2003 | Flueckiger |
| 6,629,651 B1 | 10/2003 | Male et al. |
| 6,635,037 B1 | 10/2003 | Bennett |
| 6,635,038 B2 | 10/2003 | Scovel |
| 6,652,495 B1 | 11/2003 | Walker |
| 6,666,850 B1 | 12/2003 | Ahr et al. |
| 6,685,684 B1 | 2/2004 | Falconer |
| 6,695,828 B1 | 2/2004 | Dipalma et al. |
| 6,699,174 B1 | 3/2004 | Bennett |
| 6,700,034 B1 | 3/2004 | Lindsay et al. |
| 6,702,793 B1 | 3/2004 | Sweetser et al. |
| 6,706,027 B2 | 3/2004 | Harvie et al. |
| 6,732,384 B2 | 5/2004 | Scott |

(56) References Cited

U.S. PATENT DOCUMENTS

| | | | |
|---|---|---|---|
| 6,736,977 | B1 | 5/2004 | Hall et al. |
| 6,740,066 | B2 | 5/2004 | Wolff et al. |
| 6,764,477 | B1 | 7/2004 | Chen et al. |
| 6,783,519 | B2 | 8/2004 | Samuelsson |
| 6,796,974 | B2 | 9/2004 | Palumbo et al. |
| 6,814,547 | B2 | 11/2004 | Childers et al. |
| 6,849,065 | B2 | 2/2005 | Schmidt et al. |
| 6,857,137 | B2 | 2/2005 | Otto |
| 6,885,690 | B2 | 4/2005 | Aggerstam et al. |
| 6,888,044 | B2 | 5/2005 | Fell et al. |
| 6,893,425 | B2 | 5/2005 | Dunn et al. |
| 6,912,737 | B2 | 7/2005 | Ernest et al. |
| 6,918,899 | B2 | 7/2005 | Harvie |
| 6,979,324 | B2 | 12/2005 | Bybordi et al. |
| 7,018,366 | B2 | 3/2006 | Easter |
| 7,066,411 | B2 | 6/2006 | Male et al. |
| 7,122,023 | B1 | 10/2006 | Hinoki |
| 7,125,399 | B2 | 10/2006 | Miskie |
| 7,131,964 | B2 | 11/2006 | Harvie |
| 7,135,012 | B2 | 11/2006 | Harvie |
| 7,141,043 | B2 | 11/2006 | Harvie |
| D533,972 | S | 12/2006 | La |
| 7,160,273 | B2 | 1/2007 | Greter et al. |
| 7,166,092 | B2 | 1/2007 | Elson et al. |
| 7,171,699 | B2 | 2/2007 | Ernest et al. |
| 7,171,871 | B2 | 2/2007 | Kozak |
| 7,179,951 | B2 | 2/2007 | Krishnaswamy-Mirle et al. |
| 7,181,781 | B1 | 2/2007 | Trabold et al. |
| 7,186,245 | B1 | 3/2007 | Cheng et al. |
| 7,192,424 | B2 | 3/2007 | Cooper |
| 7,219,764 | B1 | 5/2007 | Forbes |
| 7,220,250 | B2 | 5/2007 | Suzuki et al. |
| D562,975 | S | 2/2008 | Otto |
| 7,335,189 | B2 | 2/2008 | Harvie |
| 7,358,282 | B2 | 4/2008 | Krueger et al. |
| 7,390,320 | B2 | 6/2008 | Machida et al. |
| 7,438,706 | B2 | 10/2008 | Koizumi et al. |
| 7,488,310 | B2 | 2/2009 | Yang |
| 7,491,194 | B1 | 2/2009 | Oliwa |
| D591,106 | S | 4/2009 | Dominique et al. |
| 7,513,381 | B2 | 4/2009 | Heng et al. |
| 7,520,872 | B2 | 4/2009 | Biggie et al. |
| D593,801 | S | 6/2009 | Wilson et al. |
| 7,540,364 | B2 | 6/2009 | Sanderson |
| 7,549,511 | B2 | 6/2009 | Marocco |
| 7,549,512 | B2 | 6/2009 | Newberry |
| 7,585,293 | B2 | 9/2009 | Vermaak |
| 7,588,560 | B1 | 9/2009 | Dunlop |
| 7,637,905 | B2 | 12/2009 | Saadat et al. |
| 7,658,730 | B2 | 2/2010 | Conley |
| 7,665,359 | B2 | 2/2010 | Barber |
| 7,682,347 | B2 | 3/2010 | Parks et al. |
| 7,687,004 | B2 | 3/2010 | Allen |
| 7,695,459 | B2 | 4/2010 | Gilbert et al. |
| 7,695,460 | B2 | 4/2010 | Wada et al. |
| 7,699,818 | B2 | 4/2010 | Gilbert |
| 7,699,831 | B2 | 4/2010 | Bengtson et al. |
| 7,722,584 | B2 | 5/2010 | Tanaka et al. |
| 7,727,206 | B2 | 6/2010 | Gorres |
| 7,740,620 | B2 | 6/2010 | Gilbert et al. |
| 7,749,205 | B2 | 7/2010 | Tazoe et al. |
| 7,755,497 | B2 | 7/2010 | Wada et al. |
| 7,766,887 | B2 | 8/2010 | Burns et al. |
| D625,407 | S | 10/2010 | Koizumi et al. |
| 7,806,879 | B2 | 10/2010 | Brooks et al. |
| 7,811,272 | B2 | 10/2010 | Lindsay et al. |
| 7,815,067 | B2 | 10/2010 | Matsumoto et al. |
| 7,833,169 | B2 | 11/2010 | Hannon |
| 7,857,806 | B2 | 12/2010 | Karpowicz et al. |
| 7,866,942 | B2 | 1/2011 | Harvie |
| 7,871,385 | B2 | 1/2011 | Levinson et al. |
| 7,875,010 | B2 | 1/2011 | Frazier et al. |
| 7,901,389 | B2 | 3/2011 | Mombrinie |
| 7,927,320 | B2 | 4/2011 | Goldwasser et al. |
| 7,927,321 | B2 | 4/2011 | Marland |
| 7,931,634 | B2 | 4/2011 | Swiecicki et al. |
| 7,939,706 | B2 | 5/2011 | Okabe et al. |
| 7,946,443 | B2 | 5/2011 | Stull et al. |
| 7,947,025 | B2 | 5/2011 | Buglino et al. |
| 7,963,419 | B2 | 6/2011 | Burney et al. |
| 7,976,519 | B2 | 7/2011 | Bubb et al. |
| 7,993,318 | B2 | 8/2011 | Olsson et al. |
| 8,015,627 | B2 | 9/2011 | Baker et al. |
| 8,016,071 | B1 | 9/2011 | Martinus et al. |
| 8,028,460 | B2 | 10/2011 | Williams |
| 8,047,398 | B2 | 11/2011 | Dimartino et al. |
| 8,083,094 | B2 | 12/2011 | Caulfield et al. |
| 8,128,608 | B2 | 3/2012 | Thevenin |
| 8,181,651 | B2 | 5/2012 | Pinel |
| 8,181,819 | B2 | 5/2012 | Burney et al. |
| 8,211,063 | B2 | 7/2012 | Bierman et al. |
| 8,221,369 | B2 | 7/2012 | Parks et al. |
| 8,241,262 | B2 | 8/2012 | Mahnensmith |
| 8,277,426 | B2 | 10/2012 | Wilcox et al. |
| 8,287,508 | B1 | 10/2012 | Sanchez |
| 8,303,554 | B2 | 11/2012 | Tsai et al. |
| 8,322,565 | B2 | 12/2012 | Caulfield et al. |
| 8,337,477 | B2 | 12/2012 | Parks et al. |
| D674,241 | S | 1/2013 | Bickert et al. |
| 8,343,122 | B2 | 1/2013 | Gorres |
| 8,343,125 | B2 | 1/2013 | Kawazoe et al. |
| 8,353,074 | B2 | 1/2013 | Krebs |
| 8,353,886 | B2 | 1/2013 | Bester et al. |
| D676,241 | S | 2/2013 | Merrill |
| 8,388,587 | B1 | 3/2013 | Gmuer et al. |
| 8,388,588 | B2 | 3/2013 | Wada et al. |
| D679,807 | S | 4/2013 | Burgess et al. |
| 8,425,482 | B2 | 4/2013 | Khoubnazar |
| 8,434,586 | B2 | 5/2013 | Pawelski et al. |
| 8,449,510 | B2 | 5/2013 | Martini et al. |
| D684,260 | S | 6/2013 | Lund et al. |
| 8,470,230 | B2 | 6/2013 | Caulfield et al. |
| 8,479,941 | B2 | 7/2013 | Matsumoto et al. |
| 8,479,949 | B2 | 7/2013 | Henkel |
| 8,500,719 | B1 * | 8/2013 | Simpson, Jr. ........... A61F 5/453 604/349 |
| 8,512,301 | B2 | 8/2013 | Ma |
| 8,529,530 | B2 | 9/2013 | Koch et al. |
| 8,535,284 | B2 | 9/2013 | Joder et al. |
| 8,546,639 | B2 | 10/2013 | Wada et al. |
| 8,551,075 | B2 | 10/2013 | Bengtson |
| 8,568,376 | B2 | 10/2013 | Delattre et al. |
| D694,404 | S | 11/2013 | Burgess et al. |
| 8,585,683 | B2 | 11/2013 | Bengtson et al. |
| 8,586,583 | B2 | 11/2013 | Hamblin et al. |
| 8,652,112 | B2 | 2/2014 | Johannison et al. |
| 8,669,412 | B2 | 3/2014 | Fernkvist et al. |
| D702,973 | S | 4/2014 | Norland et al. |
| 8,703,032 | B2 | 4/2014 | Menon et al. |
| D704,330 | S | 5/2014 | Cicatelli |
| D704,510 | S | 5/2014 | Mason et al. |
| D705,423 | S | 5/2014 | Walsh Cutler |
| D705,926 | S | 5/2014 | Burgess et al. |
| 8,714,394 | B2 | 5/2014 | Wulf |
| 8,715,267 | B2 | 5/2014 | Bengtson et al. |
| 8,757,425 | B2 | 6/2014 | Copeland |
| 8,777,032 | B2 | 7/2014 | Biesecker et al. |
| 8,808,260 | B2 | 8/2014 | Koch et al. |
| 8,864,730 | B2 | 10/2014 | Conway et al. |
| 8,881,923 | B2 | 11/2014 | Higginson |
| 8,882,731 | B2 | 11/2014 | Suzuki et al. |
| 8,936,585 | B2 | 1/2015 | Carson et al. |
| D729,581 | S | 5/2015 | Boroski |
| 9,028,460 | B2 | 5/2015 | Medeiros |
| 9,056,698 | B2 | 6/2015 | Noer |
| 9,078,792 | B2 | 7/2015 | Ruiz |
| 9,145,879 | B2 | 9/2015 | Pirovano et al. |
| 9,173,602 | B2 | 11/2015 | Gilbert |
| 9,173,799 | B2 | 11/2015 | Tanimoto et al. |
| 9,187,220 | B2 | 11/2015 | Biesecker et al. |
| 9,199,772 | B2 | 12/2015 | Krippendorf |
| 9,233,020 | B2 | 1/2016 | Matsumiya |
| 9,248,058 | B2 | 2/2016 | Conway et al. |
| 9,308,118 | B1 | 4/2016 | Dupree et al. |

(56) References Cited

U.S. PATENT DOCUMENTS

| | | | |
|---|---|---|---|
| 9,309,029 | B2 | 4/2016 | Incorvia et al. |
| 9,333,281 | B2 | 5/2016 | Giezendanner et al. |
| 9,381,108 | B2 | 7/2016 | Longoni et al. |
| 9,382,047 | B2 | 7/2016 | Schmidtner et al. |
| 9,402,424 | B2 | 8/2016 | Roy |
| 9,456,937 | B2 | 10/2016 | Ellis |
| 9,480,595 | B2 | 11/2016 | Baham et al. |
| 9,517,865 | B2 | 12/2016 | Albers et al. |
| D777,941 | S | 1/2017 | Piramoon |
| 9,533,806 | B2 | 1/2017 | Ding et al. |
| 9,550,611 | B2 | 1/2017 | Hodge |
| 9,555,930 | B2 | 1/2017 | Campbell et al. |
| 9,623,159 | B2 | 4/2017 | Locke |
| D789,522 | S | 6/2017 | Burgess et al. |
| 9,687,849 | B2 | 6/2017 | Bruno et al. |
| 9,694,949 | B2 | 7/2017 | Hendricks et al. |
| 9,709,048 | B2 | 7/2017 | Kinjo |
| 9,713,547 | B2 | 7/2017 | Lee et al. |
| 9,732,754 | B2 | 8/2017 | Huang et al. |
| 9,752,564 | B2 | 9/2017 | Arceno et al. |
| 9,788,992 | B2 | 10/2017 | Harvie |
| D804,907 | S | 12/2017 | Sandoval |
| 9,868,564 | B2 | 1/2018 | Mcgirr et al. |
| D814,239 | S | 4/2018 | Arora |
| D817,484 | S | 5/2018 | Lafond |
| 10,037,640 | B2 | 7/2018 | Gordon |
| 10,058,470 | B2 | 8/2018 | Phillips |
| 10,098,990 | B2 | 10/2018 | Koch et al. |
| D835,264 | S | 12/2018 | Mozzicato et al. |
| D835,779 | S | 12/2018 | Mozzicato et al. |
| D840,533 | S | 2/2019 | Mozzicato et al. |
| D840,534 | S | 2/2019 | Mozzicato et al. |
| 10,225,376 | B2 | 3/2019 | Perez Martinez |
| 10,226,376 | B2 | 3/2019 | Sanchez et al. |
| 10,258,517 | B1 | 4/2019 | Maschino et al. |
| D848,612 | S | 5/2019 | Mozzicato et al. |
| 10,307,305 | B1 | 6/2019 | Hodges |
| 10,335,121 | B2 | 7/2019 | Desai |
| D856,512 | S | 8/2019 | Cowart et al. |
| 10,376,406 | B2 | 8/2019 | Newton |
| 10,376,407 | B2 | 8/2019 | Newton |
| 10,390,989 | B2 | 8/2019 | Sanchez et al. |
| D858,144 | S | 9/2019 | Fu |
| 10,406,039 | B2 | 9/2019 | Villarreal |
| 10,407,222 | B2 | 9/2019 | Allen |
| 10,478,356 | B2 | 11/2019 | Griffin |
| 10,500,108 | B1 | 12/2019 | Maschino et al. |
| 10,502,198 | B2 | 12/2019 | Stumpf et al. |
| 10,538,366 | B2 | 1/2020 | Pentelovitch et al. |
| 10,569,938 | B2 | 2/2020 | Zhao et al. |
| 10,577,156 | B2 | 3/2020 | Dagnelie et al. |
| RE47,930 | E | 4/2020 | Cho |
| 10,618,721 | B2 | 4/2020 | Vazin |
| D884,390 | S | 5/2020 | Wang |
| 10,669,079 | B2 | 6/2020 | Freedman et al. |
| D892,315 | S | 8/2020 | Airy |
| 10,730,672 | B2 | 8/2020 | Bertram et al. |
| 10,737,848 | B2 | 8/2020 | Philip et al. |
| 10,765,854 | B2 | 9/2020 | Law et al. |
| 10,766,670 | B2 | 9/2020 | Kittmann |
| 10,799,386 | B1 | 10/2020 | Harrison |
| 10,806,642 | B2 | 10/2020 | Tagomori et al. |
| D901,214 | S | 11/2020 | Hu |
| 10,849,799 | B2 | 12/2020 | Nishikawa et al. |
| 10,857,025 | B2 | 12/2020 | Davis et al. |
| 10,865,017 | B1 | 12/2020 | Cowart et al. |
| 10,889,412 | B2 | 1/2021 | West et al. |
| 10,913,581 | B2 | 2/2021 | Stahlecker |
| D912,244 | S | 3/2021 | Rehm et al. |
| 10,952,889 | B2 | 3/2021 | Newton et al. |
| 10,973,378 | B2 | 4/2021 | Ryu et al. |
| 10,973,678 | B2 | 4/2021 | Newton et al. |
| 10,974,874 | B2 | 4/2021 | Ragias et al. |
| 11,000,401 | B2 | 5/2021 | Ecklund et al. |
| D923,365 | S | 6/2021 | Wang |
| 11,026,829 | B2 | 6/2021 | Harvie |
| 11,027,900 | B2 | 6/2021 | Liu |
| 11,045,346 | B2 | 6/2021 | Argent et al. |
| D928,946 | S | 8/2021 | Sanchez et al. |
| 11,090,183 | B2 | 8/2021 | Sanchez et al. |
| 11,160,695 | B2 | 11/2021 | Febo et al. |
| 11,160,697 | B2 | 11/2021 | Maschino et al. |
| 11,168,420 | B2 | 11/2021 | Kinugasa et al. |
| 11,179,506 | B2 | 11/2021 | Barr et al. |
| 11,207,206 | B2 | 12/2021 | Sharma et al. |
| 11,226,376 | B2 | 1/2022 | Yamauchi et al. |
| 11,253,389 | B2 | 2/2022 | Sharma et al. |
| 11,253,407 | B2 | 2/2022 | Miao et al. |
| 11,326,586 | B2 | 5/2022 | Milner et al. |
| 11,369,508 | B2 | 6/2022 | Ecklund et al. |
| 11,369,524 | B2 | 6/2022 | Hubbard et al. |
| 11,376,152 | B2 | 7/2022 | Sanchez et al. |
| 11,382,786 | B2 | 7/2022 | Sanchez et al. |
| 11,382,788 | B2 | 7/2022 | Hjorth et al. |
| 11,389,318 | B2 | 7/2022 | Radl et al. |
| 11,395,871 | B2 | 7/2022 | Radl et al. |
| 11,399,990 | B2 | 8/2022 | Suyama |
| 11,426,303 | B2 | 8/2022 | Davis et al. |
| 11,504,265 | B2 | 11/2022 | Godinez et al. |
| 11,529,252 | B2 | 12/2022 | Glithero et al. |
| 11,547,788 | B2 | 1/2023 | Radl et al. |
| 11,806,266 | B2 | 11/2023 | Sanchez et al. |
| 11,839,567 | B2 | 12/2023 | Davis et al. |
| D1,010,109 | S | 1/2024 | Ecklund et al. |
| 11,857,716 | B2 | 1/2024 | Lee et al. |
| 11,865,030 | B2 | 1/2024 | Davis et al. |
| 11,890,221 | B2 | 2/2024 | Ulreich et al. |
| 11,925,575 | B2 | 3/2024 | Newton |
| 11,938,053 | B2 | 3/2024 | Austermann et al. |
| 11,944,740 | B2 | 4/2024 | Hughett et al. |
| 11,994,122 | B2 | 5/2024 | Bodain |
| 11,998,475 | B2 | 6/2024 | Becker et al. |
| 12,023,457 | B2 | 7/2024 | Mann et al. |
| 12,042,422 | B2 | 7/2024 | Davis et al. |
| D1,038,385 | S | 8/2024 | Ecklund et al. |
| 12,090,083 | B2 | 9/2024 | Ecklund et al. |
| 12,133,813 | B2 | 11/2024 | Ulreich et al. |
| 12,138,195 | B2 | 11/2024 | Alder et al. |
| 2001/0037097 | A1 | 11/2001 | Cheng et al. |
| 2001/0054426 | A1 | 12/2001 | Knudson et al. |
| 2002/0019614 | A1 | 2/2002 | Woon |
| 2002/0026161 | A1 | 2/2002 | Grundke |
| 2002/0026163 | A1 | 2/2002 | Grundke |
| 2002/0087131 | A1 | 7/2002 | Wolff et al. |
| 2002/0091364 | A1 | 7/2002 | Prabhakar |
| 2002/0189992 | A1 | 12/2002 | Schmidt et al. |
| 2002/0193760 | A1 | 12/2002 | Thompson |
| 2003/0004436 | A1 | 1/2003 | Schmidt et al. |
| 2003/0032931 | A1* | 2/2003 | Grundke ................ A61F 5/453 |
| | | | 604/347 |
| 2003/0032944 | A1 | 2/2003 | Cawood |
| 2003/0073964 | A1 | 4/2003 | Palumbo et al. |
| 2003/0120178 | A1 | 6/2003 | Heki |
| 2003/0157859 | A1 | 8/2003 | Ishikawa |
| 2003/0181880 | A1 | 9/2003 | Schwartz |
| 2003/0195484 | A1 | 10/2003 | Harvie |
| 2003/0204173 | A1 | 10/2003 | Burns et al. |
| 2003/0233079 | A1 | 12/2003 | Parks et al. |
| 2004/0006321 | A1 | 1/2004 | Cheng et al. |
| 2004/0015141 | A1 | 1/2004 | Cheng et al. |
| 2004/0056122 | A1 | 3/2004 | Male et al. |
| 2004/0084465 | A1 | 5/2004 | Luburic |
| 2004/0127872 | A1 | 7/2004 | Petryk et al. |
| 2004/0128749 | A1 | 7/2004 | Scott |
| 2004/0143229 | A1 | 7/2004 | Easter |
| 2004/0147863 | A1 | 7/2004 | Diaz et al. |
| 2004/0147894 | A1 | 7/2004 | Mizutani et al. |
| 2004/0158221 | A1 | 8/2004 | Mizutani et al. |
| 2004/0176731 | A1 | 9/2004 | Cheng et al. |
| 2004/0176746 | A1 | 9/2004 | Forral |
| 2004/0191919 | A1 | 9/2004 | Unger et al. |
| 2004/0200936 | A1 | 10/2004 | Opperthauser |
| 2004/0207530 | A1 | 10/2004 | Nielsen |
| 2004/0236292 | A1 | 11/2004 | Tazoe et al. |

(56) References Cited

U.S. PATENT DOCUMENTS

| | | |
|---|---|---|
| 2004/0243075 A1 | 12/2004 | Harvie |
| 2004/0254547 A1 | 12/2004 | Okabe et al. |
| 2005/0010182 A1 | 1/2005 | Parks et al. |
| 2005/0010197 A1 | 1/2005 | Lau et al. |
| 2005/0033248 A1 | 2/2005 | Machida et al. |
| 2005/0065471 A1 | 3/2005 | Kuntz |
| 2005/0070861 A1 | 3/2005 | Okabe et al. |
| 2005/0070862 A1 | 3/2005 | Tazoe et al. |
| 2005/0082300 A1 | 4/2005 | Modrell et al. |
| 2005/0097662 A1 | 5/2005 | Leimkuhler et al. |
| 2005/0101924 A1 | 5/2005 | Elson et al. |
| 2005/0119630 A1 | 6/2005 | Harvie |
| 2005/0137557 A1 | 6/2005 | Swiecicki et al. |
| 2005/0154360 A1 | 7/2005 | Harvie |
| 2005/0177070 A1 | 8/2005 | Levinson et al. |
| 2005/0197639 A1 | 9/2005 | Mombrinie |
| 2005/0197645 A1 | 9/2005 | Karpowicz et al. |
| 2005/0273920 A1 | 12/2005 | Marinas |
| 2005/0277904 A1 | 12/2005 | Chase et al. |
| 2005/0279359 A1 | 12/2005 | Leblanc et al. |
| 2006/0004332 A1 | 1/2006 | Marx |
| 2006/0015080 A1 | 1/2006 | Mahnensmith |
| 2006/0015081 A1 | 1/2006 | Suzuki et al. |
| 2006/0016778 A1 | 1/2006 | Park |
| 2006/0069359 A1 | 3/2006 | Dipalma et al. |
| 2006/0079854 A1 | 4/2006 | Kay et al. |
| 2006/0111648 A1 | 5/2006 | Vermaak |
| 2006/0155214 A1 | 7/2006 | Wightman |
| 2006/0171997 A1 | 8/2006 | Gruenbacher et al. |
| 2006/0180566 A1 | 8/2006 | Mataya |
| 2006/0200102 A1 | 9/2006 | Cooper |
| 2006/0229575 A1 | 10/2006 | Boiarski |
| 2006/0229576 A1 | 10/2006 | Conway et al. |
| 2006/0231648 A1 | 10/2006 | Male et al. |
| 2006/0235266 A1 | 10/2006 | Nan |
| 2006/0235359 A1 | 10/2006 | Marland |
| 2006/0241553 A1 | 10/2006 | Harvie |
| 2006/0269439 A1 | 11/2006 | White |
| 2006/0277670 A1 | 12/2006 | Baker et al. |
| 2007/0006368 A1 | 1/2007 | Key et al. |
| 2007/0010797 A1 | 1/2007 | Nishtala et al. |
| 2007/0016152 A1 | 1/2007 | Karpowicz et al. |
| 2007/0038194 A1 | 2/2007 | Wada et al. |
| 2007/0055209 A1 | 3/2007 | Patel et al. |
| 2007/0073252 A1 | 3/2007 | Forgrave |
| 2007/0117880 A1 | 5/2007 | Elson et al. |
| 2007/0118993 A1 | 5/2007 | Bates |
| 2007/0135786 A1 | 6/2007 | Schmidt et al. |
| 2007/0137718 A1 | 6/2007 | Rushlander et al. |
| 2007/0149935 A1 | 6/2007 | Dirico |
| 2007/0191804 A1 | 8/2007 | Coley |
| 2007/0203464 A1 | 8/2007 | Green et al. |
| 2007/0214553 A1 | 9/2007 | Carromba et al. |
| 2007/0225663 A1 | 9/2007 | Watt et al. |
| 2007/0225666 A1 | 9/2007 | Otto |
| 2007/0225668 A1 | 9/2007 | Otto |
| 2007/0266486 A1 | 11/2007 | Ramirez |
| 2007/0282309 A1 | 12/2007 | Bengtson et al. |
| 2008/0004576 A1 | 1/2008 | Tanaka et al. |
| 2008/0015526 A1 | 1/2008 | Reiner et al. |
| 2008/0015527 A1 | 1/2008 | House |
| 2008/0033386 A1 | 2/2008 | Okabe et al. |
| 2008/0041869 A1 | 2/2008 | Backaert |
| 2008/0091153 A1 | 4/2008 | Harvie |
| 2008/0091158 A1 | 4/2008 | Yang |
| 2008/0114327 A1 | 5/2008 | Barge |
| 2008/0167634 A1 | 7/2008 | Kouta et al. |
| 2008/0183157 A1 | 7/2008 | Walters |
| 2008/0215031 A1 | 9/2008 | Belfort et al. |
| 2008/0234642 A1 | 9/2008 | Patterson et al. |
| 2008/0269703 A1 | 10/2008 | Collins et al. |
| 2008/0281282 A1 | 11/2008 | Finger et al. |
| 2008/0287894 A1 | 11/2008 | Van Den Heuvel et al. |
| 2008/0312550 A1 | 12/2008 | Nishtala et al. |
| 2009/0025717 A1 | 1/2009 | Pinel |
| 2009/0048570 A1 | 2/2009 | Jensen |
| 2009/0056003 A1 | 3/2009 | Ivie et al. |
| 2009/0069761 A1 | 3/2009 | Vogel |
| 2009/0069765 A1 | 3/2009 | Wortham |
| 2009/0120179 A1 | 5/2009 | Nylander et al. |
| 2009/0192482 A1 | 7/2009 | Dodge et al. |
| 2009/0234312 A1 | 9/2009 | Otoole et al. |
| 2009/0251510 A1 | 10/2009 | Noro et al. |
| 2009/0259206 A1 | 10/2009 | Kai et al. |
| 2009/0264840 A1 | 10/2009 | Virginio |
| 2009/0270822 A1 | 10/2009 | Medeiros |
| 2009/0281510 A1 | 11/2009 | Fisher |
| 2009/0283982 A1 | 11/2009 | Thomas |
| 2010/0004612 A1 | 1/2010 | Thevenin |
| 2010/0058660 A1 | 3/2010 | Williams |
| 2010/0121289 A1 | 5/2010 | Parks et al. |
| 2010/0160882 A1 | 6/2010 | Lowe |
| 2010/0174250 A1 | 7/2010 | Hu et al. |
| 2010/0179493 A1 | 7/2010 | Heagle et al. |
| 2010/0185168 A1 | 7/2010 | Graauw et al. |
| 2010/0198172 A1 | 8/2010 | Wada et al. |
| 2010/0211032 A1 | 8/2010 | Tsai et al. |
| 2010/0234820 A1 | 9/2010 | Tsai et al. |
| 2010/0241104 A1 | 9/2010 | Gilbert |
| 2010/0263113 A1 | 10/2010 | Shelton et al. |
| 2010/0310845 A1 | 12/2010 | Bond et al. |
| 2011/0028920 A1 | 2/2011 | Johannison |
| 2011/0028922 A1 | 2/2011 | Kay et al. |
| 2011/0034889 A1 | 2/2011 | Smith |
| 2011/0036837 A1 | 2/2011 | Shang |
| 2011/0040267 A1 | 2/2011 | Wada et al. |
| 2011/0040271 A1 | 2/2011 | Rogers et al. |
| 2011/0054426 A1 | 3/2011 | Stewart et al. |
| 2011/0060299 A1 | 3/2011 | Wada et al. |
| 2011/0060300 A1 | 3/2011 | Weig et al. |
| 2011/0077495 A1 | 3/2011 | Gilbert |
| 2011/0077606 A1 | 3/2011 | Wilcox et al. |
| 2011/0087337 A1 | 4/2011 | Forsell |
| 2011/0137273 A1 | 6/2011 | Muellejans et al. |
| 2011/0145993 A1 | 6/2011 | Rader et al. |
| 2011/0152802 A1 | 6/2011 | Dicamillo et al. |
| 2011/0164147 A1 | 7/2011 | Takahashi et al. |
| 2011/0172620 A1 | 7/2011 | Khambatta |
| 2011/0172625 A1 | 7/2011 | Wada et al. |
| 2011/0202024 A1 | 8/2011 | Cozzens |
| 2011/0238023 A1 | 9/2011 | Slayton |
| 2011/0240648 A1 | 10/2011 | Tucker |
| 2011/0251572 A1 | 10/2011 | Nishtala et al. |
| 2011/0265889 A1 | 11/2011 | Tanaka et al. |
| 2011/0276020 A1 | 11/2011 | Mitsui |
| 2012/0029452 A1 | 2/2012 | Roedsten |
| 2012/0035577 A1 | 2/2012 | Tomes et al. |
| 2012/0041400 A1 | 2/2012 | Christensen |
| 2012/0059328 A1 | 3/2012 | Dikeman et al. |
| 2012/0066825 A1 | 3/2012 | Birbara et al. |
| 2012/0103347 A1 | 5/2012 | Wheaton et al. |
| 2012/0116336 A1 | 5/2012 | Sharma et al. |
| 2012/0137420 A1 | 6/2012 | Gordon et al. |
| 2012/0165768 A1 | 6/2012 | Sekiyama et al. |
| 2012/0165786 A1 | 6/2012 | Chappa et al. |
| 2012/0209216 A1 | 8/2012 | Jensen et al. |
| 2012/0210503 A1 | 8/2012 | Anzivino et al. |
| 2012/0233761 A1 | 9/2012 | Huang |
| 2012/0245541 A1 | 9/2012 | Suzuki et al. |
| 2012/0245542 A1 | 9/2012 | Suzuki et al. |
| 2012/0245547 A1 | 9/2012 | Wilcox et al. |
| 2012/0253303 A1 | 10/2012 | Suzuki et al. |
| 2012/0271259 A1 | 10/2012 | Ulert |
| 2012/0296305 A1 | 11/2012 | Barraza Khaled et al. |
| 2012/0316522 A1 | 12/2012 | Carter et al. |
| 2012/0330256 A1 | 12/2012 | Wilcox et al. |
| 2013/0006206 A1 | 1/2013 | Wada et al. |
| 2013/0045651 A1 | 2/2013 | Esteves et al. |
| 2013/0053804 A1 | 2/2013 | Soerensen et al. |
| 2013/0096523 A1 | 4/2013 | Chang et al. |
| 2013/0110059 A1 | 5/2013 | Kossow et al. |
| 2013/0138064 A1 | 5/2013 | Stroebech et al. |
| 2013/0150813 A1 | 6/2013 | Gordon et al. |
| 2013/0218112 A1 | 8/2013 | Thompson |

(56) References Cited

U.S. PATENT DOCUMENTS

| | | |
|---|---|---|
| 2013/0245496 A1 | 9/2013 | Wells et al. |
| 2013/0245586 A1 | 9/2013 | Jha |
| 2013/0292537 A1 | 11/2013 | Dirico |
| 2013/0330501 A1 | 12/2013 | Aizenberg et al. |
| 2014/0005647 A1 | 1/2014 | Shuffler et al. |
| 2014/0031774 A1 | 1/2014 | Bengtson |
| 2014/0039432 A1 | 2/2014 | Dunbar et al. |
| 2014/0107599 A1 | 4/2014 | Fink et al. |
| 2014/0157499 A1 | 6/2014 | Suzuki et al. |
| 2014/0171889 A1 | 6/2014 | Hopman et al. |
| 2014/0182051 A1 | 7/2014 | Tanimoto et al. |
| 2014/0196189 A1 | 7/2014 | Lee et al. |
| 2014/0276501 A1 | 9/2014 | Cisko |
| 2014/0303582 A1 | 10/2014 | Wright et al. |
| 2014/0316381 A1 | 10/2014 | Reglin |
| 2014/0325746 A1 | 11/2014 | Block |
| 2014/0348139 A1 | 11/2014 | Gomez Martinez |
| 2014/0352050 A1 | 12/2014 | Yao et al. |
| 2014/0371628 A1 | 12/2014 | Desai |
| 2015/0045757 A1 | 2/2015 | Lee et al. |
| 2015/0047114 A1 | 2/2015 | Ramirez |
| 2015/0048089 A1 | 2/2015 | Robertson |
| 2015/0135423 A1 | 5/2015 | Sharpe et al. |
| 2015/0157300 A1 | 6/2015 | Ealovega et al. |
| 2015/0209188 A1 | 7/2015 | Scheremet et al. |
| 2015/0209194 A1 | 7/2015 | Heyman |
| 2015/0290425 A1 | 10/2015 | Macy et al. |
| 2015/0320583 A1 | 11/2015 | Harvie |
| 2015/0329255 A1 | 11/2015 | Rzepecki |
| 2015/0342799 A1 | 12/2015 | Michiels et al. |
| 2015/0359660 A1 | 12/2015 | Harvie |
| 2015/0366699 A1 | 12/2015 | Nelson |
| 2016/0029998 A1 | 2/2016 | Brister et al. |
| 2016/0030228 A1 | 2/2016 | Jones |
| 2016/0038356 A1 | 2/2016 | Yao et al. |
| 2016/0058322 A1 | 3/2016 | Brister et al. |
| 2016/0060001 A1 | 3/2016 | Wada et al. |
| 2016/0100976 A1 | 4/2016 | Conway et al. |
| 2016/0106604 A1 | 4/2016 | Timm |
| 2016/0113809 A1 | 4/2016 | Kim |
| 2016/0135792 A1* | 5/2016 | Cai .................... A61H 23/0254 |
| | | 601/46 |
| 2016/0183689 A1 | 6/2016 | Miner |
| 2016/0256022 A1 | 9/2016 | Le |
| 2016/0270982 A1 | 9/2016 | Raycheck et al. |
| 2016/0278662 A1 | 9/2016 | Brister et al. |
| 2016/0357400 A1 | 12/2016 | Penha et al. |
| 2016/0366699 A1 | 12/2016 | Zhang et al. |
| 2016/0367226 A1 | 12/2016 | Newton et al. |
| 2016/0367411 A1 | 12/2016 | Justiz et al. |
| 2016/0374848 A1 | 12/2016 | Sanchez et al. |
| 2017/0007438 A1 | 1/2017 | Harvie |
| 2017/0014560 A1 | 1/2017 | Minskoff et al. |
| 2017/0042748 A1 | 2/2017 | Griffin |
| 2017/0100276 A1 | 4/2017 | Joh |
| 2017/0128638 A1 | 5/2017 | Giezendanner et al. |
| 2017/0136209 A1 | 5/2017 | Burnett et al. |
| 2017/0143534 A1 | 5/2017 | Sanchez |
| 2017/0165100 A1 | 6/2017 | Jackson et al. |
| 2017/0165405 A1 | 6/2017 | Muser et al. |
| 2017/0189225 A1 | 7/2017 | Voorhees et al. |
| 2017/0202692 A1 | 7/2017 | Laniado |
| 2017/0216081 A1 | 8/2017 | Accosta |
| 2017/0238911 A1 | 8/2017 | Duval |
| 2017/0246026 A1 | 8/2017 | Laniado |
| 2017/0252014 A1 | 9/2017 | Siller Gonzalez et al. |
| 2017/0252202 A9 | 9/2017 | Sanchez et al. |
| 2017/0266031 A1 | 9/2017 | Sanchez et al. |
| 2017/0266658 A1 | 9/2017 | Bruno et al. |
| 2017/0281399 A1 | 10/2017 | Vanmiddendorp et al. |
| 2017/0312116 A1 | 11/2017 | Laniado |
| 2017/0325788 A1 | 11/2017 | Ealovega et al. |
| 2017/0333244 A1 | 11/2017 | Laniado |
| 2017/0348139 A1 | 12/2017 | Newton et al. |
| 2017/0354532 A1 | 12/2017 | Holt |
| 2017/0354551 A1 | 12/2017 | Gawley et al. |
| 2017/0367873 A1 | 12/2017 | Grannum |
| 2018/0002075 A1 | 1/2018 | Lee |
| 2018/0008451 A1 | 1/2018 | Stroebech |
| 2018/0008804 A1 | 1/2018 | Laniado |
| 2018/0021218 A1 | 1/2018 | Brosch et al. |
| 2018/0028349 A1 | 2/2018 | Newton et al. |
| 2018/0037384 A1 | 2/2018 | Archeny et al. |
| 2018/0049910 A1 | 2/2018 | Newton |
| 2018/0064572 A1 | 3/2018 | Wiltshire |
| 2018/0104131 A1 | 4/2018 | Killian |
| 2018/0127187 A1 | 5/2018 | Sewell |
| 2018/0193215 A1 | 7/2018 | Davies et al. |
| 2018/0200101 A1 | 7/2018 | Su |
| 2018/0228642 A1 | 8/2018 | Davis et al. |
| 2018/0256384 A1 | 9/2018 | Kasirye |
| 2018/0271694 A1 | 9/2018 | Fernandez et al. |
| 2018/0317892 A1 | 11/2018 | Catlin |
| 2018/0325748 A1 | 11/2018 | Sharma et al. |
| 2019/0001030 A1 | 1/2019 | Braga et al. |
| 2019/0021899 A1 | 1/2019 | Vlet |
| 2019/0038451 A1 | 2/2019 | Harvie |
| 2019/0046102 A1 | 2/2019 | Kushnir et al. |
| 2019/0059938 A1 | 2/2019 | Holsten |
| 2019/0091059 A1 | 3/2019 | Gabriel |
| 2019/0100362 A1 | 4/2019 | Meyers et al. |
| 2019/0133814 A1 | 5/2019 | Tammen et al. |
| 2019/0142624 A1 | 5/2019 | Sanchez et al. |
| 2019/0224036 A1 | 7/2019 | Sanchez et al. |
| 2019/0240079 A1 | 8/2019 | Tuli |
| 2019/0247222 A1* | 8/2019 | Ecklund .................. A61F 5/443 |
| 2019/0247223 A1 | 8/2019 | Brun et al. |
| 2019/0247623 A1 | 8/2019 | Helm et al. |
| 2019/0282391 A1 | 9/2019 | Johannes et al. |
| 2019/0314189 A1 | 10/2019 | Acosta |
| 2019/0314190 A1 | 10/2019 | Sanchez et al. |
| 2019/0321587 A1 | 10/2019 | Mcmenamin et al. |
| 2019/0344934 A1 | 11/2019 | Faerber et al. |
| 2019/0365307 A1 | 12/2019 | Laing et al. |
| 2019/0365561 A1 | 12/2019 | Newton et al. |
| 2019/0374373 A1 | 12/2019 | Joh |
| 2020/0008985 A1 | 1/2020 | Nguyen et al. |
| 2020/0016012 A1 | 1/2020 | Dutkiewicz |
| 2020/0030595 A1 | 1/2020 | Boukidjian et al. |
| 2020/0046544 A1 | 2/2020 | Godinez et al. |
| 2020/0055638 A1 | 2/2020 | Lau et al. |
| 2020/0070392 A1 | 3/2020 | Huber et al. |
| 2020/0085609 A1 | 3/2020 | Schelch et al. |
| 2020/0085610 A1 | 3/2020 | Cohn et al. |
| 2020/0086090 A1 | 3/2020 | Von Weymarn-schärli et al. |
| 2020/0107518 A1 | 4/2020 | Hiroshima et al. |
| 2020/0129322 A1 | 4/2020 | Leuckel |
| 2020/0171217 A9 | 6/2020 | Braga et al. |
| 2020/0179177 A1 | 6/2020 | Erdem et al. |
| 2020/0206015 A1 | 7/2020 | Langer |
| 2020/0206039 A1 | 7/2020 | Mclain |
| 2020/0214910 A1 | 7/2020 | Varona et al. |
| 2020/0216898 A1 | 7/2020 | Hubbell |
| 2020/0216989 A1 | 7/2020 | Kinugasa et al. |
| 2020/0229964 A1 | 7/2020 | Staali et al. |
| 2020/0231343 A1 | 7/2020 | Freedman et al. |
| 2020/0232841 A1 | 7/2020 | Satish et al. |
| 2020/0246172 A1 | 8/2020 | Ho |
| 2020/0246203 A1 | 8/2020 | Tulk et al. |
| 2020/0255189 A1 | 8/2020 | Liu |
| 2020/0261280 A1 | 8/2020 | Heyman |
| 2020/0276046 A1 | 9/2020 | Staali et al. |
| 2020/0306075 A1 | 10/2020 | Newton et al. |
| 2020/0315837 A1 | 10/2020 | Radl et al. |
| 2020/0315838 A1 | 10/2020 | Eckert |
| 2020/0315872 A1 | 10/2020 | Viens et al. |
| 2020/0315874 A1 | 10/2020 | Viens et al. |
| 2020/0331672 A1 | 10/2020 | Bertram et al. |
| 2020/0345332 A1 | 11/2020 | Duval |
| 2020/0353135 A1 | 11/2020 | Gregory et al. |
| 2020/0367677 A1 | 11/2020 | Silsby et al. |
| 2020/0369444 A1 | 11/2020 | Silsby et al. |
| 2020/0375781 A1 | 12/2020 | Staali et al. |
| 2020/0375810 A1 | 12/2020 | Carlin et al. |

(56) References Cited

U.S. PATENT DOCUMENTS

| | | |
|---|---|---|
| 2020/0385179 A1 | 12/2020 | Mccourt |
| 2020/0390591 A1 | 12/2020 | Glithero et al. |
| 2020/0390592 A1 | 12/2020 | Merrill |
| 2020/0405521 A1 | 12/2020 | Glasroe |
| 2021/0008771 A1 | 1/2021 | Huber et al. |
| 2021/0009323 A1 | 1/2021 | Markarian et al. |
| 2021/0020072 A1 | 1/2021 | Moehring et al. |
| 2021/0023279 A1 | 1/2021 | Radl et al. |
| 2021/0059853 A1 | 3/2021 | Davis et al. |
| 2021/0061523 A1 | 3/2021 | Bytheway |
| 2021/0069005 A1 | 3/2021 | Sanchez et al. |
| 2021/0069008 A1 | 3/2021 | Blabas et al. |
| 2021/0069009 A1 | 3/2021 | Im |
| 2021/0069030 A1 | 3/2021 | Nishikawa et al. |
| 2021/0077993 A1 | 3/2021 | Nazareth et al. |
| 2021/0113749 A1 | 4/2021 | Radl et al. |
| 2021/0121318 A1 | 4/2021 | Pinlac |
| 2021/0137724 A1 | 5/2021 | Ecklund et al. |
| 2021/0138190 A1 | 5/2021 | Erbey et al. |
| 2021/0154055 A1 | 5/2021 | Villarreal |
| 2021/0170079 A1 | 6/2021 | Radl et al. |
| 2021/0178390 A1 | 6/2021 | Oueslati et al. |
| 2021/0186742 A1 | 6/2021 | Newton et al. |
| 2021/0212865 A1 | 7/2021 | Wallajapet et al. |
| 2021/0220162 A1 | 7/2021 | Jamison |
| 2021/0220163 A1 | 7/2021 | Mayrand |
| 2021/0228400 A1 | 7/2021 | Glithero |
| 2021/0228401 A1 | 7/2021 | Becker et al. |
| 2021/0228795 A1 | 7/2021 | Hughett et al. |
| 2021/0229877 A1 | 7/2021 | Ragias et al. |
| 2021/0236323 A1 | 8/2021 | Austermann et al. |
| 2021/0236324 A1 | 8/2021 | Sweeney |
| 2021/0251814 A1 | 8/2021 | Jönegren et al. |
| 2021/0267787 A1 | 9/2021 | Nazemi |
| 2021/0275343 A1 | 9/2021 | Sanchez et al. |
| 2021/0275344 A1 | 9/2021 | Wing |
| 2021/0290454 A1 | 9/2021 | Yamada |
| 2021/0315727 A1 | 10/2021 | Jiang |
| 2021/0353450 A1 | 11/2021 | Sharma et al. |
| 2021/0361469 A1 | 11/2021 | Liu et al. |
| 2021/0369495 A1 | 12/2021 | Cheng et al. |
| 2021/0386925 A1 | 12/2021 | Hartwell et al. |
| 2021/0393433 A1 | 12/2021 | Godinez et al. |
| 2022/0023091 A1 | 1/2022 | Ecklund et al. |
| 2022/0031523 A1 | 2/2022 | Pierpoint |
| 2022/0039995 A1 | 2/2022 | Johannes et al. |
| 2022/0047410 A1 | 2/2022 | Walthall |
| 2022/0062027 A1 | 3/2022 | Mitchell et al. |
| 2022/0062028 A1 | 3/2022 | Mitchell et al. |
| 2022/0062029 A1 | 3/2022 | Johannes et al. |
| 2022/0066825 A1 | 3/2022 | Saraf et al. |
| 2022/0071811 A1 | 3/2022 | Cheng et al. |
| 2022/0071826 A1 | 3/2022 | Kulkarni et al. |
| 2022/0104965 A1 | 4/2022 | Vaninetti et al. |
| 2022/0104976 A1 | 4/2022 | Hoeger et al. |
| 2022/0104981 A1 | 4/2022 | Jones |
| 2022/0117773 A1 | 4/2022 | Davis et al. |
| 2022/0117774 A1 | 4/2022 | Meyer et al. |
| 2022/0117775 A1 | 4/2022 | Jones et al. |
| 2022/0133524 A1 | 5/2022 | Davis |
| 2022/0151817 A1 | 5/2022 | Mann |
| 2022/0160949 A1 | 5/2022 | Simiele et al. |
| 2022/0168159 A1 | 6/2022 | Triado et al. |
| 2022/0193312 A1 | 6/2022 | Lee et al. |
| 2022/0211536 A1 | 7/2022 | Johannes et al. |
| 2022/0218510 A1 | 7/2022 | Metzger et al. |
| 2022/0229053 A1 | 7/2022 | Levin et al. |
| 2022/0241106 A1 | 8/2022 | Johannes et al. |
| 2022/0247407 A1 | 8/2022 | Yamamoto et al. |
| 2022/0248836 A1 | 8/2022 | Cagle et al. |
| 2022/0257407 A1 | 8/2022 | Johannes et al. |
| 2022/0265460 A1 | 8/2022 | Coker |
| 2022/0265462 A1 | 8/2022 | Alder et al. |
| 2022/0270711 A1 | 8/2022 | Feala et al. |
| 2022/0273482 A1 | 9/2022 | Johannes et al. |
| 2022/0280357 A1 | 9/2022 | Jagannathan et al. |
| 2022/0287689 A1 | 9/2022 | Johannes |
| 2022/0287867 A1 | 9/2022 | Jones et al. |
| 2022/0287868 A1 | 9/2022 | Garvey et al. |
| 2022/0296408 A1 | 9/2022 | Evans et al. |
| 2022/0305191 A1 | 9/2022 | Joseph et al. |
| 2022/0313222 A1 | 10/2022 | Austermann et al. |
| 2022/0313474 A1 | 10/2022 | Kriscovich et al. |
| 2022/0331170 A1 | 10/2022 | Erdem et al. |
| 2022/0339024 A1 | 10/2022 | Johannes et al. |
| 2022/0354685 A1 | 11/2022 | Davis et al. |
| 2022/0362049 A1 | 11/2022 | Austermann et al. |
| 2022/0370231 A1 | 11/2022 | Wang et al. |
| 2022/0370234 A1 | 11/2022 | Hughett et al. |
| 2022/0370235 A1 | 11/2022 | Johannes et al. |
| 2022/0370237 A1 | 11/2022 | Parmar et al. |
| 2022/0387001 A1 | 12/2022 | Askenazi et al. |
| 2022/0395390 A1 | 12/2022 | Brooks |
| 2022/0395391 A1 | 12/2022 | Saunders et al. |
| 2022/0409422 A1 | 12/2022 | Schneider et al. |
| 2023/0018845 A1 | 1/2023 | Lee |
| 2023/0020563 A1 | 1/2023 | Sharma et al. |
| 2023/0031640 A1 | 2/2023 | Hughett et al. |
| 2023/0037159 A1 | 2/2023 | Brennan et al. |
| 2023/0049924 A1 | 2/2023 | Johannes et al. |
| 2023/0052238 A1 | 2/2023 | Oluwasogo |
| 2023/0062944 A1 | 3/2023 | Vollenberg et al. |
| 2023/0062994 A1 | 3/2023 | Ecklund et al. |
| 2023/0070347 A1 | 3/2023 | Watson et al. |
| 2023/0073708 A1 | 3/2023 | Xu et al. |
| 2023/0089032 A1 | 3/2023 | Hughett et al. |
| 2023/0099821 A1 | 3/2023 | Radl et al. |
| 2023/0099991 A1 | 3/2023 | Bianchi et al. |
| 2023/0105001 A1 | 4/2023 | Whittome et al. |
| 2023/0110577 A1 | 4/2023 | Choi |
| 2023/0138269 A1 | 5/2023 | Abdelal et al. |
| 2023/0145365 A1 | 5/2023 | Martin et al. |
| 2023/0155253 A1 | 5/2023 | Yin et al. |
| 2023/0210504 A1 | 7/2023 | Kuroda et al. |
| 2023/0210685 A1 | 7/2023 | Fallows et al. |
| 2023/0218426 A1 | 7/2023 | Hughett |
| 2023/0240884 A1 | 8/2023 | Davis et al. |
| 2023/0248562 A1 | 8/2023 | Sanchez et al. |
| 2023/0248564 A1 | 8/2023 | Mann et al. |
| 2023/0255812 A1 | 8/2023 | Sanchez et al. |
| 2023/0255813 A1 | 8/2023 | Sanchez et al. |
| 2023/0255815 A1 | 8/2023 | Newton |
| 2023/0263650 A1 | 8/2023 | Sanchez et al. |
| 2023/0263655 A1 | 8/2023 | Johannes et al. |
| 2023/0277362 A1 | 9/2023 | Davis et al. |
| 2023/0285178 A1 | 9/2023 | Sanchez et al. |
| 2023/0293339 A1 | 9/2023 | James |
| 2023/0301846 A1 | 9/2023 | Greenwood |
| 2023/0355423 A1 | 11/2023 | Stevenson et al. |
| 2023/0404791 A1 | 12/2023 | Ecklund et al. |
| 2024/0008444 A1 | 1/2024 | Su et al. |
| 2024/0009023 A1 | 1/2024 | Johannes et al. |
| 2024/0024170 A1 | 1/2024 | Scott |
| 2024/0041638 A1 | 2/2024 | Johannes et al. |
| 2024/0058161 A1 | 2/2024 | Ulreich et al. |
| 2024/0065881 A1 | 2/2024 | Kuroda et al. |
| 2024/0099874 A1 | 3/2024 | Sanchez et al. |
| 2024/0110318 A1 | 4/2024 | Bendt et al. |
| 2024/0123134 A1 | 4/2024 | Kharkar et al. |
| 2024/0148539 A1 | 5/2024 | Austermann et al. |
| 2024/0261131 A1 | 8/2024 | Garvey et al. |

FOREIGN PATENT DOCUMENTS

| | | |
|---|---|---|
| CA | 2165286 C | 9/1999 |
| CA | 2354132 A1 | 6/2000 |
| CA | 2359091 C | 9/2003 |
| CA | 2488867 C | 8/2007 |
| CA | 3050918 A1 | 8/2018 |
| CA | 3098571 A1 | 11/2019 |
| CN | 2269203 Y | 12/1997 |
| CN | 1332620 A | 1/2002 |
| CN | 1434693 A | 8/2003 |
| CN | 1533755 A | 10/2004 |

(56) References Cited

FOREIGN PATENT DOCUMENTS

| | | |
|---|---|---|
| CN | 1602825 A | 4/2005 |
| CN | 1720888 A | 1/2006 |
| CN | 2936204 Y | 8/2007 |
| CN | 101262836 A | 9/2008 |
| CN | 101522148 A | 9/2009 |
| CN | 102159159 A | 8/2011 |
| CN | 202184840 U | 4/2012 |
| CN | 102481441 A | 5/2012 |
| CN | 202463712 U | 10/2012 |
| CN | 202950810 U | 5/2013 |
| CN | 103533968 A | 1/2014 |
| CN | 103717180 A | 4/2014 |
| CN | 204562697 U | 8/2015 |
| CN | 105411783 A | 3/2016 |
| CN | 105451693 A | 3/2016 |
| CN | 105534632 A | 5/2016 |
| CN | 106132360 A | 11/2016 |
| CN | 205849719 U | 1/2017 |
| CN | 205924282 U | 2/2017 |
| CN | 106726089 A | 5/2017 |
| CN | 107847384 A | 3/2018 |
| CN | 107920912 A | 4/2018 |
| CN | 108420590 A | 8/2018 |
| CN | 209285902 U | 8/2019 |
| CN | 110381883 A | 10/2019 |
| CN | 211198839 U | 8/2020 |
| CN | 111991136 A | 11/2020 |
| CN | 112022488 A | 12/2020 |
| CN | 212234893 U | 12/2020 |
| CN | 212466312 U | 2/2021 |
| CN | 112566550 A | 3/2021 |
| CN | 112603184 A | 4/2021 |
| CN | 114007493 A | 2/2022 |
| CN | 114375187 A | 4/2022 |
| CN | 116096332 A | 5/2023 |
| DE | 79818 C | 10/1893 |
| DE | 1516466 A1 | 6/1969 |
| DE | 2721330 A1 | 11/1977 |
| DE | 2742298 A1 | 3/1978 |
| DE | 9407554.9 U1 | 5/1995 |
| DE | 4443710 A1 | 6/1995 |
| DE | 4416094 A1 | 11/1995 |
| DE | 4236097 C2 | 10/1996 |
| DE | 19619597 A1 | 11/1997 |
| DE | 102005037762 B3 | 9/2006 |
| DE | 102011103783 A1 | 12/2012 |
| DE | 102012112818 A1 | 6/2014 |
| DE | 202015104597 U1 | 7/2016 |
| DE | 102020121462 B3 | 1/2022 |
| DK | 9600118 | 11/1996 |
| EP | 0032138 A2 | 7/1981 |
| EP | 0066070 B1 | 12/1982 |
| EP | 0068712 A1 | 1/1983 |
| EP | 0140470 A1 | 5/1985 |
| EP | 0140471 B1 | 5/1988 |
| EP | 0274753 A2 | 7/1988 |
| EP | 0119143 B1 | 11/1988 |
| EP | 0483592 A1 | 5/1992 |
| EP | 0610638 A1 | 8/1994 |
| EP | 0613355 A1 | 9/1994 |
| EP | 0613355 B1 | 1/1997 |
| EP | 0787472 A1 | 8/1997 |
| EP | 0966936 A1 | 12/1999 |
| EP | 0987293 A1 | 3/2000 |
| EP | 1063953 A1 | 1/2001 |
| EP | 0653928 B1 | 10/2002 |
| EP | 1332738 A1 | 8/2003 |
| EP | 1382318 A1 | 1/2004 |
| EP | 1089684 B1 | 10/2004 |
| EP | 1616542 A1 | 1/2006 |
| EP | 1382318 B1 | 5/2006 |
| EP | 1063953 B1 | 1/2007 |
| EP | 1658831 B1 | 1/2008 |
| EP | 1872752 A1 | 1/2008 |
| EP | 2180907 A1 | 5/2010 |
| EP | 2380532 A1 | 10/2011 |
| EP | 2389908 A1 | 11/2011 |
| EP | 2601916 A1 | 6/2013 |
| EP | 2676643 A1 | 12/2013 |
| EP | 2997950 A2 | 3/2016 |
| EP | 2879534 B1 | 3/2017 |
| EP | 3424471 A1 | 1/2019 |
| EP | 3169292 B1 | 11/2019 |
| EP | 3753492 A1 | 12/2020 |
| EP | 3788992 A1 | 3/2021 |
| EP | 3576689 B1 | 3/2022 |
| EP | 3752110 B1 | 3/2022 |
| EP | 3787570 B1 | 3/2022 |
| EP | 4025163 A1 | 7/2022 |
| EP | 3463180 B1 | 3/2023 |
| EP | 3569205 B1 | 6/2023 |
| EP | 4382082 A2 | 6/2024 |
| EP | 4445881 A2 | 10/2024 |
| EP | 4464288 A2 | 11/2024 |
| GB | 871820 A | 7/1961 |
| GB | 1011517 A | 12/1965 |
| GB | 1467144 A | 3/1977 |
| GB | 2106395 A | 4/1983 |
| GB | 2106784 A | 4/1983 |
| GB | 2148126 A | 5/1985 |
| GB | 2171315 A | 8/1986 |
| GB | 2181953 A | 5/1987 |
| GB | 2148126 B | 7/1987 |
| GB | 2191095 A | 12/1987 |
| GB | 2199750 A | 7/1988 |
| GB | 2260907 A | 5/1993 |
| GB | 2462267 A | 2/2010 |
| GB | 2469496 A | 10/2010 |
| GB | 2490327 A | 10/2012 |
| GB | 2507318 A | 4/2014 |
| GB | 2612752 A | 5/2023 |
| IT | 201800009129 A1 | 4/2020 |
| JP | S498638 U | 1/1974 |
| JP | S5410596 A | 1/1979 |
| JP | S5410596 Y2 | 5/1979 |
| JP | S54155729 U | 10/1979 |
| JP | S55155618 A | 12/1980 |
| JP | S56152629 U | 11/1981 |
| JP | S57142534 U | 9/1982 |
| JP | S5888596 U | 6/1983 |
| JP | S58188016 U | 12/1983 |
| JP | S63107780 U | 7/1988 |
| JP | H0267530 A | 3/1990 |
| JP | H02103871 A | 4/1990 |
| JP | H02131422 A | 5/1990 |
| JP | H02131422 U | 11/1990 |
| JP | H0460220 A | 2/1992 |
| JP | H05123349 A | 5/1993 |
| JP | H05123350 A | 5/1993 |
| JP | H0626264 U | 4/1994 |
| JP | 3087938 B2 | 10/1995 |
| JP | H085630 A | 1/1996 |
| JP | H1040141 A | 2/1998 |
| JP | H10225430 A | 8/1998 |
| JP | H11113946 A | 4/1999 |
| JP | H11290365 A | 10/1999 |
| JP | 2000116690 A | 4/2000 |
| JP | 2000185068 A | 7/2000 |
| JP | 2000225139 A | 8/2000 |
| JP | 2001054531 A | 2/2001 |
| JP | 2001070331 A | 3/2001 |
| JP | 2001224616 A | 8/2001 |
| JP | 2001276107 A | 10/2001 |
| JP | 2001276108 A | 10/2001 |
| JP | 2002028173 A | 1/2002 |
| JP | 2003038563 A | 2/2003 |
| JP | 2003505152 A | 2/2003 |
| JP | 2003126242 A | 5/2003 |
| JP | 2003180722 A | 7/2003 |
| JP | 2003528691 A | 9/2003 |
| JP | 2004057578 A | 2/2004 |
| JP | 2004130056 A | 4/2004 |
| JP | 2004267530 A | 9/2004 |
| JP | 2005052219 A | 3/2005 |

(56) References Cited

FOREIGN PATENT DOCUMENTS

| | | | |
|---|---|---|---|
| JP | 2005066011 A | 3/2005 |
| JP | 2005066325 A | 3/2005 |
| JP | 2005102978 A | 4/2005 |
| JP | 2005518237 A | 6/2005 |
| JP | 3749097 B2 | 12/2005 |
| JP | 2006026108 A | 2/2006 |
| JP | 3123547 B2 | 6/2006 |
| JP | 2006136492 A | 6/2006 |
| JP | 2006204868 A | 8/2006 |
| JP | 2007044494 A | 2/2007 |
| JP | 3132659 B2 | 5/2007 |
| JP | 2007209687 A | 8/2007 |
| JP | 2007259898 A | 10/2007 |
| JP | 4039641 B2 | 11/2007 |
| JP | 2008005975 A | 1/2008 |
| JP | 2009509570 A | 3/2009 |
| JP | 2009165887 A | 7/2009 |
| JP | 2009525776 A | 7/2009 |
| JP | 2010504150 A | 2/2010 |
| JP | 2010058795 A | 3/2010 |
| JP | 2010081981 A | 4/2010 |
| JP | 4640772 B2 | 12/2010 |
| JP | 2010536439 A | 12/2010 |
| JP | 2011500225 A | 1/2011 |
| JP | 2011030962 A | 2/2011 |
| JP | 4747166 B2 | 5/2011 |
| JP | 2011087823 A | 5/2011 |
| JP | 4801218 B1 | 8/2011 |
| JP | 2011218130 A | 11/2011 |
| JP | 2011224070 A | 11/2011 |
| JP | 3175719 U | 4/2012 |
| JP | 2012523869 A | 10/2012 |
| JP | 2013238608 A | 11/2013 |
| JP | 2014521960 A | 8/2014 |
| JP | 2015092945 A | 5/2015 |
| JP | 2015513678 A | 5/2015 |
| JP | 3198994 B2 | 7/2015 |
| JP | 2015221390 A | 12/2015 |
| JP | 2016521191 A | 7/2016 |
| JP | 2017014698 A | 1/2017 |
| JP | 2017512603 A | 5/2017 |
| JP | 2017201272 A | 11/2017 |
| JP | 2019076342 A | 5/2019 |
| JP | 2019525811 A | 9/2019 |
| JP | 2019170942 A | 10/2019 |
| JP | 2019533492 A | 11/2019 |
| JP | 2020520775 A | 7/2020 |
| JP | 2021120686 A | 8/2021 |
| JP | 2021522009 A | 8/2021 |
| JP | 2021522013 A | 8/2021 |
| JP | 7129493 B2 | 8/2022 |
| JP | 2023532132 A | 7/2023 |
| KR | 200290061 Y1 | 9/2002 |
| KR | 20030047451 A | 6/2003 |
| KR | 20080005516 A | 1/2008 |
| KR | 20090104426 A | 10/2009 |
| KR | 20140039485 A | 4/2014 |
| KR | 101432639 B1 | 8/2014 |
| KR | 20180106659 A | 10/2018 |
| KR | 20180108774 A | 10/2018 |
| PT | 2068717 E | 6/2013 |
| SE | 505542 C2 | 9/1997 |
| WO | 8101957 A1 | 7/1981 |
| WO | 8804558 A1 | 6/1988 |
| WO | 9104714 A2 | 4/1991 |
| WO | 9104714 A3 | 6/1991 |
| WO | 9220299 A3 | 2/1993 |
| WO | 9303690 A1 | 3/1993 |
| WO | 9307839 A1 | 4/1993 |
| WO | 9309736 A2 | 5/1993 |
| WO | 9309736 A3 | 6/1993 |
| WO | 9514448 A2 | 6/1995 |
| WO | 9600096 A1 | 1/1996 |
| WO | 9634636 A1 | 11/1996 |
| WO | 9817211 A1 | 4/1998 |
| WO | 9830336 A1 | 7/1998 |
| WO | 0000112 A1 | 1/2000 |
| WO | 0000113 A1 | 1/2000 |
| WO | 0025651 A1 | 5/2000 |
| WO | 0033773 A1 | 6/2000 |
| WO | 0057784 A1 | 10/2000 |
| WO | 0069377 A1 | 11/2000 |
| WO | 0079497 A1 | 12/2000 |
| WO | 0145618 A1 | 6/2001 |
| WO | 0145621 A1 | 6/2001 |
| WO | 02094160 A1 | 11/2002 |
| WO | 03013967 A1 | 2/2003 |
| WO | 03024824 A1 | 3/2003 |
| WO | 03055423 A1 | 7/2003 |
| WO | 03071931 A2 | 9/2003 |
| WO | 03079942 A1 | 10/2003 |
| WO | 03071931 A3 | 2/2004 |
| WO | 2004019836 A1 | 3/2004 |
| WO | 2004024046 A1 | 3/2004 |
| WO | 2004026195 A1 | 4/2004 |
| WO | 2005051252 A1 | 6/2005 |
| WO | 2005074571 A3 | 9/2005 |
| WO | 2005089687 A2 | 9/2005 |
| WO | 2005107661 A2 | 11/2005 |
| WO | 2006021220 A1 | 3/2006 |
| WO | 2006037140 A2 | 4/2006 |
| WO | 2007005851 A2 | 1/2007 |
| WO | 2007007845 A1 | 1/2007 |
| WO | 2007042823 A2 | 4/2007 |
| WO | 2007055651 A1 | 5/2007 |
| WO | 2006098950 A3 | 11/2007 |
| WO | 2007134608 A2 | 11/2007 |
| WO | 2007128156 A3 | 2/2008 |
| WO | 2008026106 A2 | 3/2008 |
| WO | 2008078117 A1 | 7/2008 |
| WO | 2008104019 A1 | 9/2008 |
| WO | 2008141471 A1 | 11/2008 |
| WO | 2009004368 A1 | 1/2009 |
| WO | 2009004369 A1 | 1/2009 |
| WO | 2009052496 A1 | 4/2009 |
| WO | 2009052502 A1 | 4/2009 |
| WO | 2009007702 A4 | 7/2009 |
| WO | 2009101738 A1 | 8/2009 |
| WO | 2010058192 A1 | 5/2010 |
| WO | 2010030122 A3 | 7/2010 |
| WO | 2010101915 A3 | 1/2011 |
| WO | 2011018132 A1 | 2/2011 |
| WO | 2011018133 A1 | 2/2011 |
| WO | 2011024864 A1 | 3/2011 |
| WO | 2011054118 A1 | 5/2011 |
| WO | 2011079132 A1 | 6/2011 |
| WO | 2011107972 A1 | 9/2011 |
| WO | 2011108972 A1 | 9/2011 |
| WO | 2011117292 A1 | 9/2011 |
| WO | 2011123219 A1 | 10/2011 |
| WO | 2011132043 A1 | 10/2011 |
| WO | 2012012908 A1 | 2/2012 |
| WO | 2012020506 A1 | 2/2012 |
| WO | 2012065274 A1 | 5/2012 |
| WO | 2012097462 A1 | 7/2012 |
| WO | 2012098796 A1 | 7/2012 |
| WO | 2012101288 A1 | 8/2012 |
| WO | 2012175916 A1 | 12/2012 |
| WO | 2013018435 A1 | 2/2013 |
| WO | 2013033429 A1 | 3/2013 |
| WO | 2013055434 A1 | 4/2013 |
| WO | 2013082397 A1 | 6/2013 |
| WO | 2013103291 A2 | 7/2013 |
| WO | 2013131109 A1 | 9/2013 |
| WO | 2013167478 A1 | 11/2013 |
| WO | 2013177716 A1 | 12/2013 |
| WO | 2014041534 A1 | 3/2014 |
| WO | 2014046420 A1 | 3/2014 |
| WO | 2014118518 A1 | 8/2014 |
| WO | 2014160852 A1 | 10/2014 |
| WO | 2015023599 A1 | 2/2015 |
| WO | 2015052348 A1 | 4/2015 |
| WO | 2015068384 A1 | 5/2015 |
| WO | 2015169403 A1 | 11/2015 |

(56) References Cited

FOREIGN PATENT DOCUMENTS

| | | | |
|---|---|---|---|
| WO | 2015170307 | A1 | 11/2015 |
| WO | 2015197462 | A1 | 12/2015 |
| WO | 2016051385 | A1 | 4/2016 |
| WO | 2016055989 | A1 | 4/2016 |
| WO | 2016071894 | A1 | 5/2016 |
| WO | 2016103242 | A1 | 6/2016 |
| WO | 2016116915 | A1 | 7/2016 |
| WO | 2016124203 | A1 | 8/2016 |
| WO | 2016139448 | A1 | 9/2016 |
| WO | 2016166562 | A1 | 10/2016 |
| WO | 2016167535 | A1 | 10/2016 |
| WO | 2016191574 | A1 | 12/2016 |
| WO | 2016200088 | A1 | 12/2016 |
| WO | 2016200361 | A1 | 12/2016 |
| WO | 2016204731 | A1 | 12/2016 |
| WO | 2017001532 | A2 | 1/2017 |
| WO | 2017001846 | A1 | 1/2017 |
| WO | 2017075226 | A1 | 5/2017 |
| WO | 2017152198 | A1 | 9/2017 |
| WO | 2017153357 | A1 | 9/2017 |
| WO | 2017162559 | A1 | 9/2017 |
| WO | 2017205446 | A1 | 11/2017 |
| WO | 2017209779 | A1 | 12/2017 |
| WO | 2017210524 | A1 | 12/2017 |
| WO | 2018022414 | A1 | 2/2018 |
| WO | 2018044781 | A1 | 3/2018 |
| WO | 2018056953 | A1 | 3/2018 |
| WO | 2018090550 | A1 | 5/2018 |
| WO | 2018138513 | A1 | 8/2018 |
| WO | 2018144318 | A1 | 8/2018 |
| WO | 2018144463 | A1 | 8/2018 |
| WO | 2018150263 | A1 | 8/2018 |
| WO | 2018150268 | A1 | 8/2018 |
| WO | 2018152156 | A1 | 8/2018 |
| WO | 2018183791 | A1 | 10/2018 |
| WO | 2018150267 | A3 | 11/2018 |
| WO | 2018235026 | A1 | 12/2018 |
| WO | 2018235065 | A1 | 12/2018 |
| WO | 2019004404 | A1 | 1/2019 |
| WO | 2019041005 | A1 | 3/2019 |
| WO | 2019044217 | A1 | 3/2019 |
| WO | 2019044218 | A1 | 3/2019 |
| WO | 2019044219 | A1 | 3/2019 |
| WO | 2019050959 | A1 | 3/2019 |
| WO | 2019065541 | A1 | 4/2019 |
| WO | 2019096845 | A1 | 5/2019 |
| WO | 2019150385 | A1 | 8/2019 |
| WO | 2019161094 | A1 | 8/2019 |
| WO | 2019188566 | A1 | 10/2019 |
| WO | 2019190593 | A1 | 10/2019 |
| WO | 2019212949 | A1 | 11/2019 |
| WO | 2019212950 | A1 | 11/2019 |
| WO | 2019212951 | A1 | 11/2019 |
| WO | 2019212952 | A1 | 11/2019 |
| WO | 2019212954 | A1 | 11/2019 |
| WO | 2019212955 | A1 | 11/2019 |
| WO | 2019212956 | A1 | 11/2019 |
| WO | 2019214787 | A1 | 11/2019 |
| WO | 2019214788 | A1 | 11/2019 |
| WO | 2019226826 | A1 | 11/2019 |
| WO | 2019239433 | A1 | 12/2019 |
| WO | 2020000994 | A1 | 1/2020 |
| WO | 2020020618 | A1 | 1/2020 |
| WO | 2020038822 | A1 | 2/2020 |
| WO | 2020088409 | A1 | 5/2020 |
| WO | 2020049394 | A3 | 6/2020 |
| WO | 2020120657 | A1 | 6/2020 |
| WO | 2020152575 | A1 | 7/2020 |
| WO | 2020182923 | A1 | 9/2020 |
| WO | 2020204967 | A1 | 10/2020 |
| WO | 2020205939 | A1 | 10/2020 |
| WO | 2020209898 | A1 | 10/2020 |
| WO | 2020242790 | A1 | 12/2020 |
| WO | 2020251893 | A1 | 12/2020 |
| WO | 2020256865 | A1 | 12/2020 |
| WO | 2021007144 | A1 | 1/2021 |
| WO | 2021007345 | A1 | 1/2021 |
| WO | 2021010844 | A1 | 1/2021 |
| WO | 2021016026 | A1 | 1/2021 |
| WO | 2021016300 | A1 | 1/2021 |
| WO | 2021025919 | A1 | 2/2021 |
| WO | 2021034886 | A1 | 2/2021 |
| WO | 2021041123 | A1 | 3/2021 |
| WO | 2021046501 | A1 | 3/2021 |
| WO | 2021086868 | A1 | 5/2021 |
| WO | 2021094352 | A1 | 5/2021 |
| WO | 2021094639 | A1 | 5/2021 |
| WO | 2021097067 | A1 | 5/2021 |
| WO | 2021102296 | A1 | 5/2021 |
| WO | 2021107025 | A1 | 6/2021 |
| WO | 2021138411 | A1 | 7/2021 |
| WO | 2021138414 | A1 | 7/2021 |
| WO | 2021154686 | A1 | 8/2021 |
| WO | 2021155206 | A1 | 8/2021 |
| WO | 2021170075 | A1 | 9/2021 |
| WO | 2021173436 | A1 | 9/2021 |
| WO | 2021188817 | A1 | 9/2021 |
| WO | 2021195384 | A1 | 9/2021 |
| WO | 2021205995 | A1 | 10/2021 |
| WO | 2021207621 | A1 | 10/2021 |
| WO | 2021211568 | A1 | 10/2021 |
| WO | 2021211801 | A1 | 10/2021 |
| WO | 2021211914 | A1 | 10/2021 |
| WO | 2021216419 | A1 | 10/2021 |
| WO | 2021216422 | A1 | 10/2021 |
| WO | 2021231532 | A1 | 11/2021 |
| WO | 2021247523 | A1 | 12/2021 |
| WO | 2021257202 | A1 | 12/2021 |
| WO | 2022006256 | A1 | 1/2022 |
| WO | 2022031943 | A1 | 2/2022 |
| WO | 2022035745 | A1 | 2/2022 |
| WO | 2022051360 | A1 | 3/2022 |
| WO | 2022054613 | A1 | 3/2022 |
| WO | 2022066704 | A1 | 3/2022 |
| WO | 2022067392 | A1 | 4/2022 |
| WO | 2022069950 | A1 | 4/2022 |
| WO | 2022071429 | A1 | 4/2022 |
| WO | 2022076322 | A1 | 4/2022 |
| WO | 2022076427 | A2 | 4/2022 |
| WO | 2022086898 | A1 | 4/2022 |
| WO | 2022090199 | A1 | 5/2022 |
| WO | 2022098536 | A1 | 5/2022 |
| WO | 2022099087 | A1 | 5/2022 |
| WO | 2022101999 | A1 | 5/2022 |
| WO | 2022115692 | A1 | 6/2022 |
| WO | 2022125685 | A1 | 6/2022 |
| WO | 2022140545 | A1 | 6/2022 |
| WO | 2022145231 | A1 | 7/2022 |
| WO | 2022150360 | A1 | 7/2022 |
| WO | 2022150463 | A1 | 7/2022 |
| WO | 2022159392 | A1 | 7/2022 |
| WO | 2022170182 | A1 | 8/2022 |
| WO | 2022182385 | A1 | 9/2022 |
| WO | 2022187152 | A1 | 9/2022 |
| WO | 2022192188 | A1 | 9/2022 |
| WO | 2022192347 | A1 | 9/2022 |
| WO | 2022204000 | A1 | 9/2022 |
| WO | 2022216507 | A1 | 10/2022 |
| WO | 2022216776 | A1 | 10/2022 |
| WO | 2022222030 | A1 | 10/2022 |
| WO | 2023286058 | A1 | 1/2023 |
| WO | 2023014639 | A1 | 2/2023 |
| WO | 2023014641 | A1 | 2/2023 |
| WO | 2023018475 | A2 | 2/2023 |
| WO | 2023023777 | A1 | 3/2023 |
| WO | 2023034139 | A1 | 3/2023 |
| WO | 2023034453 | A1 | 3/2023 |
| WO | 2023038945 | A1 | 3/2023 |
| WO | 2023038950 | A1 | 3/2023 |
| WO | 2023049109 | A1 | 3/2023 |
| WO | 2023049175 | A1 | 3/2023 |
| WO | 2023086394 | A1 | 5/2023 |
| WO | 2023149884 | A1 | 8/2023 |
| WO | 2023149902 | A1 | 8/2023 |

(56) References Cited

FOREIGN PATENT DOCUMENTS

| WO | 2023149903 A1 | 8/2023 |
| WO | 2023154390 A1 | 8/2023 |
| WO | 2023191764 A1 | 10/2023 |
| WO | 2023244238 A1 | 12/2023 |
| WO | 2024058788 A1 | 3/2024 |

OTHER PUBLICATIONS

Advisory Action for U.S. Appl. No. 16/245,726 mailed Apr. 19, 2023.
Advisory Action for U.S. Appl. No. 16/369,676 mailed Mar. 24, 2023.
Advisory Action for U.S. Appl. No. 16/433,773 mailed Feb. 15, 2023.
Advisory Action for U.S. Appl. No. 16/452,258 mailed Oct. 26, 2022.
Advisory Action for U.S. Appl. No. 16/478,180 mailed Sep. 21, 2022.
Advisory Action for U.S. Appl. No. 16/478,180 mailed Sep. 7, 2023.
Advisory Action for U.S. Appl. No. 16/904,868 mailed Jun. 15, 2022.
Advisory Action for U.S. Appl. No. 16/905,400 mailed Feb. 16, 2022.
Advisory Action for U.S. Appl. No. 17/051,550 mailed Sep. 8, 2023.
Advisory Action for U.S. Appl. No. 17/444,792 mailed Aug. 25, 2023.
Advisory Action for U.S. Appl. No. 17/662,700 mailed Jan. 30, 2023.
Corrected Notice of Allowability for U.S. Appl. No. 17/330,657 mailed Dec. 9, 2021.
Final Office Action for U.S. Appl. No. 16/245,726 mailed Nov. 25, 2022.
Final Office Action for U.S. Appl. No. 16/369,676 mailed Aug. 31, 2023.
Final Office Action for U.S. Appl. No. 16/369,676 mailed Dec. 5, 2022.
Final Office Action for U.S. Appl. No. 16/433,773 mailed Oct. 25, 2022.
Final Office Action for U.S. Appl. No. 16/449,039 mailed Aug. 1, 2022.
Final Office Action for U.S. Appl. No. 16/452,145 mailed Mar. 25, 2022.
Final Office Action for U.S. Appl. No. 16/452,258 mailed Jun. 14, 2022.
Final Office Action for U.S. Appl. No. 16/478,180 mailed Jun. 22, 2022.
Final Office Action for U.S. Appl. No. 16/478,180 mailed May 31, 2023.
Final Office Action for U.S. Appl. No. 16/904,868 mailed Mar. 10, 2022.
Final Office Action for U.S. Appl. No. 16/905,400 mailed Dec. 9, 2021.
Final Office Action for U.S. Appl. No. 17/051,399 mailed Mar. 9, 2023.
Final Office Action for U.S. Appl. No. 17/051,550 mailed May 23, 2023.
Final Office Action for U.S. Appl. No. 17/051,585 mailed Jul. 27, 2023.
Final Office Action for U.S. Appl. No. 17/444,792 mailed Jun. 15, 2023.
Final Office Action for U.S. Appl. No. 17/448,811 mailed Aug. 3, 2023.
Final Office Action for U.S. Appl. No. 17/451,345 mailed May 3, 2023.
Final Office Action for U.S. Appl. No. 17/655,464 mailed Sep. 1, 2023.
Final Office Action for U.S. Appl. No. 17/662,700 mailed Sep. 30, 2022.
International Search Report and Written Opinion from International Application No. PCT/IB2021/057173 mailed Nov. 5, 2021.
International Search Report and Written Opinion from International Application No. PCT/US2020/057562 mailed Jan. 27, 2021.
International Search Report and Written Opinion from International Application No. PCT/US2021/026607 mailed Jul. 29, 2021.
International Search Report and Written Opinion from International Application No. PCT/US2021/039866 mailed Oct. 7, 2021.
International Search Report and Written Opinion from International Application No. PCT/US2021/044699 mailed Nov. 22, 2021.
International Search Report and Written Opinion from International Application No. PCT/US2021/045188 mailed Jan. 26, 2022.
International Search Report and Written Opinion from International Application No. PCT/US2021/047536 mailed Dec. 23, 2021.
International Search Report and Written Opinion from International Application No. PCT/US2021/048211 mailed Dec. 22, 2021.
International Search Report and Written Opinion from International Application No. PCT/US2021/048661 mailed Feb. 14, 2022.
International Search Report and Written Opinion from International Application No. PCT/US2021/049404 mailed Jan. 18, 2022.
International Search Report and Written Opinion from International Application No. PCT/US2021/051456 mailed Jan. 19, 2022.
International Search Report and Written Opinion from International Application No. PCT/US2021/053593 mailed Apr. 11, 2022.
International Search Report and Written Opinion from International Application No. PCT/US2021/055515 mailed Jan. 28, 2022.
International Search Report and Written Opinion from International Application No. PCT/US2021/056566 mailed Feb. 11, 2022.
International Search Report and Written Opinion from International Application No. PCT/US2021/060993 mailed Mar. 18, 2022.
International Search Report and Written Opinion from International Application No. PCT/US2021/062440 mailed Mar. 28, 2022.
International Search Report and Written Opinion from International Application No. PCT/US2022/011108 mailed Apr. 22, 2022.
International Search Report and Written Opinion from International Application No. PCT/US2022/011281 mailed Apr. 25, 2022.
International Search Report and Written Opinion from International Application No. PCT/US2022/011419 mailed Jun. 7, 2022.
International Search Report and Written Opinion from International Application No. PCT/US2022/011421 mailed Jun. 13, 2022.
International Search Report and Written Opinion from International Application No. PCT/US2022/012794 mailed May 3, 2022.
International Search Report and Written Opinion from International Application No. PCT/US2022/014285 mailed Sep. 28, 2022.
International Search Report and Written Opinion from International Application No. PCT/US2022/014749 mailed Sep. 28, 2022.
International Search Report and Written Opinion from International Application No. PCT/US2022/015026 mailed Oct. 31, 2022.
International Search Report and Written Opinion from International Application No. PCT/US2022/015045 mailed Sep. 9, 2022.
International Search Report and Written Opinion from International Application No. PCT/US2022/015073 mailed Sep. 8, 2022.
International Search Report and Written Opinion from International Application No. PCT/US2022/015418 mailed Nov. 11, 2022.
International Search Report and Written Opinion from International Application No. PCT/US2022/015420 mailed Nov. 18, 2022.
International Search Report and Written Opinion from International Application No. PCT/US2022/015471 mailed May 16, 2022.
International Search Report and Written Opinion from International Application No. PCT/US2022/015492 mailed Apr. 26, 2022.
International Search Report and Written Opinion from International Application No. PCT/US2022/015781 mailed May 6, 2022.
International Search Report and Written Opinion from International Application No. PCT/US2022/016942 mailed Jun. 8, 2022.
International Search Report and Written Opinion from International Application No. PCT/US2022/018159 mailed Dec. 12, 2022.
International Search Report and Written Opinion from International Application No. PCT/US2022/018170 mailed May 31, 2022.
International Search Report and Written Opinion from International Application No. PCT/US2022/019254 mailed Jun. 7, 2022.
International Search Report and Written Opinion from International Application No. PCT/US2022/019480 mailed Jun. 13, 2022.
International Search Report and Written Opinion from International Application No. PCT/US2022/021103 mailed Jun. 23, 2022.

(56) References Cited

OTHER PUBLICATIONS

International Search Report and Written Opinion from International Application No. PCT/US2022/022111 mailed Oct. 26, 2022.
International Search Report and Written Opinion from International Application No. PCT/US2022/023594 mailed Jul. 12, 2022.
International Search Report and Written Opinion from International Application No. PCT/US2022/026667 mailed Aug. 22, 2022.
International Search Report and Written Opinion from International Application No. PCT/US2022/030685 mailed Oct. 31, 2022.
International Search Report and Written Opinion from International Application No. PCT/US2022/031032 mailed Sep. 9, 2022.
International Search Report and Written Opinion from International Application No. PCT/US2022/032424 mailed Oct. 11, 2022.
International Search Report and Written Opinion from International Application No. PCT/US2022/034457 mailed Oct. 12, 2022.
International Search Report and Written Opinion from International Application No. PCT/US2022/034744 mailed Dec. 9, 2022.
International Search Report and Written Opinion from International Application No. PCT/US2022/039018 mailed Jan. 10, 2023.
International Search Report and Written Opinion from International Application No. PCT/US2022/039022 mailed Jan. 10, 2023.
International Search Report and Written Opinion from International Application No. PCT/US2022/039711 mailed Jan. 12, 2023.
International Search Report and Written Opinion from International Application No. PCT/US2022/039714 mailed Nov. 22, 2022.
International Search Report and Written Opinion from International Application No. PCT/US2022/041085 mailed Mar. 16, 2023.
International Search Report and Written Opinion from International Application No. PCT/US2022/041688 mailed Nov. 21, 2022.
International Search Report and Written Opinion from International Application No. PCT/US2022/042719 mailed Dec. 5, 2022.
International Search Report and Written Opinion from International Application No. PCT/US2022/042725 mailed Dec. 19, 2022.
International Search Report and Written Opinion from International Application No. PCT/US2022/043818 mailed Mar. 24, 2023.
International Search Report and Written Opinion from International Application No. PCT/US2022/044107 mailed Dec. 23, 2022.
International Search Report and Written Opinion from International Application No. PCT/US2022/044208 mailed May 8, 2023.
International Search Report and Written Opinion from International Application No. PCT/US2022/044212 mailed Jan. 20, 2023.
International Search Report and Written Opinion from International Application No. PCT/US2022/044243 mailed Feb. 24, 2023.
International Search Report and Written Opinion from International Application No. PCT/US2022/049300 mailed Jun. 6, 2023.
International Search Report and Written Opinion from International Application No. PCT/US2022/050909 mailed Jul. 24, 2023.
International Search Report and Written Opinion from International Application No. PCT/US2023/012696 mailed Jul. 6, 2023.
Issue Notification for U.S. Appl. No. 16/899,956 mailed Mar. 29, 2023.
Issue Notification for U.S. Appl. No. 16/905,400 mailed Nov. 30, 2022.
Issue Notification for U.S. Appl. No. 17/088,272 mailed Jun. 15, 2022.
Issue Notification for U.S. Appl. No. 17/330,657 mailed Jun. 22, 2022.
Non-Final Office Action for U.S. Appl. No. 16/245,726 mailed Jan. 21, 2022.
Non-Final Office Action for U.S. Appl. No. 16/369,676 mailed Mar. 31, 2022.
Non-Final Office Action for U.S. Appl. No. 16/433,773 mailed Apr. 11, 2023.
Non-Final Office Action for U.S. Appl. No. 16/433,773 mailed Apr. 21, 2022.
Non-Final Office Action for U.S. Appl. No. 16/449,039 mailed Apr. 27, 2023.
Non-Final Office Action for U.S. Appl. No. 16/452,145 mailed Mar. 28, 2023.

Non-Final Office Action for U.S. Appl. No. 16/452,258 mailed Apr. 26, 2023.
Non-Final Office Action for U.S. Appl. No. 16/478,180 mailed Dec. 20, 2022.
Non-Final Office Action for U.S. Appl. No. 16/904,868 mailed Mar. 15, 2023.
Non-Final Office Action for U.S. Appl. No. 16/905,400 mailed Apr. 27, 2022.
Non-Final Office Action for U.S. Appl. No. 17/051,399 mailed Aug. 18, 2023.
Non-Final Office Action for U.S. Appl. No. 17/051,550 mailed Dec. 15, 2022.
Non-Final Office Action for U.S. Appl. No. 17/051,585 mailed Mar. 29, 2023.
Non-Final Office Action for U.S. Appl. No. 17/179,116 mailed Mar. 24, 2023.
Non-Final Office Action for U.S. Appl. No. 17/326,980 mailed Jul. 11, 2023.
Non-Final Office Action for U.S. Appl. No. 17/444,792 mailed Feb. 10, 2023.
Non-Final Office Action for U.S. Appl. No. 17/446,256 mailed Apr. 13, 2023.
Non-Final Office Action for U.S. Appl. No. 17/446,654 mailed Sep. 8, 2023.
Non-Final Office Action for U.S. Appl. No. 17/448,811 mailed Mar. 1, 2023.
Non-Final Office Action for U.S. Appl. No. 17/450,864 mailed May 10, 2023.
Non-Final Office Action for U.S. Appl. No. 17/451,345 mailed Dec. 7, 2022.
Non-Final Office Action for U.S. Appl. No. 17/451,354 mailed May 3, 2023.
Non-Final Office Action for U.S. Appl. No. 17/453,260 mailed Mar. 14, 2023.
Non-Final Office Action for U.S. Appl. No. 17/501,591 mailed Apr. 25, 2023.
Non-Final Office Action for U.S. Appl. No. 17/646,771 mailed Jul. 5, 2023.
Non-Final Office Action for U.S. Appl. No. 17/653,137 mailed Apr. 7, 2023.
Non-Final Office Action for U.S. Appl. No. 17/655,464 mailed Mar. 14, 2023.
Non-Final Office Action for U.S. Appl. No. 17/661,090 mailed Jul. 6, 2023.
Non-Final Office Action for U.S. Appl. No. 17/662,700 mailed Jul. 22, 2022.
Non-Final Office Action for U.S. Appl. No. 17/663,330 mailed Jun. 29, 2023.
Non-Final Office Action for U.S. Appl. No. 17/664,487 mailed Jun. 8, 2023.
Non-Final Office Action for U.S. Appl. No. 18/139,523 mailed Aug. 17, 2023.
Non-Final Office Action for U.S. Appl. No. 29/741,751 mailed Jan. 18, 2022.
Notice of Allowance for U.S. Appl. No. 16/245,726 mailed Jul. 6, 2023.
Notice of Allowance for U.S. Appl. No. 16/449,039 mailed Dec. 15, 2022.
Notice of Allowance for U.S. Appl. No. 16/899,956 mailed Apr. 19, 2022.
Notice of Allowance for U.S. Appl. No. 16/899,956 mailed Aug. 10, 2022.
Notice of Allowance for U.S. Appl. No. 16/899,956 mailed Dec. 1, 2022.
Notice of Allowance for U.S. Appl. No. 16/899,956 mailed Dec. 29, 2021.
Notice of Allowance for U.S. Appl. No. 16/905,400 mailed Aug. 17, 2022.
Notice of Allowance for U.S. Appl. No. 17/051,554 mailed Jul. 6, 2023.
Notice of Allowance for U.S. Appl. No. 17/088,272 mailed Mar. 4, 2022.

(56) References Cited

OTHER PUBLICATIONS

Notice of Allowance for U.S. Appl. No. 17/088,272 mailed Nov. 24, 2021.
Notice of Allowance for U.S. Appl. No. 17/330,657 mailed Mar. 16, 2022.
Notice of Allowance for U.S. Appl. No. 17/330,657 mailed Nov. 26, 2021.
Notice of Allowance for U.S. Appl. No. 17/461,036 mailed Feb. 22, 2023.
Notice of Allowance for U.S. Appl. No. 17/461,036 mailed Jun. 30, 2023.
Notice of Allowance for U.S. Appl. No. 17/461,036 mailed Oct. 6, 2022.
Notice of Allowance for U.S. Appl. No. 17/662,700 mailed Jul. 28, 2023.
Notice of Allowance for U.S. Appl. No. 17/662,700 mailed Mar. 28, 2023.
Notice of Allowance for U.S. Appl. No. 17/663,046 mailed Jan. 30, 2023.
Notice of Allowance for U.S. Appl. No. 18/299,788 mailed Jul. 24, 2023.
Notice of Allowance for U.S. Appl. No. 29/741,751 mailed Jun. 9, 2022.
Restriction Requirement for U.S. Appl. No. 16/433,773 mailed Dec. 7, 2021.
Restriction Requirement for U.S. Appl. No. 17/326,980 mailed Mar. 20, 2023.
Restriction Requirement for U.S. Appl. No. 17/446,256 mailed Jan. 23, 2023.
Restriction Requirement for U.S. Appl. No. 17/646,771 mailed Apr. 6, 2023.
Restriction Requirement for U.S. Appl. No. 17/657,474 mailed Jun. 30, 2023.
Text Messages to Lorena Eckert Re Prototype PureWick Holder dated Apr. 16, 2022.
U.S. Appl. No. 15/384,196, filed Dec. 19, 2016.
U.S. Appl. No. 17/394,055, filed Aug. 4, 2021.
U.S. Appl. No. 17/453,260, filed Nov. 2, 2021.
U.S. Appl. No. 17/595,747, filed Nov. 23, 2021.
U.S. Appl. No. 17/597,408, filed Jan. 5, 2022.
U.S. Appl. No. 17/597,673, filed Jan. 18, 2022.
U.S. Appl. No. 17/614,173, filed Nov. 24, 2021.
U.S. Appl. No. 17/631,619, filed Jan. 31, 2022.
U.S. Appl. No. 17/646,771, filed Jan. 3, 2022.
U.S. Appl. No. 17/653,314, filed Mar. 3, 2022.
U.S. Appl. No. 17/653,920, filed Mar. 8, 2022.
U.S. Appl. No. 17/655,464, filed Mar. 18, 2022.
U.S. Appl. No. 17/657,474, filed Mar. 31, 2022.
U.S. Appl. No. 17/661,090, filed Apr. 28, 2022.
U.S. Appl. No. 17/662,700, filed May 10, 2022.
U.S. Appl. No. 17/663,046, filed May 12, 2022.
U.S. Appl. No. 17/664,487, filed May 23, 2022.
U.S. Appl. No. 17/664,914, filed May 25, 2022.
U.S. Appl. No. 17/749,340, filed May 20, 2022.
U.S. Appl. No. 17/754,736, filed Apr. 11, 2022.
U.S. Appl. No. 17/756,201, filed May 19, 2022.
U.S. Appl. No. 17/758,152, filed Jun. 29, 2022.
U.S. Appl. No. 17/758,316, filed Jul. 1, 2022.
U.S. Appl. No. 17/759,697, filed Jul. 28, 2022.
U.S. Appl. No. 17/878,268, filed Aug. 1, 2022.
U.S. Appl. No. 17/907,125, filed Sep. 23, 2022.
U.S. Appl. No. 17/912,147, filed Sep. 16, 2022.
U.S. Appl. No. 17/929,887, filed Sep. 6, 2022.
U.S. Appl. No. 17/930,238, filed Sep. 7, 2022.
U.S. Appl. No. 17/933,590, filed Sep. 20, 2022.
U.S. Appl. No. 17/996,064, filed Oct. 12, 2022.
U.S. Appl. No. 17/996,155, filed Oct. 13, 2022.
U.S. Appl. No. 17/996,253, filed Oct. 14, 2022.
U.S. Appl. No. 17/996,468, filed Oct. 18, 2022.
U.S. Appl. No. 17/996,556, filed Oct. 19, 2022.

U.S. Appl. No. 18/003,029, filed Dec. 22, 2022.
U.S. Appl. No. 18/006,807, filed Jan. 25, 2023.
U.S. Appl. No. 18/007,105, filed Jan. 27, 2023.
U.S. Appl. No. 18/041,109, filed Feb. 9, 2023.
U.S. Appl. No. 18/042,842, filed Feb. 24, 2023.
U.S. Appl. No. 18/043,618, filed Mar. 1, 2023.
U.S. Appl. No. 18/115,444, filed Feb. 28, 2023.
U.S. Appl. No. 18/134,857, filed Apr. 14, 2023.
U.S. Appl. No. 18/140,163, filed Apr. 27, 2023.
U.S. Appl. No. 18/140,751, filed Apr. 28, 2023.
U.S. Appl. No. 18/164,800, filed Feb. 6, 2023.
U.S. Appl. No. 18/198,464, filed May 17, 2023.
U.S. Appl. No. 18/246,121, filed Mar. 21, 2023.
U.S. Appl. No. 18/247,986, filed Apr. 5, 2023.
U.S. Appl. No. 18/259,626, filed Jun. 28, 2023.
U.S. Appl. No. 18/260,122, filed Jun. 30, 2023.
U.S. Appl. No. 18/260,391, filed Jul. 5, 2023.
U.S. Appl. No. 18/260,394, filed Jul. 5, 2023.
U.S. Appl. No. 18/263,800, filed Aug. 1, 2023.
U.S. Appl. No. 18/264,004, filed Aug. 2, 2023.
U.S. Appl. No. 18/265,736, filed Jun. 7, 2023.
U.S. Appl. No. 18/299,788, filed Apr. 13, 2023.
U.S. Appl. No. 18/335,579, filed Jun. 15, 2023.
U.S. Appl. No. 18/548,152, filed Aug. 28, 2023.
U.S. Appl. No. 18/549,387, filed Sep. 7, 2023.
U.S. Appl. No. 18/549,658, filed Sep. 8, 2023.
U.S. Appl. No. 62/923,279, filed Oct. 18, 2019.
U.S. Appl. No. 62/926,767, filed Oct. 28, 2019.
U.S. Appl. No. 62/935,337, filed Nov. 14, 2019.
U.S. Appl. No. 62/967,158, filed Jan. 26, 2020.
U.S. Appl. No. 62/967,977, filed Jan. 30, 2020.
U.S. Appl. No. 62/991,754, filed Mar. 19, 2020.
U.S. Appl. No. 63/008,112, filed Apr. 10, 2020.
U.S. Appl. No. 63/094,646, filed Oct. 21, 2020.
U.S. Appl. No. 63/109,084, filed Nov. 3, 2020.
U.S. Appl. No. 63/138,878, filed Jan. 19, 2021.
U.S. Appl. No. 63/150,640, filed Feb. 18, 2021.
U.S. Appl. No. 63/191,558, filed May 21, 2021.
U.S. Appl. No. 63/192,289, filed May 24, 2021.
U.S. Appl. No. 63/208,262, filed Jun. 8, 2021.
U.S. Appl. No. 63/230,897, filed Aug. 9, 2021.
U.S. Appl. No. 63/241,328, filed Sep. 7, 2021.
U.S. Appl. No. 63/299,208, filed Jan. 13, 2022.
U.S. Appl. No. 63/308,190, filed Feb. 9, 2022.
*PureWick Corporation* v. *Sage Products, LLC* Transcripts vol. 2 , Mar. 29, 2022.
*PureWick Corporation* v. *Sage Products, LLC* Transcripts vol. 3 , Mar. 30, 2022.
*PureWick Corporation* v. *Sage Products, LLC* Transcripts vol. 4 , Mar. 31, 2022.
*PureWick Corporation* v. *Sage Products, LLC* Transcripts vol. 5 , Apr. 1, 2022.
*PureWick Corporation* v. *Sage Products, LLC* Transcripts vol. 1 , Mar. 28, 2022.
"AMXD Control Starter Kit", Omni Medical Systems, Inc., 1 page.
"AMXDmax Advanced Mission Extender Device User & Maintenance Guide", Omni Medical, Jan. 11, 2010, 10 pages.
AMXDmax Development History 2002-2014, Omni Medical Systems, Inc., 2 pages.
"Combat Force Multiplier in Flight Bladder Relief Cockpit Essential Equipment Brochure", Omni Medical, 20 pages.
"GSA Price List", Omni Medical, Apr. 2011, 2 pages.
"How is Polypropylene Fiber Made", https:www.yarnsandfibers. com/textile-resources/synthetic-fibers/polypropylene-fiber/ polypropylene-fiber-production-raw-materials/how-is-polypropylene- fiber-made/ last accessed 2020, Oct. 7, 2020, 3 pages.
"Letter to Mark Harvie of Omni Measurement Systems", Department of Veterans Affairs, Nov. 1, 2007, 11 pages.
"Revised AMXDmax Advanced Mission Extender Device User & Maintenance Guide", Omni Medical Systems, Oct. 8, 2019, 52 pages.
"Rising Warrior Insulated Gallon Jug Cover", https://www.amazon. com/Rising-Warrior-Insulated-Sleeve, 2021, 2 pages.

(56)                References Cited

OTHER PUBLICATIONS

"Urine Bag Cover—Catheter Bag Cover 2000 ml volume—Medline Style—Multiple Sclerosis—Spine Injury—Suprapublic Catheter—Bladder Incontinence", https://www.etsy.com/listing/1142934658/urine-bag-cover-caatheter-bag-cover-2000, 2022, 1 page.
"Vinyl Dust Cover, Janome #741811000, Janome, Sewing Parts Online", https://www.sewingpartsonline.com/vinyl-dust-cover-janome-74181000, 2020, 2 pages.
Ali, "Sustainability Assessment: Seventh Generation Diapers versus gDiapers", The University of Vermont, Dec. 6, 2011, pp. 1-31.
Autumn, et al., "Frictional adhesion: a new angle on gecko attachment", The Journal of Experimental Biology, 2006, pp. 3569-3579.
Cañas, et al., "Effect of nano- and micro-roughness on adhesion of bioinspired micropatterned surfaces", Acta Biomaterialia 8, 2012, pp. 282-288.
Chaudhary, et al., "Bioinspired dry adhesive: Poly(dimethylsiloxane) grafted with poly(2-ethylhexyl acrylate) brushes", European Polymer Journal, 2015, pp. 432-440.
Dai, et al., "Non-sticky and Non-slippery Biomimetic Patterned Surfaces", Journal of Bionic Engineering, Mar. 2020, pp. 326-334.
Espinoza-Ramirez, "Nanobiodiversity and Biomimetic Adhesives Development: From Nature to Production and Application", Journal of Biomaterials and Nanobiotechnology, pp. 78-101, 2019.
Hwang, et al., "Multifunctional Smart Skin Adhesive Patches for Advanced Health Care", Adv. Healthcare Mater, 2018, pp. 1-20.
Jagota, et al., "Adhesion, friction, and compliance of bio-mimetic and bio-inspired structured interfaces", Materials Science and Engineering, 2011, pp. 253-292.
Jeong, et al., "A nontransferring dry adhesive with hierarchical polymer nanohairs", PNAS, Apr. 7, 2009, pp. 5639-5644.
Jeong, et al. , "Nanohairs and nanotubes: Efficient structural elements for gecko-inspired artificial dry adhesives", Science Direct, 2009, pp. 335-346.
Karp, et al., "Dry solution to a sticky problem", Nature., 2011, pp. 42-43.
Lee, et al., "Continuous Fabrication of Wide-Tip Microstructures for Bio-Inspired Dry Adhesives via Tip Inking Process", Journal of Chemistry, Jan. 2, 2019, pp. 1-5.
Merriam-Webster Dictionary, "Embed Definition & Meaning", https://www.merriam-webster.com/dictionary/embed last accessed Aug. 3, 2023, 2003.
Parness, et al., "A microfabricated wedge-shaped adhesive array displaying gecko-like dynamic adhesion, directionality", J.R. Soc. Interface, 2009, pp. 1223-1232.
Pieper, et al. , "An external urine-collection device for women: A clinical trial", Journal of ER Nursing, vol. 20, No. 2, Mar./Apr. 1993, pp. 51-55.
Tsipenyuk, et al., "Use of biomimetic hexagonal surface texture in friction against lubricated skin", Journal of The Royal Society—Interface, 2014, pp. 1-6.
Vinas, "A Solution for an Awkward—But Serious—Subject" , http://www.aero-news.net/index.cfm?do=main.textpost&id=69ae2bb1-838b-4098-a7b5-7flbb2505688 last accessed Feb. 8, 2021.
Advisory Action for U.S. Appl. No. 14/722,613 mailed Mar. 4, 2019.
Advisory Action for U.S. Appl. No. 14/952,591 mailed Jun. 1, 2018.
Advisory Action for U.S. Appl. No. 15/238,427 mailed Apr. 10, 2019.
Advisory Action for U.S. Appl. No. 16/899,956 mailed Jul. 9, 2021.
Advisory Action for U.S. Appl. No. 16/904,868 mailed Jul. 2, 2021.
Advisory Action for U.S. Appl. No. 16/905,400 mailed Jun. 9, 2021.
Corrected International Search Report and Written Opinion for International Application No. PCT/US2017/043025 mailed Jan. 11, 2018.
Corrected Notice of Allowability for U.S. Appl. No. 15/221,106 mailed Jul. 2, 2019.
Corrected Notice of Allowability for U.S. Appl. No. 15/612,325 mailed Mar. 17, 2021.
Final Office Action for U.S. Appl. No. 14/722,613 mailed on Nov. 29, 2018.

Final Office Action for U.S. Appl. No. 14/947,759 mailed Apr. 8, 2016.
Final Office Action for U.S. Appl. No. 14/952,591 mailed Feb. 23, 2018.
Final Office Action for U.S. Appl. No. 14/952,591 mailed Nov. 1, 2019.
Final Office Action for U.S. Appl. No. 14/952,591 mailed Nov. 27, 2020.
Final Office Action for U.S. Appl. No. 15/171,968 mailed Feb. 14, 2020.
Final Office Action for U.S. Appl. No. 15/171,968 mailed Mar. 19, 2019.
Final Office Action for U.S. Appl. No. 15/221,106 mailed Jan. 23, 2019.
Final Office Action for U.S. Appl. No. 15/238,427 mailed Jan. 2, 2019.
Final Office Action for U.S. Appl. No. 15/260,103 mailed Feb. 14, 2019.
Final Office Action for U.S. Appl. No. 15/612,325 mailed Sep. 17, 2020.
Final Office Action for U.S. Appl. No. 16/899,956 mailed Apr. 19, 2021.
Final Office Action for U.S. Appl. No. 16/904,868 mailed Mar. 26, 2021.
Final Office Action for U.S. Appl. No. 16/905,400 mailed Apr. 6, 2021.
Final Office Action for U.S. Appl. No. 17/088,272 mailed May 25, 2021.
Final Office Action for U.S. Appl. No. 29/624,661 mailed Feb. 18, 2020.
International Search Report and Written Opinion from International Application No. PCT/US2016/049274 mailed Dec. 1, 2016.
International Search Report and Written Opinion from International Application No. PCT/US2017/035625 mailed Aug. 15, 2017.
International Search Report and Written Opinion from International Application No. PCT/US2017/043025 mailed Oct. 18, 2017.
International Search Report and Written Opinion from International Application No. PCT/US2018/015968 mailed Apr. 6, 2018.
International Search Report and Written Opinion from International Application No. PCT/US2019/029608 mailed Sep. 3, 2019.
International Search Report and Written Opinion from International Application No. PCT/US2019/029609 mailed Sep. 3, 2019.
International Search Report and Written Opinion from International Application No. PCT/US2019/029610 mailed Sep. 3, 2019.
International Search Report and Written Opinion from International Application No. PCT/US2019/029611 mailed Jul. 3, 2019.
International Search Report and Written Opinion from International Application No. PCT/US2019/029613 mailed Jul. 3, 2019.
International Search Report and Written Opinion from International Application No. PCT/US2019/029614 mailed Sep. 26, 2019.
International Search Report and Written Opinion from International Application No. PCT/US2019/029616 mailed Aug. 30, 2019.
International Search Report and Written Opinion from International Application No. PCT/US2020/023572 mailed Jul. 6, 2020.
International Search Report and Written Opinion from International Application No. PCT/US2020/033064 mailed Aug. 31, 2020.
International Search Report and Written Opinion from International Application No. PCT/US2020/033122 mailed Aug. 31, 2020.
International Search Report and Written Opinion from International Application No. PCT/US2020/040860 mailed Oct. 2, 2020.
International Search Report and Written Opinion from International Application No. PCT/US2020/041242 mailed Nov. 17, 2020.
International Search Report and Written Opinion from International Application No. PCT/US2020/041249 mailed Oct. 2, 2020.
International Search Report and Written Opinion from International Application No. PCT/US2020/042262 mailed Oct. 14, 2020.
International Search Report and Written Opinion from International Application No. PCT/US2020/043059 mailed Oct. 6, 2020.
International Search Report and Written Opinion from International Application No. PCT/US2020/044024 mailed Nov. 12, 2020.
International Search Report and Written Opinion from International Application No. PCT/US2020/046914 mailed Dec. 1, 2020.

(56)             References Cited

OTHER PUBLICATIONS

International Search Report and Written Opinion from International Application No. PCT/US2020/055680 mailed Dec. 15, 2020.
International Search Report and Written Opinion from International Application No. PCT/US2020/061563 mailed Feb. 19, 2021.
International Search Report and Written Opinion from International Application No. PCT/US2020/065234 mailed Apr. 12, 2021.
International Search Report and Written Opinion from International Application No. PCT/US2020/067451 mailed Mar. 25, 2021.
International Search Report and Written Opinion from International Application No. PCT/US2020/067454 mailed Mar. 29, 2021.
International Search Report and Written Opinion from International Application No. PCT/US2020/067455 mailed Mar. 26, 2021.
International Search Report and Written Opinion from International Application No. PCT/US2021/015024 mailed May 18, 2021.
International Search Report and Written Opinion from International Application No. PCT/US2021/015787 mailed May 27, 2021.
International Search Report and Written Opinion from International Application No. PCT/US2021/023001 mailed Jun. 21, 2021.
International Search Report and Written Opinion from International Application No. PCT/US2021/024162 mailed Jul. 8, 2021.
International Search Report and Written Opinion from International Application No. PCT/US2021/027061 mailed Jul. 19, 2021.
International Search Report and Written Opinion from International Application No. PCT/US2021/027104 mailed Jul. 6, 2021.
International Search Report and Written Opinion from International Application No. PCT/US2021/027314 mailed Jul. 6, 2021.
International Search Report and Written Opinion from International Application No. PCT/US2021/027422 mailed Aug. 12, 2021.
International Search Report and Written Opinion from International Application No. PCT/US2021/027425 mailed Aug. 11, 2021.
International Search Report and Written Opinion from International Application No. PCT/US2021/027913 mailed Jul. 12, 2021.
International Search Report and Written Opinion from International Application No. PCT/US2021/027917 mailed Aug. 19, 2021.
International Search Report and Written Opinion from International Application No. PCT/US2021/035181 mailed Sep. 16, 2021.
Issue Notification for U.S. Appl. No. 14/952,591 mailed Jul. 28, 2021.
Issue Notification for U.S. Appl. No. 15/171,968 mailed Mar. 3, 2021.
Issue Notification for U.S. Appl. No. 15/221,106 mailed Jul. 24, 2019.
Issue Notification for U.S. Appl. No. 15/238,427 mailed Jul. 24, 2019.
Issue Notification for U.S. Appl. No. 15/260,103 mailed Aug. 7, 2019.
Issue Notification for U.S. Appl. No. 15/611,587 mailed Feb. 20, 2019.
Issue Notification for U.S. Appl. No. 15/612,325 mailed Mar. 24, 2021.
Issue Notification for U.S. Appl. No. 29/624,661 mailed Aug. 4, 2021.
Non-Final Office Action for U.S. Appl. No. 14/592,591 mailed Mar. 20, 2020.
Non-Final Office Action for U.S. Appl. No. 14/722,613 mailed Jun. 13, 2019.
Non-Final Office Action for U.S. Appl. No. 14/947,759 mailed Mar. 17, 2016.
Non-Final Office Action for U.S. Appl. No. 14/952,591 mailed Aug. 1, 2017.
Non-Final Office Action for U.S. Appl. No. 14/952,591 mailed Mar. 20, 2020.
Non-Final Office Action for U.S. Appl. No. 14/952,591 mailed Mar. 21, 2019.
Non-Final Office Action for U.S. Appl. No. 14/952,591 mailed Sep. 28, 2018.
Non-Final Office Action for U.S. Appl. No. 15/171,968 mailed May 11, 2020.
Non-Final Office Action for U.S. Appl. No. 15/171,968 mailed Aug. 20, 2019.
Non-Final Office Action for U.S. Appl. No. 15/171,968 mailed Jun. 12, 2018.
Non-Final Office Action for U.S. Appl. No. 15/221,106 mailed Jun. 5, 2018.
Non-Final Office Action for U.S. Appl. No. 15/238,427 mailed Aug. 8, 2018.
Non-Final Office Action for U.S. Appl. No. 15/260,103 mailed Sep. 26, 2018.
Non-Final Office Action for U.S. Appl. No. 15/611,587 mailed Dec. 29, 2017.
Non-Final Office Action for U.S. Appl. No. 15/611,587 mailed Jul. 13, 2018.
Non-Final Office Action for U.S. Appl. No. 15/612,325 mailed Mar. 19, 2020.
Non-Final Office Action for U.S. Appl. No. 16/449,039 mailed Dec. 8, 2021.
Non-Final Office Action for U.S. Appl. No. 16/452,145 mailed Sep. 28, 2021.
Non-Final Office Action for U.S. Appl. No. 16/452,258 mailed Sep. 28, 2021.
Non-Final Office Action for U.S. Appl. No. 16/478,180 mailed Oct. 22, 2021.
Non-Final Office Action for U.S. Appl. No. 16/899,956 mailed Oct. 16, 2020.
Non-Final Office Action for U.S. Appl. No. 16/899,956 mailed Sep. 2, 2021.
Non-Final Office Action for U.S. Appl. No. 16/904,868 mailed Nov. 25, 2020.
Non-Final Office Action for U.S. Appl. No. 16/904,868 mailed Oct. 5, 2021.
Non-Final Office Action for U.S. Appl. No. 16/905,400 mailed Dec. 2, 2020.
Non-Final Office Action for U.S. Appl. No. 16/905,400 mailed Jul. 22, 2021.
Non-Final Office Action for U.S. Appl. No. 17/088,272 mailed Jan. 25, 2021.
Non-Final Office Action for U.S. Appl. No. 17/330,657 mailed Aug. 11, 2021.
Non-Final Office Action for U.S. Appl. No. 29/624,661 mailed Jul. 18, 2019.
Non-Final Office Action for U.S. Appl. No. 29/694,002 mailed Jun. 24, 2020.
Notice of Allowance for U.S. Appl. No. 14/952,591 mailed Apr. 5, 2021.
Notice of Allowance for U.S. Appl. No. 14/952,591 mailed Jul. 8, 2021.
Notice of Allowance for U.S. Appl. No. 15/171,968 mailed Feb. 16, 2021.
Notice of Allowance for U.S. Appl. No. 15/171,968 mailed Nov. 6, 2020.
Notice of Allowance for U.S. Appl. No. 15/221,106 mailed May 1, 2019.
Notice of Allowance for U.S. Appl. No. 15/238,427 mailed May 23, 2019.
Notice of Allowance for U.S. Appl. No. 15/260,103 mailed Jun. 7, 2019.
Notice of Allowance for U.S. Appl. No. 15/611,587 mailed Dec. 21, 2018.
Notice of Allowance for U.S. Appl. No. 15/612,325 mailed Feb. 19, 2021.
Notice of Allowance for U.S. Appl. No. 15/612,325 mailed Jan. 21, 2021.
Notice of Allowance for U.S. Appl. No. 17/088,272 mailed Aug. 5, 2021.
Notice of Allowance for U.S. Appl. No. 29/624,661 mailed Apr. 28, 2021.
Notice of Allowance for U.S. Appl. No. 29/624,661 mailed Jul. 10, 2020.
Notice of Allowance for U.S. Appl. No. 29/624,661 mailed May 14, 2020.

(56)     References Cited

OTHER PUBLICATIONS

Notice of Allowance for U.S. Appl. No. 29/624,661 mailed Sep. 29, 2020.
Notice of Allowance for U.S. Appl. No. 29/694,002 mailed Apr. 29, 2021.
Notice of Allowance for U.S. Appl. No. 29/694,002 mailed Jan. 29, 2021.
Notice of Allowance for U.S. Appl. No. 29/694,002 mailed Oct. 16, 2020.
Notice to File Missing Parts for U.S. Appl. No. 17/179,116 mailed Mar. 3, 2021.
Restriction Requirement for U.S. Appl. No. 16/478,180 mailed May 25, 2021.
U.S. Appl. No. 14/433,773, filed Apr. 3, 2020.
U.S. Appl. No. 14/625,469, filed Feb. 28, 2015.
U.S. Appl. No. 14/947,759, filed Nov. 20, 2015.
U.S. Appl. No. 14/952,591, filed Nov. 25, 2015.
U.S. Appl. No. 15/171,968, filed Jun. 2, 2016.
U.S. Appl. No. 15/221,106, filed Jul. 27, 2016.
U.S. Appl. No. 15/260,103, filed Sep. 8, 2016.
U.S. Appl. No. 15/612,325, filed Jun. 2, 2017.
U.S. Appl. No. 16/245,726, filed Jan. 11, 2019.
U.S. Appl. No. 16/369,676, filed Mar. 29, 2019.
U.S. Appl. No. 16/433,773, filed Jun. 6, 2019.
U.S. Appl. No. 16/449,039, filed Jun. 21, 2019.
U.S. Appl. No. 16/452,145, filed Jun. 25, 2019.
U.S. Appl. No. 16/452,258, filed Jun. 25, 2019.
U.S. Appl. No. 16/478,180, filed Jul. 16, 2019.
U.S. Appl. No. 16/904,868, filed Jun. 18, 2020.
U.S. Appl. No. 16/905,400, filed Jun. 18, 2020.
U.S. Appl. No. 17/051,550, filed Oct. 29, 2020.
U.S. Appl. No. 17/051,554, filed Oct. 29, 2020.
U.S. Appl. No. 17/051,585, filed Oct. 29, 2020.
U.S. Appl. No. 17/051,600, filed Oct. 29, 2020.
U.S. Appl. No. 17/088,272, filed Nov. 3, 2020.
U.S. Appl. No. 17/179,116, filed Feb. 18, 2021.
U.S. Appl. No. 17/330,657, filed May 26, 2021.
U.S. Appl. No. 17/378,015, filed Jul. 16, 2021.
U.S. Appl. No. 17/412,864, filed Aug. 26, 2021.
U.S. Appl. No. 17/444,825, filed Aug. 10, 2021.
U.S. Appl. No. 17/446,256, filed Aug. 27, 2021.
U.S. Appl. No. 17/446,654, filed Sep. 1, 2021.
U.S. Appl. No. 17/447,123, filed Sep. 8, 2021.
U.S. Appl. No. 17/450,864, filed Oct. 14, 2021.
U.S. Appl. No. 17/451,345, filed Oct. 19, 2021.
U.S. Appl. No. 17/451,354, filed Oct. 19, 2021.
U.S. Appl. No. 17/453,560, filed Nov. 4, 2021.
U.S. Appl. No. 17/461,036 mailed Aug. 30, 2021.
U.S. Appl. No. 17/494,578, filed Oct. 5, 2021.
U.S. Appl. No. 17/501,591, filed Oct. 14, 2021.
U.S. Appl. No. 29/741,751, filed Jul. 15, 2020.
U.S. Appl. No. 61/955,537, filed Mar. 19, 2014.
U.S. Appl. No. 62/082,279, filed Nov. 20, 2014.
U.S. Appl. No. 62/084,078, filed Nov. 25, 2014.
U.S. Appl. No. 62/414,963, filed Oct. 31, 2016.
U.S. Appl. No. 62/452,437, filed Jan. 31, 2017.
U.S. Appl. No. 62/485,578, filed Apr. 14, 2017.
U.S. Appl. No. 62/665,297, filed May 1, 2018.
U.S. Appl. No. 62/665,302, filed May 1, 2018.
U.S. Appl. No. 62/665,317, filed May 1, 2018.
U.S. Appl. No. 62/665,321, filed May 1, 2018.
U.S. Appl. No. 62/665,331, filed May 1, 2018.
U.S. Appl. No. 62/665,335, filed May 1, 2018.
U.S. Appl. No. 62/853,279, filed May 28, 2019.
U.S. Appl. No. 62/853,889, filed May 29, 2019.
U.S. Appl. No. 62/864,656, filed Jun. 21, 2019.
U.S. Appl. No. 62/873,045, filed Jul. 11, 2019.
U.S. Appl. No. 62/873,048, filed Jul. 11, 2019.
U.S. Appl. No. 62/876,500, filed Jul. 19, 2019.
U.S. Appl. No. 62/877,558, filed Jul. 23, 2019.
U.S. Appl. No. 62/883,172, filed Aug. 6, 2019.
U.S. Appl. No. 62/889,149, filed Aug. 20, 2019.
U.S. Appl. No. 62/938,447, filed Nov. 21, 2019.
U.S. Appl. No. 62/949,187, filed Dec. 17, 2019.
U.S. Appl. No. 62/956,756, filed Jan. 3, 2020.
U.S. Appl. No. 62/956,767, filed Jan. 3, 2020.
U.S. Appl. No. 62/956,770, filed Jan. 3, 2020.
U.S. Appl. No. 62/994,912, filed Mar. 26, 2020.
U.S. Appl. No. 63/011,445, filed Apr. 17, 2020.
U.S. Appl. No. 63/011,487, filed Apr. 17, 2020.
U.S. Appl. No. 63/011,571, filed Apr. 17, 2020.
U.S. Appl. No. 63/011,657, filed Apr. 17, 2020.
U.S. Appl. No. 63/011,760, filed Apr. 17, 2020.
U.S. Appl. No. 63/012,347, filed Apr. 20, 2020.
U.S. Appl. No. 63/012,384, filed Apr. 20, 2020.
U.S. Appl. No. 63/030,685, filed May 27, 2020.
U.S. Appl. No. 63/033,310, filed Jun. 2, 2020.
U.S. Appl. No. 63/047,374, filed Jul. 2, 2020.
U.S. Appl. No. 63/061,241, filed Aug. 5, 2020.
U.S. Appl. No. 63/061,244, filed Aug. 5, 2020.
U.S. Appl. No. 63/061,834, filed Aug. 6, 2020.
U.S. Appl. No. 63/064,017, filed Aug. 11, 2020.
U.S. Appl. No. 63/064,126, filed Aug. 11, 2020.
U.S. Appl. No. 63/067,542, filed Aug. 19, 2020.
U.S. Appl. No. 63/071,438, filed Aug. 28, 2020.
U.S. Appl. No. 63/071,821, filed Aug. 28, 2020.
U.S. Appl. No. 63/073,545, filed Sep. 2, 2020.
U.S. Appl. No. 63/073,553, filed Sep. 2, 2020.
U.S. Appl. No. 63/074,051, filed Sep. 3, 2020.
U.S. Appl. No. 63/074,066, filed Sep. 3, 2020.
U.S. Appl. No. 63/076,032, filed Sep. 9, 2020.
U.S. Appl. No. 63/076,474, filed Sep. 10, 2020.
U.S. Appl. No. 63/076,477, filed Sep. 10, 2020.
U.S. Appl. No. 63/082,261, filed Sep. 23, 2020.
U.S. Appl. No. 63/088,506, filed Oct. 7, 2020.
U.S. Appl. No. 63/088,511, filed Oct. 7, 2020.
U.S. Appl. No. 63/088,539, filed Oct. 7, 2020.
U.S. Appl. No. 63/094,464, filed Oct. 21, 2020.
U.S. Appl. No. 63/094,498, filed Oct. 21, 2020.
U.S. Appl. No. 63/094,594, filed Oct. 21, 2020.
U.S. Appl. No. 63/094,608, filed Oct. 21, 2020.
U.S. Appl. No. 63/094,626, filed Oct. 21, 2020.
U.S. Appl. No. 63/109,066, filed Nov. 3, 2020.
U.S. Appl. No. 63/112,417, filed Nov. 11, 2020.
U.S. Appl. No. 63/119,161, filed Nov. 30, 2020.
U.S. Appl. No. 63/124,271, filed Dec. 11, 2020.
U.S. Appl. No. 63/133,892, filed Jan. 5, 2021.
U.S. Appl. No. 63/134,287, filed Jan. 6, 2021.
U.S. Appl. No. 63/134,450, filed Jan. 6, 2021.
U.S. Appl. No. 63/134,631, filed Jan. 7, 2021.
U.S. Appl. No. 63/134,632, filed Jan. 7, 2021.
U.S. Appl. No. 63/134,754, filed Jan. 7, 2021.
U.S. Appl. No. 63/146,946, filed Feb. 8, 2021.
U.S. Appl. No. 63/147,013, filed Feb. 8, 2021.
U.S. Appl. No. 63/147,299, filed Feb. 9, 2021.
U.S. Appl. No. 63/148,723, filed Feb. 12, 2021.
U.S. Appl. No. 63/154,248, filed Feb. 26, 2021.
U.S. Appl. No. 63/155,395, filed Mar. 2, 2021.
U.S. Appl. No. 63/157,007, filed Mar. 5, 2021.
U.S. Appl. No. 63/157,014, filed Mar. 5, 2021.
U.S. Appl. No. 63/159,142, filed Mar. 10, 2021.
U.S. Appl. No. 63/159,186, filed Mar. 10, 2021.
U.S. Appl. No. 63/159,210, filed Mar. 10, 2021.
U.S. Appl. No. 63/159,280, filed Mar. 10, 2021.
U.S. Appl. No. 63/165,273, filed Mar. 24, 2021.
U.S. Appl. No. 63/165,384, filed Mar. 24, 2021.
U.S. Appl. No. 63/171,165, filed Apr. 6, 2021.
U.S. Appl. No. 63/172,975, filed Apr. 9, 2021.
U.S. Appl. No. 63/181,695, filed Apr. 29, 2021.
U.S. Appl. No. 63/192,274, filed May 24, 2021.
U.S. Appl. No. 63/193,235, filed May 26, 2021.
U.S. Appl. No. 63/193,406, filed May 26, 2021.
U.S. Appl. No. 63/193,891, filed May 27, 2021.

(56)         References Cited

OTHER PUBLICATIONS

U.S. Appl. No. 63/214,551, filed Jun. 24, 2021.
U.S. Appl. No. 63/214,570, filed Jun. 24, 2021.
U.S. Appl. No. 63/215,017, filed Jun. 25, 2021.
U.S. Appl. No. 63/228,244, filed Aug. 2, 2021.
U.S. Appl. No. 63/228,252, filed Aug. 2, 2021.
U.S. Appl. No. 63/228,258, filed Aug. 2, 2021.
U.S. Appl. No. 63/230,894, filed Aug. 9, 2021.
U.S. Appl. No. 63/238,457, filed Aug. 30, 2021.
U.S. Appl. No. 63/238,477, filed Aug. 30, 2021.
U.S. Appl. No. 63/241,562, filed Sep. 8, 2021.
U.S. Appl. No. 63/241,564, filed Sep. 8, 2021.
U.S. Appl. No. 63/241,575, filed Sep. 8, 2021.
U.S. Appl. No. 63/246,972, filed Sep. 22, 2021.
U.S. Appl. No. 63/247,375, filed Sep. 23, 2021.
U.S. Appl. No. 63/247,478, filed Sep. 23, 2021.
U.S. Appl. No. 63/247,491, filed Sep. 23, 2021.
Sage's Second Supplemental Invalidity Contentions Regarding U.S. Pat. Nos. 8,287,508, 10,226,375, 10,390,989, and 10,376,407,292 pages.
Plaintiff's Identification of Claim Terms and Proposed Construction, 3 pages.
Sage's Preliminary Identification of Claim Elements and Proposed Constructions for U.S. Pat. Nos. 8,287,508, 10,226,376, 10,390,989 and 10,376,407, 7 pages.
Corrected Certificate of Service, 2020, 2 pages.
Excerpts from the 508 (U.S. Pat. No. 8,278,508) Patent's Prosecution History, 2020, 99 pages.
Declaration of Diane K. Newman Curriculum Vitae, 2020, pp. 1-199.
Sage's Supplemental and Initial Invalidity Contentions Regarding U.S. Pat. Nos. 8,287,508; 10,226,375; 10,390,989 and Initial Invalidity Contentions Regarding U.S. Pat. No. 10,376,407, Aug. 21, 2020, 277 pages.
Decision Granting Institution of Inter Partes Review for U.S. Pat. No. 8,287,508, Feb. 17, 2021, 39 pages.
Memorandum Order, Feb. 2021, 14 pgs.
Boehringer CareDry System—Second Generation for Non-Invasive Urinary Management for Females, Mar. 2021, 3 pgs.
PureWick's Response to Interrogatory No. 9 in *PureWick, LLC* v. *Sage Products, LLC*, Mar. 23, 2020, 6 pages.
Sage's Initial Invalidity Contentions Regarding U.S. Pat. Nos. 8,287,508; 10,226,375; and 10,390,989, May 29, 2020, 193 pages.
Defendant and Counterclaim Plaintiff Sage Products, LLC's Answer, Defenses, and Counterclaims to Plaintiff's Amended Complaint, Nov. 1, 2019.
Plaintiff's Opening Claim Construction Brief, Oct. 16, 2020, 26 pages.
"3 Devices Take Top Honors in Dare-to-Dream Medtech Design Contest", R+D Digest, Nov. 2013, 1 page.
"Advanced Mission Extender Device (AMDX) Products", Omni Medical Systems, Inc., 15 pages.
"AMXD Control Starter Kit Brochure", https://www.omnimedicalsys.com/index.php?page=products, 8 pages.
"AMXDmax In-Flight Bladder Relief", Omni Medical; Omni Medical Systems, Inc., 2015.
"AMXDX—Advanced Mission Extender Device Brochure", Omni Medical, 2 pages.
"External Urine Management for Female Anatomy", https://www.stryker.com/us/en/sage/products/sage-primafit.html, Jul. 2020, 4 pages.
"High Absorbancy Cellulose Acetate Electrospun Nanofibers for Feminine Hygiene Application", https://www.sciencedirect.com/science/article/abs/pii/S2352940716300701?via%3Dihub, Jul. 2016, 3 pages.
"How Period Panties Work", www.shethinx.com/pages/thinx-itworks, 2020, 10 pages.
"Hydrogel properties of electrospun polyvinylpyrrolidone and polyvinylpyrrolidone/poly(acrylic acid) blend nanofibers", https://pubs.rsc.org/en/content/articlelanding/2015/ra/c5ra07514a#!divAbstract, 2015, 5 pages.

"In Flight Bladder Relief", Omni Medical, 14 pages.
"Making Women's Sanitary Products Safer and Cheaper", https://www.elsevier.com/connect/making-womens-sanitary-products-safer-and-cheaper, Sep. 2016, 10 pages.
"Novel Nanofibers Make Safe and Effective Absorbent for Sanitary Products", https://www.materialstoday.com/nanomaterials/news/nanofibers-make-safe-and-effective-absorbent/, Oct. 2016, 3 pages.
"Research and Development Work Relating to Assistive Technology Jun. 2005", British Department of Health, Nov. 2006, 40 pages.
"Step by Step How Ur24 WorksHome", http://medicalpatentur24.com, Aug. 30, 2017, 4 pages.
"Underwear that absorbs your period", Thinx!, 7 pages.
"User & Maintenance Guide", Omni Medical, 2007, 16 pages.
"Winners Announced for Dare-to-Dream Medtech Design Challenge", https://www.mddionline.com/design-engineering/winners-announced-dare-dream-medtech-design-challenge, 2014, 4 pages.
Hollister, Female Urinary and Pouch and Male Urinary Pouch Brochure, 2011, 1 page.
Hollister, "Male Urinary Pouch External Collection Device", http://www.hollister.com/en/products/Continence-Care-Products/Urine-Collectors/Urine-Collection-Accessories/Male-Urinary-Pouch-External-Collection-Device.
Hollister, "Retracted Penis Pouch by Hollister", Vitality Medical.com, 6 pages.
MacAulay, et al., "A Noninvasive Continence Management System: Development and Evaluation of a Novel Toileting Device for Women", The Wound, Ostomy and Continence Nurses Society, 2007, pp. 641-648.
Newman, et al., "The Urinary Incontinence Sourcebook", Petition for Interparties Review, 1997, 23 pages.
Newton, et al., "Measuring Safety, Effectiveness and Ease of Use of PureWick in the Management of Urinary Incontinence in Bedbound Women: Case Studies", Jan. 8, 2016, 11 pages.
Parmar, "10 Finalists Chosen for Dare-to-Dream Medtech Design Challenge (PureWick)", Design Services, Nov. 10, 2014, 3 pages.
Purewick, "Incontinence Relief for Women", Presentation, Sep. 23, 2015, 7 pages.
Pytlik, "Super Absorbent Polymers", University of Buffalo.
Sachtman, "New Relief for Pilots? It Depends", Wired, 2008, 2 pages.
International Search Report and Written Opinion from International Application No. PCT/US2021/043893 mailed Nov. 22, 2021.
Advisory Action for U.S. Appl. No. 16/433,773 mailed Dec. 29, 2023.
Advisory Action for U.S. Appl. No. 16/904,868 mailed Jan. 2, 2024.
Advisory Action for U.S. Appl. No. 17/051,585 mailed Oct. 17, 2023.
Advisory Action for U.S. Appl. No. 17/179,116 mailed Jan. 8, 2024.
Advisory Action for U.S. Appl. No. 17/446,256 mailed Dec. 8, 2023.
Advisory Action for U.S. Appl. No. 17/448,811 mailed Nov. 15, 2023.
Advisory Action for U.S. Appl. No. 17/451,345 mailed Oct. 20, 2023.
Advisory Action for U.S. Appl. No. 17/453,260 mailed Dec. 22, 2023.
Advisory Action for U.S. Appl. No. 17/653,137 mailed Dec. 1, 2023.
Advisory Action for U.S. Appl. No. 17/655,464 mailed Dec. 13, 2023.
Communication of Notice of Opposition of European Application No. 17807547.9 mailed Jan. 5, 2024.
Corrected Notice of Allowability for U.S. Appl. No. 16/369,676 mailed Dec. 7, 2023.
Final Office Action for U.S. Appl. No. 16/433,773 mailed Oct. 10, 2023.
Final Office Action for U.S. Appl. No. 16/449,039 mailed Nov. 21, 2023.
Final Office Action for U.S. Appl. No. 16/452,258 mailed Dec. 21, 2023.
Final Office Action for U.S. Appl. No. 16/904,868 mailed Nov. 2, 2023.

(56) References Cited

OTHER PUBLICATIONS

Final Office Action for U.S. Appl. No. 17/051,399 mailed Jan. 8, 2024.

Final Office Action for U.S. Appl. No. 17/179,116 mailed Oct. 31, 2023.

Final Office Action for U.S. Appl. No. 17/446,256 mailed Sep. 19, 2023.

Final Office Action for U.S. Appl. No. 17/450,864 mailed Dec. 28, 2023.

Final Office Action for U.S. Appl. No. 17/451,354 mailed Oct. 30, 2023.

Final Office Action for U.S. Appl. No. 17/453,260 mailed Oct. 5, 2023.

Final Office Action for U.S. Appl. No. 17/501,591 mailed Nov. 14, 2023.

Final Office Action for U.S. Appl. No. 17/646,771 mailed Dec. 21, 2023.

Final Office Action for U.S. Appl. No. 17/653,137 mailed Sep. 21, 2023.

Final Office Action for U.S. Appl. No. 17/661,090 mailed Dec. 11, 2023.

Final Office Action for U.S. Appl. No. 17/663,330 mailed Dec. 12, 2023.

Final Office Action for U.S. Appl. No. 17/664,487 mailed Jan. 4, 2024.

Final Office Action for U.S. Appl. No. 18/139,523 mailed Dec. 22, 2023.

Final Office Action for U.S. Appl. No. 18/140,751 mailed Jan. 17, 2024.

Final Office Action for U.S. Appl. No. 18/164,800 mailed Dec. 6, 2023.

International Search Report and Written Opinion from International Application No. PCT/US2023/018474 mailed Sep. 11, 2023.

International Search Report and Written Opinion from International Application No. PCT/US2023/024805 mailed Dec. 14, 2023.

Issue Notification for U.S. Appl. No. 16/245,726 mailed Oct. 18, 2023.

Issue Notification for U.S. Appl. No. 17/461,036 mailed Oct. 11, 2023.

Issue Notification for U.S. Appl. No. 17/663,046 mailed Dec. 20, 2023.

Non-Final Office Action for U.S. Appl. No. 16/452,145 mailed Nov. 2, 2023.

Non-Final Office Action for U.S. Appl. No. 16/478,180 mailed Nov. 7, 2023.

Non-Final Office Action for U.S. Appl. No. 17/051,550 mailed Oct. 24, 2023.

Non-Final Office Action for U.S. Appl. No. 17/051,585 mailed Jan. 8, 2024.

Non-Final Office Action for U.S. Appl. No. 17/051,600 mailed Jan. 17, 2024.

Non-Final Office Action for U.S. Appl. No. 17/444,792 mailed Nov. 17, 2023.

Non-Final Office Action for U.S. Appl. No. 17/447,123 mailed Jan. 24, 2024.

Non-Final Office Action for U.S. Appl. No. 17/448,811 mailed Jan. 17, 2024.

Non-Final Office Action for U.S. Appl. No. 17/451,345 mailed Jan. 17, 2024.

Non-Final Office Action for U.S. Appl. No. 17/453,560 mailed Oct. 16, 2023.

Non-Final Office Action for U.S. Appl. No. 17/653,137 mailed Jan. 18, 2024.

Non-Final Office Action for U.S. Appl. No. 17/657,474 mailed Sep. 12, 2023.

Non-Final Office Action for U.S. Appl. No. 17/808,354 mailed Nov. 28, 2023.

Non-Final Office Action for U.S. Appl. No. 18/140,163 mailed Nov. 9, 2023.

Non-Final Office Action for U.S. Appl. No. 18/140,751 mailed Sep. 14, 2023.

Non-Final Office Action for U.S. Appl. No. 18/198,464 mailed Dec. 7, 2023.

Notice of Allowance for U.S. Appl. No. 16/369,676 mailed Nov. 14, 2023.

Notice of Allowance for U.S. Appl. No. 17/051,554 mailed Oct. 18, 2023.

Notice of Allowance for U.S. Appl. No. 17/662,700 mailed Nov. 15, 2023.

Notice of Allowance for U.S. Appl. No. 18/299,788 mailed Nov. 6, 2023.

Restriction Requirement for U.S. Appl. No. 17/051,600 mailed Sep. 21, 2023.

Restriction Requirement for U.S. Appl. No. 18/134,857 mailed Oct. 23, 2023.

Submission in Opposition Proceedings for European Application No. 17807547.9 filed Jan. 10, 2024.

U.S. Appl. No. 15/611,587, filed Jun. 1, 2017.

U.S. Appl. No. 17/451,719, filed Oct. 19, 2021.

U.S. Appl. No. 18/373,424, filed Sep. 27, 2023.

U.S. Appl. No. 18/376,274, filed Oct. 3, 2023.

U.S. Appl. No. 18/389,009, filed Nov. 13, 2023.

U.S. Appl. No. 18/415,080, filed Jan. 17, 2024.

U.S. Appl. No. 18/553,625, filed Oct. 2, 2023.

U.S. Appl. No. 18/556,945, filed Oct. 24, 2023.

U.S. Appl. No. 18/558,502, filed Nov. 1, 2023.

U.S. Appl. No. 18/562,626, filed Nov. 20, 2023.

U.S. Appl. No. 18/563,672, filed Nov. 22, 2023.

U.S. Appl. No. 18/569,711, filed Dec. 13, 2023.

U.S. Appl. No. 18/569,778, filed Dec. 13, 2023.

U.S. Appl. No. 63/596,012, filed Nov. 3, 2023.

U.S. Appl. No. 63/608,553, filed Dec. 11, 2023.

Wikipedia Article, "Zylinder (Geometrie)",https://de.wikipedia.org/w/index.php?title=Zylinder (Geometrie)&oldid=154862081, version of Jun. 1, 2016, 7 pages.

Advisory Action for U.S. Appl. No. 17/444,792 mailed Jul. 8, 2024.

Final Office Action for U.S. Appl. No. 17/051,585 mailed Jul. 5, 2024.

Final Office Action for U.S. Appl. No. 17/446,256 mailed Aug. 7, 2024.

Final Office Action for U.S. Appl. No. 17/653,137 mailed Aug. 7, 2024.

International Search Report and Written Opinion from International Application No. PCT/US2023/036868 mailed Jun. 5, 2024.

International Search Report and Written Opinion from International Application No. PCT/US2023/075507 mailed Jun. 13, 2024.

International Search Report and Written Opinion from International Application No. PCT/US2023/077168 mailed Jun. 24, 2024.

Issue Notification for U.S. Appl. No. 17/326,980 mailed Jul. 10, 2024.

Issue Notification for U.S. Appl. No. 17/448,811 mailed Jul. 3, 2024.

Issue Notification for U.S. Appl. No. 17/453,260 mailed Jul. 10, 2024.

Issue Notification for U.S. Appl. No. 17/453,560 mailed Aug. 7, 2024.

Non-Final Office Action for U.S. Appl. No. 16/478,180 mailed Aug. 7, 2024.

Non-Final Office Action for U.S. Appl. No. 17/378,015 mailed Jul. 5, 2024.

Non-Final Office Action for U.S. Appl. No. 18/451,080 mailed Jul. 30, 2024.

Notice of Allowance for U.S. Appl. No. 16/452,145 mailed Jul. 11, 2024.

Notice of Allowance for U.S. Appl. No. 17/447,123 mailed Jul. 26, 2024.

Notice of Allowance for U.S. Appl. No. 17/501,591 mailed Jul. 31, 2024.

Notice of Allowance for U.S. Appl. No. 17/664,914 mailed Jul. 26, 2024.

Notice of Allowance for U.S. Appl. No. 18/198,464 mailed Jul. 30, 2024.

(56)　　　　　References Cited

OTHER PUBLICATIONS

Restriction Requirement for U.S. Appl. No. 17/625,941 mailed Aug. 7, 2024.
U.S. Appl. No. 18/728,604, filed Jul. 12, 2024.
U.S. Appl. No. 18/834,115, filed Jul. 29, 2024.
U.S. Appl. No. 18/834,176, filed Jul. 29, 2024.
U.S. Appl. No. 18/834,340, filed Jul. 30, 2024.
U.S. Appl. No. 18/835,068, filed Aug. 1, 2024.
U.S. Appl. No. 18/835,444, filed Aug. 2, 2024.
U.S. Appl. No. 18/836,204, filed Aug. 6, 2024.
Advisory Action for U.S. Appl. No. 16/449,039 mailed Jan. 25, 2024.
Advisory Action for U.S. Appl. No. 16/452,258 mailed Apr. 8, 2024.
Advisory Action for U.S. Appl. No. 16/478,180 mailed Jun. 7, 2024.
Advisory Action for U.S. Appl. No. 17/446,654 mailed Apr. 15, 2024.
Advisory Action for U.S. Appl. No. 17/450,864 mailed Mar. 21, 2024.
Advisory Action for U.S. Appl. No. 17/451,345 mailed Jul. 3, 2024.
Advisory Action for U.S. Appl. No. 17/451,354 mailed Jan. 30, 2024.
Advisory Action for U.S. Appl. No. 17/501,591 mailed Feb. 22, 2024.
Advisory Action for U.S. Appl. No. 17/646,771 mailed Feb. 29, 2024.
Advisory Action for U.S. Appl. No. 17/661,090 mailed Feb. 26, 2024.
Advisory Action for U.S. Appl. No. 17/663,330 mailed Feb. 27, 2024.
Advisory Action for U.S. Appl. No. 17/664,487 mailed Mar. 13, 2024.
Advisory Action for U.S. Appl. No. 17/808,354 mailed Jun. 12, 2024.
Advisory Action for U.S. Appl. No. 18/139,523 mailed Apr. 24, 2024.
Advisory Action for U.S. Appl. No. 18/140,163 mailed Jun. 3, 2024.
Advisory Action for U.S. Appl. No. 18/140,751 mailed Apr. 24, 2024.
Advisory Action for U.S. Appl. No. 18/164,800 mailed Feb. 12, 2024.
Corrected Notice of Allowability for U.S. Appl. No. 17/326,980 mailed Feb. 8, 2024.
Corrected Notice of Allowability for U.S. Appl. No. 17/657,474 mailed Mar. 13, 2024.
Corrected Notice of Allowability for U.S. Appl. No. 17/657,474 mailed May 14, 2024.
Final Office Action for U.S. Appl. No. 16/478,180 mailed Feb. 28, 2024.
Final Office Action for U.S. Appl. No. 17/051,600 mailed Jun. 27, 2024.
Final Office Action for U.S. Appl. No. 17/444,792 mailed Apr. 3, 2024.
Final Office Action for U.S. Appl. No. 17/446,654 mailed Jan. 31, 2024.
Final Office Action for U.S. Appl. No. 17/447,123 mailed May 14, 2024.
Final Office Action for U.S. Appl. No. 17/451,345 mailed Apr. 18, 2024.
Final Office Action for U.S. Appl. No. 17/808,354 mailed Apr. 10, 2024.
Final Office Action for U.S. Appl. No. 18/140,163 mailed Mar. 27, 2024.
International Search Report and Written Opinion from International Application No. PCT/US2023/025192 mailed Feb. 7, 2024.
International Search Report and Written Opinion from International Application No. PCT/US2023/025939 mailed Feb. 7, 2024.
International Search Report and Written Opinion from International Application No. PCT/US2023/030365 mailed Mar. 13, 2024.
International Search Report and Written Opinion from International Application No. PCT/US2023/030373 mailed Mar. 13, 2024.

International Search Report and Written Opinion from International Application No. PCT/US2023/031433 mailed Mar. 4, 2024.
International Search Report and Written Opinion from International Application No. PCT/US2023/031740 mailed Mar. 4, 2024.
International Search Report and Written Opinion from International Application No. PCT/US2023/077208 mailed May 10, 2024.
Issue Notification for U.S. Appl. No. 16/449,039 mailed Jun. 19, 2024.
Issue Notification for U.S. Appl. No. 17/051,550 mailed Mar. 13, 2024.
Issue Notification for U.S. Appl. No. 17/051,554 mailed Mar. 6, 2024.
Issue Notification for U.S. Appl. No. 17/657,474 mailed Jun. 19, 2024.
Issue Notification for U.S. Appl. No. 18/299,788 mailed Feb. 21, 2024.
Non-Final Office Action for U.S. Appl. No. 16/369,676 mailed Feb. 29, 2024.
Non-Final Office Action for U.S. Appl. No. 16/433,773 mailed Feb. 26, 2024.
Non-Final Office Action for U.S. Appl. No. 16/452,258 mailed Jun. 20, 2024.
Non-Final Office Action for U.S. Appl. No. 16/904,868 mailed Mar. 12, 2024.
Non-Final Office Action for U.S. Appl. No. 17/179,116 mailed Feb. 26, 2024.
Non-Final Office Action for U.S. Appl. No. 17/446,256 mailed Feb. 13, 2024.
Non-Final Office Action for U.S. Appl. No. 17/446,654 mailed Jun. 25, 2024.
Non-Final Office Action for U.S. Appl. No. 17/450,864 mailed May 29, 2024.
Non-Final Office Action for U.S. Appl. No. 17/451,354 mailed Apr. 4, 2024.
Non-Final Office Action for U.S. Appl. No. 17/595,747 mailed Jun. 7, 2024.
Non-Final Office Action for U.S. Appl. No. 17/597,673 mailed Mar. 20, 2024.
Non-Final Office Action for U.S. Appl. No. 17/646,771 mailed Apr. 24, 2024.
Non-Final Office Action for U.S. Appl. No. 17/653,920 mailed Mar. 15, 2024.
Non-Final Office Action for U.S. Appl. No. 17/655,464 mailed Mar. 26, 2024.
Non-Final Office Action for U.S. Appl. No. 17/661,090 mailed May 22, 2024.
Non-Final Office Action for U.S. Appl. No. 17/663,330 mailed Jul. 1, 2024.
Non-Final Office Action for U.S. Appl. No. 17/664,487 mailed Jun. 17, 2024.
Non-Final Office Action for U.S. Appl. No. 17/664,914 mailed Jan. 31, 2024.
Non-Final Office Action for U.S. Appl. No. 18/003,029 mailed Mar. 26, 2024.
Non-Final Office Action for U.S. Appl. No. 18/134,857 mailed Jan. 25, 2024.
Non-Final Office Action for U.S. Appl. No. 18/140,751 mailed Jun. 21, 2024.
Non-Final Office Action for U.S. Appl. No. 18/164,800 mailed Mar. 22, 2024.
Non-Final Office Action for U.S. Appl. No. 18/389,009 mailed May 24, 2024.
Notice of Allowance for U.S. Appl. No. 16/369,676 mailed Jun. 17, 2024.
Notice of Allowance for U.S. Appl. No. 16/449,039 mailed Mar. 28, 2024.
Notice of Allowance for U.S. Appl. No. 17/051,550 mailed Feb. 7, 2024.
Notice of Allowance for U.S. Appl. No. 17/326,980 mailed Apr. 5, 2024.
Notice of Allowance for U.S. Appl. No. 17/326,980 mailed Jan. 29, 2024.

(56) References Cited

OTHER PUBLICATIONS

Notice of Allowance for U.S. Appl. No. 17/448,811 mailed Jun. 14, 2024.
Notice of Allowance for U.S. Appl. No. 17/453,260 mailed Apr. 8, 2024.
Notice of Allowance for U.S. Appl. No. 17/453,560 mailed Jan. 31, 2024.
Notice of Allowance for U.S. Appl. No. 17/657,474 mailed Mar. 5, 2024.
Notice of Allowance for U.S. Appl. No. 17/657,474 mailed May 2, 2024.
Notice of Allowance for U.S. Appl. No. 17/662,700 mailed Jun. 12, 2024.
Notice of Allowance for U.S. Appl. No. 17/662,700 mailed Mar. 6, 2024.
Notice of Allowance for U.S. Appl. No. 18/198,464 mailed Apr. 17, 2024.
Restriction Requirement for U.S. Appl. No. 17/527,769 mailed Jun. 17, 2024.
Restriction Requirement for U.S. Appl. No. 17/667,097 mailed Mar. 20, 2024.
Supplemental Notice of Allowance for U.S. Appl. No. 17/051,550 mailed Feb. 21, 2024.
Supplemental Notice of Allowance for U.S. Appl. No. 17/051,554 mailed Feb. 14, 2024.
U.S. Appl. No. 17/444,792, filed Aug. 10, 2021.
U.S. Appl. No. 18/249,577, filed Oct. 19, 2021.
U.S. Appl. No. 18/294,370, filed Feb. 1, 2024.
U.S. Appl. No. 18/294,403, filed Feb. 1, 2024.
U.S. Appl. No. 18/426,795, filed Jan. 30, 2024.
U.S. Appl. No. 18/584,002, filed Feb. 22, 2024.
U.S. Appl. No. 18/610,523, filed Mar. 20, 2024.
U.S. Appl. No. 18/662,216, filed May 13, 2024.
U.S. Appl. No. 18/681,987, filed Feb. 7, 2024.
U.S. Appl. No. 18/682,006, filed Feb. 7, 2024.
U.S. Appl. No. 18/687,117, filed Feb. 27, 2024.
U.S. Appl. No. 18/688,023, filed Feb. 29, 2024.
U.S. Appl. No. 18/693,638, filed Mar. 20, 2024.
U.S. Appl. No. 18/694,090, filed Mar. 21, 2024.
U.S. Appl. No. 18/757,964, filed Jun. 28, 2024.
U.S. Appl. No. 18/758,025, filed Jun. 28, 2024.
U.S. Appl. No. 63/561,893, filed Dec. 11, 2023.
"Oblong", Cambridge Dictionary, https://dictionary.cambridge.org/dictionary/english/oblong, 2024, 1 page.
Britannica, "Polyolefin", Britannica Online Encyclopedia, T. Editors of Encyclopaedia, https://www.britannica.com/science/polyolefin, Jul. 26, 2012.
Martin, et al., "Chapter 5 Applications of Polyethylene Oxide (POLYOX) in Hydrophilic Matrices", Hydrophilic Matrix Tablets for Oral Controlled Release, AAPS Advances in the Pharmaceutical Sciences vol. 16, 2014, pp. 123-141.
Wikipedia Article, "Decibel", https://web.archive.org/web/2020041521917/https://en.wikipedia/org/wiki/Decibel last accessed Mar. 11, 2024, 21 pages.
Wikipedia Article, "Fiberglass", https://web.archive.org.web/20200309194847/https://en.wikipedia.org/wiki/Fiberglass last accessed Mar. 11, 2024.
Advisory Action for U.S. Appl. No. 17/051,585 mailed Oct. 8, 2024.
Advisory Action for U.S. Appl. No. 17/446,256 mailed Nov. 19, 2024.
Advisory Action for U.S. Appl. No. 17/653,137 mailed Nov. 20, 2024.
Advisory Action for U.S. Appl. No. 17/653,920 mailed Oct. 28, 2024.
Advisory Action for U.S. Appl. No. 18/134,857 mailed Oct. 23, 2024.
Corrected Notice of Allowability for U.S. Appl. No. 17/450,864 mailed Oct. 24, 2024.
Corrected Notice of Allowability for U.S. Appl. No. 18/426,795 mailed Dec. 4, 2024.

Final Office Action for U.S. Appl. No. 16/433,773 mailed Sep. 9, 2024.
Final Office Action for U.S. Appl. No. 17/446,654 mailed Dec. 18, 2024.
Final Office Action for U.S. Appl. No. 17/451,354 mailed Oct. 28, 2024.
Final Office Action for U.S. Appl. No. 17/597,673 mailed Oct. 22, 2024.
Final Office Action for U.S. Appl. No. 17/655,464 mailed Nov. 29, 2024.
Final Office Action for U.S. Appl. No. 18/003,029 mailed Oct. 22, 2024.
Final Office Action for U.S. Appl. No. 18/164,800 mailed Oct. 22, 2024.
Final Office Acton for U.S. Appl. No. 17/595,747 mailed Dec. 12, 2024.
International Search Report and Written Opinion from International Application No. PCT/US2023/085516 mailed Aug. 26, 2024.
Issue Notification for U.S. Appl. No. 16/369,676 mailed Oct. 2, 2024.
Issue Notification for U.S. Appl. No. 16/452,145 mailed Oct. 23, 2024.
Issue Notification for U.S. Appl. No. 17/179,116 mailed Dec. 25, 2024.
Issue Notification for U.S. Appl. No. 17/447,123 mailed Nov. 13, 2024.
Issue Notification for U.S. Appl. No. 17/662,700 mailed Oct. 23, 2024.
Issue Notification for U.S. Appl. No. 17/664,914 mailed Nov. 6, 2024.
Issue Notification for U.S. Appl. No. 17/667,097 mailed Dec. 11, 2024.
Issue Notification for U.S. Appl. No. 18/140,163 mailed Dec. 4, 2024.
Issue Notification for U.S. Appl. No. 18/198,464 mailed Nov. 20, 2024.
Issue Notification for U.S. Appl. No. 18/389,009 mailed Dec. 18, 2024.
Non-Final Office Action for U.S. Appl. No. 17/444,792 mailed Oct. 30, 2024.
Non-Final Office Action for U.S. Appl. No. 17/446,256 mailed Dec. 13, 2024.
Non-Final Office Action for U.S. Appl. No. 17/614,173 mailed Sep. 24, 2024.
Non-Final Office Action for U.S. Appl. No. 17/625,941 mailed Nov. 4, 2024.
Non-Final Office Action for U.S. Appl. No. 17/628,411 mailed Sep. 23, 2024.
Non-Final Office Action for U.S. Appl. No. 17/653,920 mailed Nov. 27, 2024.
Non-Final Office Action for U.S. Appl. No. 17/757,311 mailed Oct. 22, 2024.
Non-Final Office Action for U.S. Appl. No. 17/759,697 mailed Dec. 4, 2024.
Non-Final Office Action for U.S. Appl. No. 17/808,354 mailed Dec. 13, 2024.
Non-Final Office Action for U.S. Appl. No. 17/907,125 mailed Dec. 13, 2024.
Non-Final Office Action for U.S. Appl. No. 18/584,002 mailed Sep. 19, 2024.
Notice of Allowance for U.S. Appl. No. 16/478,180 mailed Dec. 16, 2024.
Notice of Allowance for U.S. Appl. No. 16/904,868 mailed Sep. 29, 2024.
Notice of Allowance for U.S. Appl. No. 17/051,585 mailed Dec. 26, 2024.
Notice of Allowance for U.S. Appl. No. 17/179,116 mailed Sep. 13, 2024.
Notice of Allowance for U.S. Appl. No. 17/450,864 mailed Sep. 18, 2024.
Notice of Allowance for U.S. Appl. No. 17/501,591 mailed Nov. 20, 2024.

(56) References Cited

OTHER PUBLICATIONS

Notice of Allowance for U.S. Appl. No. 17/527,769 mailed Nov. 20, 2024.
Notice of Allowance for U.S. Appl. No. 17/646,771 mailed Dec. 17, 2024.
Notice of Allowance for U.S. Appl. No. 17/661,090 mailed Oct. 30, 2024.
Notice of Allowance for U.S. Appl. No. 17/663,330 mailed Nov. 20, 2024.
Notice of Allowance for U.S. Appl. No. 18/140,751 mailed Nov. 1, 2024.
Notice of Allowance for U.S. Appl. No. 18/415,080 mailed Dec. 30, 2024.
Notice of Allowance for U.S. Appl. No. 18/426,795 mailed Nov. 20, 2024.
Restriction Requirement for U.S. Appl. No. 17/596,629 mailed Sep. 19, 2024.
Restriction Requirement for U.S. Appl. No. 17/754,736 mailed Nov. 20, 2024.
Restriction Requirement for U.S. Appl. No. 17/756,201 mailed Oct. 4, 2024.
Restriction Requirement for U.S. Appl. No. 17/758,152 mailed Nov. 5, 2024.
Restriction Requirement for U.S. Appl. No. 17/878,268 mailed Sep. 20, 2024.
Restriction Requirement for U.S. Appl. No. 17/809,083 mailed Dec. 31, 2024.
U.S. Appl. No. 18/828,559, filed Sep. 9, 2024.
U.S. Appl. No. 18/851,197, filed Sep. 26, 2024.
U.S. Appl. No. 18/886,306, filed Sep. 16, 2024.
U.S. Appl. No. 18/903,592, filed Oct. 1, 2024.
U.S. Appl. No. 18/925,921, filed Oct. 24, 2024.
U.S. Appl. No. 18/930,014, filed Oct. 29, 2024.
U.S. Appl. No. 18/931,853, filed Oct. 30, 2024.
U.S. Appl. No. 18/951,944, filed Nov. 19, 2024.
U.S. Appl. No. 18/957,011, filed Nov. 22, 2024.
U.S. Appl. No. 18/974,367, filed Dec. 9, 2024.
U.S. Appl. No. 18/982,930, filed Dec. 16, 2024.
U.S. Appl. No. 63/564,696, filed Mar. 13, 2024.
U.S. Appl. No. 63/711,438, filed Oct. 24, 2024.

U.S. Appl. No. 63/711,445, filed Oct. 24, 2024.
U.S. Appl. No. 63/720,004, filed Nov. 13, 2024.
"Dictionary.com, ABUT Definition and Meaning", Dictionary.com, https://www.dictionary.com/browse/abut, 2024, 1 page.
Corrected Notice of Allowability for U.S. Appl. No. 17/501,591 mailed Aug. 9, 2024.
Corrected Notice of Allowability for U.S. Appl. No. 17/664,914 mailed Aug. 9, 2024.
Final Office Action for U.S. Appl. No. 17/653,920 mailed Aug. 14, 2024.
Final Office Action for U.S. Appl. No. 18/134,857 mailed Jul. 25, 2024.
International Search Report and Written Opinion from International Application No. PCT/US2023/036238 mailed Jul. 22, 2024.
International Search Report and Written Opinion from International Application No. PCT/US2023/080680 mailed Jul. 22, 2024.
Non-Final Office Action for U.S. Appl. No. 17/451,345 mailed Jul. 25, 2024.
Non-Final Office Action for U.S. Appl. No. 17/597,408 mailed Aug. 15, 2024.
Non-Final Office Action for U.S. Appl. No. 17/653,314 mailed Aug. 29, 2024.
Non-Final Office Action for U.S. Appl. No. 17/749,340 mailed Aug. 14, 2024.
Non-Final Office Action for U.S. Appl. No. 17/758,316 mailed Aug. 28, 2024.
Non-Final Office Action for U.S. Appl. No. 18/139,523 mailed Aug. 26, 2024.
Non-Final Office Action for U.S. Appl. No. 18/426,795 mailed Aug. 9, 2024.
Notice of Allowance for U.S. Appl. No. 17/667,097 mailed Aug. 28, 2024.
Notice of Allowance for U.S. Appl. No. 18/140,163 mailed Aug. 21, 2024.
Notice of Allowance for U.S. Appl. No. 18/389,009 mailed Aug. 28, 2024.
U.S. Appl. No. 17/013,822, filed Sep. 7, 2020.
U.S. Appl. No. 18/841,630, filed Aug. 26, 2024.
U.S. Appl. No. 63/568,615, filed Mar. 22, 2024.
U.S. Appl. No. 63/683,428, filed Aug. 15, 2024.

* cited by examiner

MALE EXTERNAL CATHETER WITH ATTACHMENT INTERFACE CONFIGURED TO BIAS AGAINST PENIS

CROSS-REFERENCE TO RELATED APPLICATIONS

This application claims priority to U.S. Provisional Application No. 63/133,892 filed on Jan. 5, 2021, the disclosure of which is incorporated herein, in its entirety, by this reference.

BACKGROUND

In various circumstances, a person or animal may have limited or impaired mobility such that typical urination processes are challenging or impossible. For example, a person may experience or have a disability that impairs mobility. A person may have restricted travel conditions such as those experienced by pilots, drivers, and workers in hazardous areas. Additionally, sometimes urine collection is needed for monitoring purposes or clinical testing.

Urinary catheters, such as a Foley catheter, can be used to address some of these circumstances, such as incontinence. Unfortunately, however, urinary catheters can be uncomfortable, painful, and can lead to complications, such as infections. Additionally, bed pans, which are receptacles used for the toileting of bedridden patients, such as those in a health care facility, are sometimes used. Bed pans, however, can be prone to discomfort, spills, and other hygiene issues. Males who can suffer severe consequences of urinary incontinence, such as discomfort, rashes, and sores are typically elderly and often bedbound. They also require continuous assistance to maintain hygiene. Characteristics often found in these patients: they typically lay on their back, the size of the penis often decreases with age, skin rolls containing fat tissue cause the penis to recede, often pointing upward while in a laying position, patients have difficulty reaching the penis and manipulating devices.

SUMMARY

Embodiments for attachment interfaces and methodologies disclosed herein improve upon conventional devices and methods for attaching urine collection devices to a subject's penis. The devices disclosed herein enable improved attachment to the penis while still allowing for easy removal without injury or irritation to the subject. In an embodiment, a male urine collection device for collection of urine discharged from a subject is disclosed. The male urine collection device includes a receptacle defining an internal volume, the receptacle configured to receive a penis and to collect urine, and a plurality of flaps movable to access the internal volume of the receptacle. The plurality of flaps are configured to bias against the penis when the penis is at least partially received by the receptacle.

In an embodiment, a male urine collection device for collection of urine discharged from a penis is disclosed. The male urine collection device includes a receptacle defining an internal volume, the receptacle configured to collect urine, and a clamshell having two halves movable with respect to each other via a hinge, the clamshell configured to close around the penis to secure the receptacle about the penis when the penis is at least partially received by the receptacle. The clamshell is removably secured to the penis via friction.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the present disclosure, wherein identical reference numerals refer to identical or similar elements or features in different views or embodiments shown in the drawings.

DETAILED DESCRIPTION

Embodiments for attachment interfaces and methodologies disclosed herein improve upon conventional devices and methods for attaching urine collection devices, such as male external catheters, to a subject's penis. The devices disclosed herein enable improved attachment to the penis while still allowing for easy removal without injury or irritation to the subject. A urine collection device is disclosed that is suitable for collecting and transporting urine away from the body of a person or other animal, particularly a male. The disclosed urine collection device includes a urine collecting assembly that can include an attachment interface for improved functionality and securement to the penis.

In some embodiments, the attachment interface includes a plurality of flaps that can surround the penis to removably secure to the penis. In some embodiments, the attachment interface can include a clamshell device configured to lightly clamp onto the penis. The urine collection device can further include a fluid receptacle configured to collect urine from a subject. The attachment interfaces described herein can at least partially define the receptacle. For example, the attachment interface can define one or more walls of the receptacle. The receptacle also includes a fluid outlet in fluid communication with an outlet tube that may be, for example, in fluid communication with a vacuum pump. The urine collection device can be configured to receive a user's penis such that the urethral opening of the penis is disposed within the receptacle (e.g., disposed within the interior region of the receptacle) and the shaft of the penis is in sealing relationship with a peripheral edge of an opening defined by the attachment interface such that the urine collection device is configured to receive urine discharged from the urethral opening into the receptacle, and to have the received urine withdrawn from the receptacle via the outlet.

Examples of male urine collection devices that are configured to collected bodily fluids from a male urethral opening and methods of using such fluid collection assemblies are disclosed in International Application No. PCT/US2020/42262 filed on Jul. 14, 2020, U.S. Patent Publication No. 2019/0282391 filed on Jun. 6, 2019, U.S. Pat. No. 10,376,406 patented on Aug. 13, 2019, and U.S. Provisional Patent Application No. 63/067,542 filed on Aug. 19, 2020, the disclosure of each of which is incorporated herein, in its entirety, by this reference. Other embodiments of fluid impermeable barriers, fluid permeable membranes, fluid permeable supports, chambers, and their shapes and configurations are disclosed in U.S. patent application Ser. No. 15/612,325 filed on Jun. 2, 2017; U.S. patent application Ser. No. 15/260,103 filed on Sep. 8, 2016; and U.S. Pat. No. 10,225,376 filed on Jun. 1, 2017, the disclosure of each of which is incorporated herein, in its entirety, by this reference.

Figure 1A:
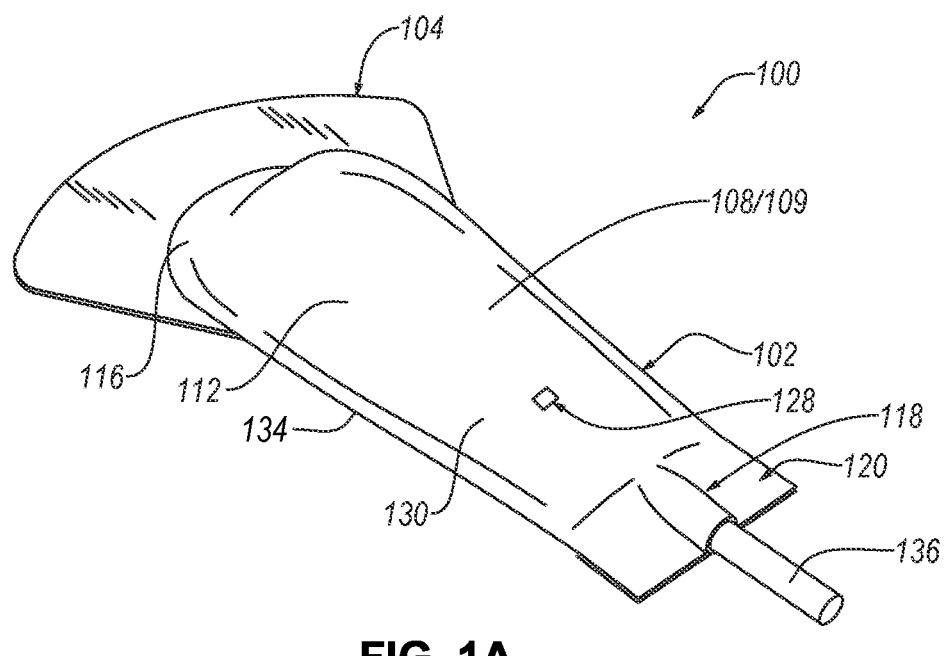
FIGS. 1A and 1B are top and bottom isometric views, respectively, of a male urine collection device, according to an embodiment.
Figure 1B:
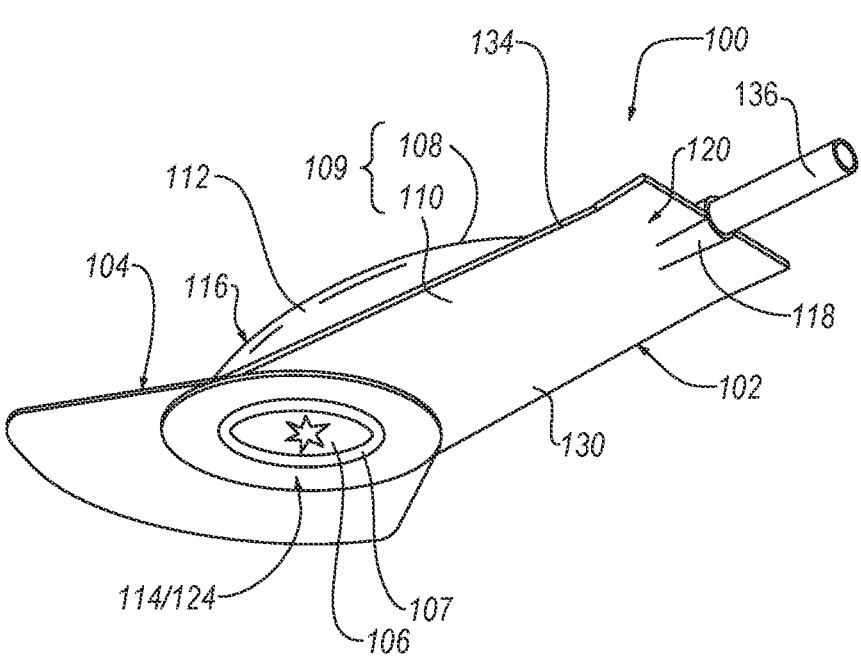

FIGS. 1A and 1B are isometric top and bottom views, respectively, of a urine collection device 100, according to an embodiment. The urine collection device 100 includes a sheath 102 and a base 104. The sheath 102 includes a fluid impermeable barrier 109 that is at least partially formed from a first panel 108 attached to a second panel 110. In an embodiment, as illustrated, the first panel 108 and the second panel 110 are distinct sheets. The fluid impermeable barrier 109 also defines a chamber 112 between the first panel 108 and the second panel 110, an opening 114 at a proximal end region 116 of the sheath 102, and an outlet 118 at a distal end region 120 of the sheath 102. The sheath 102 also includes at least one porous material disposed in the chamber 112. The base 104 includes an aperture 124. The base 104 is permanently attached to the proximal end region 116 of the sheath 102 such that the aperture 124 is aligned with the opening 114. Permanently attached means that the sheath 102 cannot be detached from the base 104 without damaging at least one of the sheath 102 or the base 104, using a blade to separate the sheath 102 from the base 104, and/or using chemicals to dissolve the adhesive that attaches the sheath 102 from the base 104.

The inner surfaces 126 of the fluid impermeable barrier 109 (e.g., inner surfaces of the first and second panels 108, 110) at least partially defines the chamber 112 within the urine collection device 100. The fluid impermeable barrier 109 temporarily stores the bodily fluids in the chamber 112. The fluid impermeable barrier 109 may be formed of any suitable fluid impermeable material(s), such as a fluid impermeable polymer (e.g., silicone, polypropylene, polyethylene, polyethylene terephthalate, a polycarbonate, etc.), a metal film, natural rubber, another suitable material, or combinations thereof. As such, the fluid impermeable barrier 109 substantially prevents the bodily fluids from passing through the fluid impermeable barrier 109. In an example, the fluid impermeable barrier 109 may be air permeable and fluid impermeable thus preventing leaks while allowing air flow through the chamber 112 when a suction force is applied thereto (i.e., the chamber 112 remains at about atmospheric pressure thereby preventing the suction force from causing a bruise or kinking the conduit 136). In such an example, the fluid impermeable barrier 109 may be formed of a hydrophobic material that defines a plurality of pores. Alternatively or additionally, the fluid impermeable barrier 109 may include at least one perforation 128 (e.g., vacuum relief hole) that allows the chamber 112 to remain substantially at atmospheric pressure. At least one or more portions of at least an outer surface 130 of the fluid impermeable barrier 109 may be formed from a soft and/or smooth material, thereby reducing chaffing.

In an embodiment, at least one of the first panel 108 or the second panel 110 is formed from an at least partially transparent fluid impermeable material, such as polyethylene, polypropylene, polycarbonate, or polyvinyl chloride. Forming at least one of the first panel 108 or the second panel 110 from an at least partially transparent fluid impermeable material allows a person (e.g., medical practitioner) to examiner the penis. In some embodiments, both the first panel 108 and the second panel 110 are formed from at least partially transparent fluid impermeable material. For example, some conventional fluid collection assemblies that include a sheath and a base may allow the sheath to be reversibly detached from the base after the base is secured to the region about the penis. Detaching the sheath from the base allows the person to examine the penis. However, configuring the sheath to be detachable from the base may allow leaks between the sheath and the base. As previously discussed, the sheath 102 is permanently attached to the base 104 which substantially prevents leaks between the sheath 102 and the base 104 when the base 104 is appropriately attached to the sheath 102 (e.g., no wrinkles were allowed to form between the sheath 102 and base 104). Selecting at least one of the first panel 108 or the second panel 110 to be formed from an at least partially transparent impermeable material allows the penis to be examined without detaching the entire urine collection device 100 from the region about the penis. For example, the chamber 112 may include a penis receiving area 132 that is configured to receive the penis of the individual when the penis extends into the chamber 112.

The porous material in the chamber 112 may include permeable material designed to wick or pass fluid therethrough. Suitable permeable or porous materials can include spun nylon fibers. The permeable properties referred to herein may be wicking, capillary action, diffusion, or other similar properties or processes, and are referred to herein as "permeable" and/or "wicking." Such "wicking" may not include absorption of fluid into the wicking material. Put another way, substantially no absorption of fluid into the material may take place after the material is exposed to the fluid and removed from the fluid for a time. While no absorption is desired, the term "substantially no absorption" may allow for nominal amounts of absorption of fluid into the wicking material (e.g., absorbency), such as less than about 30 wt % of the dry weight of the wicking material, less than about 20 wt %, less than about 10 wt %, less than about 7 wt %, less than about 5 wt %, less than about 2 wt %, or less than about 0.5 wt % of the dry weight of the wicking material. Wicking material can include natural fibers. In such examples, the material may have a coating to prevent or limit absorption of fluid into the material, such as a water repellent coating. In an embodiment, the porous material includes a body of spun nylon fibers with an outer permeable membrane made of fabric such as gauze.

The penis receiving area 132 may be defined by at least the porous material and at least a portion of the at least partially transparent material of the first panel 108 and/or the second panel 110. In other words, the porous material is positioned in the chamber 112 such that the porous material is not positioned between the penis and at least a portion of the transparent portion of the first panel 108 and/or second panel 110 when the penis is inserted into the chamber 112 through the opening 114. The porous material is generally not transparent and, thus, the portion of the at least partially transparent material of the first panel 108 and/or the second panel 110 that defines the penis receiving area 132 forms a window which allows the person to view into the penis receiving area 132 and examine the penis.

In an embodiment, the second panel 110 is at least partially formed from the at least partially transparent material and forms the window that allows the person to view into the penis receiving area 132. Further, the porous material is positioned between the penis receiving area 132 and at least a portion of the first panel 108. Such an embodiment may help maintain the dignity of the individual using the urine collection device 100. For example, during use, the second panel 110 is generally adjacent to the individual, such as adjacent to the thighs and/or perineum. Thus, the second panel 110 is generally obscured during use and a person cannot view the penis without first lifting the sheath 102 away from the individual. Meanwhile, the first panel 108 may face away from the individual and be more easily viewable than the second panel 110. However, a person (e.g., a passerby, a visitor, etc.) cannot view the penis through the first panel 108 because the porous material is not transparent and/or the first panel 108 is formed from a non-transparent material. Thus, in such an embodiment, the first panel 108 and/or the porous material prevent person(s) from viewing the penis unless such examination is necessary, thereby preserving the dignity of the individual using the urine collection device 100. In an embodiment, the first panel 108 is formed from the at least partially transparent material and forms the window that allows the person to view into the penis receiving area 132. Further, the porous material is positioned between the penis receiving area 132 and at least a portion of the second panel 110. In such an embodiment, the person does not need to perform the additional act of lifting the sheath 102 to view into the penis receiving area 132 but may not maintain the dignity of the individual using the urine collection device 100 since passersby may also view into the penis receiving area 132.

As previously discussed, at least a portion of the first panel 108 and at least a portion of the second panel 110 are attached together. In an embodiment, as shown, the first and second panels 108, 110 are attached together along at least a portion of the outer edges 134 thereof. In such an embodiment, the first and second panels 108, 110 are attached using any suitable technique, such as with an adhesive, sewing, heat sealing, radio frequency ("RF") welding, ultrasonic ("US") welding, or any other technique. As will be discussed in more detail below, forming the fluid impermeable barrier 109 from the first panel 108 and the second panel 110 may improve the rate of manufacturing the urine collection device 100, especially when the first panel 108 and the second panel 110 are attached together using a non-sewing technique. In an embodiment, the first panel 108 and the second panel 110 can be a single unitary piece, such as a tube.

The opening 114 defined by the fluid impermeable barrier 109 provides an ingress route for fluids to enter the chamber 112 when the penis is a buried penis and allow the penis to enter the chamber 112 (e.g., the penis receiving area 132) when the penis is not buried. The opening 114 may be defined by the fluid impermeable barrier 109 (e.g., an inner edge of the fluid impermeable barrier 109). For example, the opening 114 is formed in and extends through the fluid impermeable barrier 109, from the outer surface 130 to the inner surface 126, thereby enabling bodily fluids to enter the chamber 112 from outside of the urine collection device 100.

In an embodiment, the urine collection device 100 includes one or more attachment interfaces 106, 107 disposed in or about the opening 114. The attachment interfaces 106, 107 can be the same or similar to any of the attachment interfaces disclosed herein, for example, the attachment interface 106 can be substantially similar to the attachment interface 306 and the attachment interface 107 (also referred to as a clamshell), can be substantially similar to the attachment interface 407 as described below. As discussed below, the attachment interfaces 106, 107 can be used to provide improve attachment of the urine collection device 100 to the penis of the subject. It will be appreciated that the attachment interfaces 106, 107 can be used with a wide variety of urine collection devices and the embodiment shown in FIG. 1B is non-limiting. Further examples of attachment interfaces being implemented on urine collection devices are provided below with reference to FIGS. 2A and 2B.

Figure 2A:
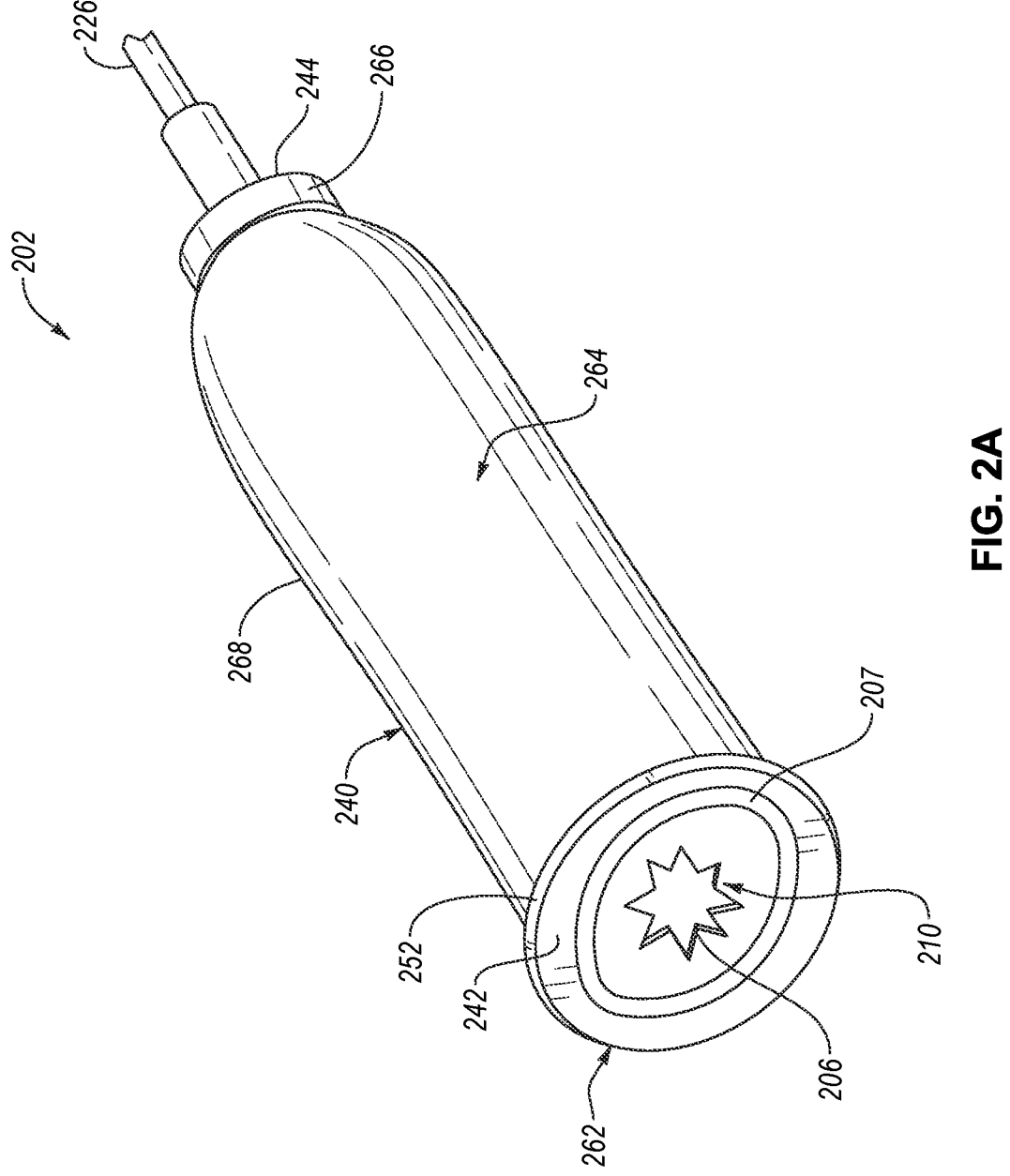
FIG. 2A is an isometric view of a male urine collection device, according to an embodiment.

FIG. 2A is an isometric view of a urine collection device 202, according to an embodiment. The urine collection device 202 can be similar to any of the urine collection devices disclosed herein. For example, the urine collection device 202 can include a body 240 having an open proximal end 242 and an at least partially closed distal end 244, a reservoir 210 at least partially defined by the body 240, attachment interfaces 206, 207, and tubing 226 fluidly coupled to the reservoir 210.

The body 240 of the urine collection device 202 can include a ring 262 at or near the open proximal end 242 of the body 240, a sheath 264 extend from or near the open proximal end 242 to or near the at least partially closed distal end 244 of the body 240, and a sump 266 at the at least partially closed distal end 244 of the body 240. In an embodiment, the ring 262, the sheath 264, and the sump 266 are all distinct components from each other. In an embodiment, at least two of the ring 262, the sheath 264, or the sump 266 are integrally formed together (e.g., are formed from a single piece). The sheath 264 is configured to prevent a fluid (e.g., urine) escaping from the reservoir 210 and to move the fluid towards the sump 266 and the tubing 226. The sheath 264 can include a plurality of layers that facilitate the operation of the sheath 264.

The urine collection device 202 can include attachment interfaces 206, 207 located at or near the open proximal end 242 of the body 240. The attachment interfaces 206, 207 can be similar to the attachment interfaces discussed herein, for example, the attachment interface 206 can be substantially similar to the attachment interface 306 and the attachment interface 207 (also referred to as a clamshell), can be substantially similar to the attachment interface 407 as described below. A subject's penis may enter the body 240 of the urine collection device 202 by passing the attachment interfaces 206, 207. The urine collection device 202 may then be securely affixed to the subject's penis via the flaps of the attachment interface 206 and clamshell 207 as discussed herein. Further details of attachment interfaces being incorporated onto urine collection devices are discussed below. Specifically, the remaining figures disclose structural and functional details of the attachment interfaces and highlight the applicability of the attachment interfaces to generic urine collection devices.

Figure 2B:
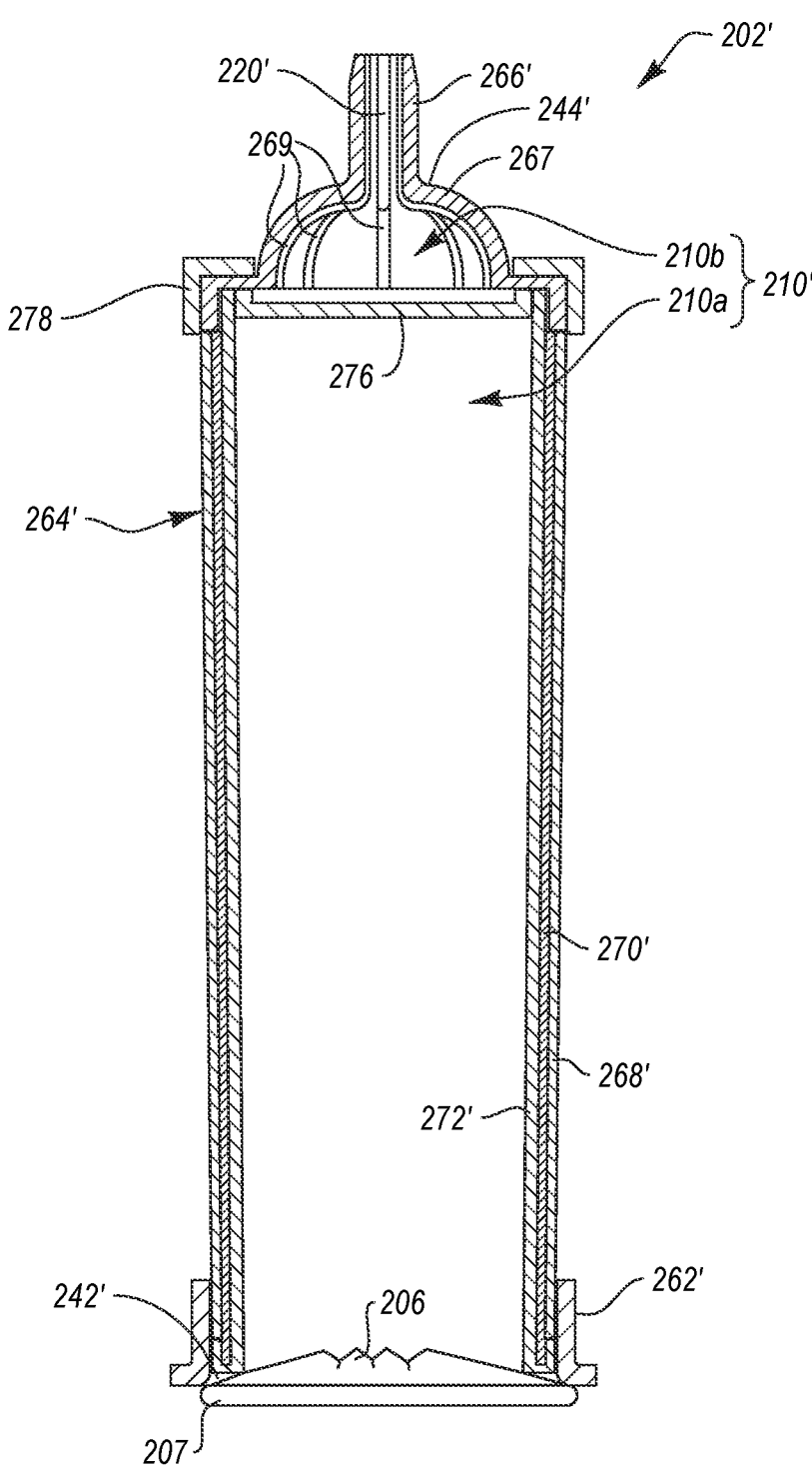
FIG. 2B is a cross-sectional side view of the male urine collection device of FIG. 2A.

FIG. 2B is a cross-sectional side view of a urine collection device 202, according to an embodiment. For example, with reference to FIG. 2B the sheath 264 can include a fluid impermeable layer 268, a fluid permeable layer (e.g., a one-way fluid movement fabric, gauze, or cloth), and a fluid permeable support 272 positioned between the fluid permeable layer and the fluid impermeable layer 268. The fluid permeable support 272 may include a porous layer (e.g., a spun polymer layer. The fluid impermeable layer 268 can form an external surface of the body 240 and prevent the fluid from leaking through the sheath 264. The fluid permeable layer 274 can form an internal surface of the body 240. The fluid permeable layer 274 can be configured to move the fluid from the reservoir 210 to the fluid permeable support 272 and may substantially prevent the fluid that is in the fluid permeable support 272 from flowing back into the reservoir 210. As such, the fluid permeable layer 274 can remove fluid from around a penis thereby leaving the penis dry. The fluid permeable support 272 can form an inner layer between the fluid permeable layer 274 and the fluid impermeable layer 268. The fluid permeable support 272 can enable the fluid to flow generally towards the tubing 226.

It is noted that one or more layers of the sheath 264 can be omitted. For example, the fluid permeable layer 274 can be omitted such that the fluid permeable support 272 forms the internal surface of the body 240. In such an example, the sheath 264 can rely on the wicking ability of the fluid permeable support 272 and a suction force applied to the urine collection device 202 to remove the fluid from the penis. In another example, the sheath 264 only include the fluid impermeable layer 268. In such an example, the sheath 264 can rely on the suction force applied to the urine collection device 202 to remove the fluid from the penis. In another example, the sheath 264 only includes the fluid impermeable layer 268 and the fluid permeable layer 274. In such an example, the sheath 264 can form a channel (not shown) between the fluid impermeable layer 268 and the fluid permeable layer 274 and the channel is fluidly coupled to the tubing 226.

The fluid permeable layer 274 and/or the fluid permeable support 272 may include permeable material designed to wick or pass fluid therethrough. The permeable properties referred to herein may be wicking, capillary action, diffusion, or other similar properties or processes, and are referred to herein as "permeable" and/or "wicking." Such "wicking" may not include absorption of fluid into the wicking material. Put another way, substantially no absorption of fluid into the material may take place after the material is exposed to the fluid and removed from the fluid for a time. While no absorption is desired, the term "substantially no absorption" may allow for nominal amounts of absorption of fluid into the wicking material (e.g., absorbency), such as less than about 10 wt % of the dry weight of the wicking material, less than about 7 wt %, less than about 5 wt %, less than about 3 wt %, less than about 2 wt %, less than about 1 wt %, or less than about 0.5 wt % of the dry weight of the wicking material. Wicking material can include natural fibers. In such examples, the material may have a coating to prevent or limit absorption of fluid into the material, such as a water repellent coating.

The sheath 264 is configured to have a penis disposed therein. To facilitate fluid collection and improve comfort, the sheath 264 can be flexible thereby allowing the sheath 264 to correspond to the shape of a penis. For example, the flexible sheath 264 can at least partially collapse when the penis is not erect and at least partially expand and bend to the shape of the penis as the penis becomes erect. Forming the layers of the sheath 264 from at least one of thin layers (e.g., less than 500 μm thick, and more particularly less than 250 μm thick, less than 100 μm thick, or less than 50 μm thick), flexible layers, or fabric can allow the sheath 264 to be sufficiently flexible.

The ring 262 can be more rigid than the sheath 264. For example, the ring 262 can be formed from a flexible polymer that is at least one of thicker than the entire sheath 264 or exhibits a Young's modulus that is greater than sheath 264. As such, the ring 262 can provide some structure at or near the open proximal end 242. The increased rigidity of the ring 262 can cause the open proximal end 242 to remain open thereby facilitating insertion of a penis into the attachment interface 206 and/or clamshell 207. Further, in an embodiment, the increased rigidity of the ring 262 can enable the ring 262 to act as an attachment mechanism. For example, as illustrated, the ring 262 can be adjacent to or enable placement of the attachment interface 206 and/or the clamshell 207.

The sump 266 is configured to attach the rest of the urine collection device 202 to the tube 226. For example, the sump 266 can define an outlet 220 extending through at least the fluid impermeable layer 268 thereby coupling the tubing 226 to the fluid permeable support 272 and/or the reservoir 210. Further, the sump 266 can close the at least partially closed distal end 244. For example, the sump 266 can bunch up the sheath 264 and close any gaps that may form.

The ring 262, the sheath 264, the sump 266, and attachment interface 206, 200 can be attached together using any suitable method. For example, at least two of the ring 262, the sheath 264, the sump 266, or attachment interfaces 206, 207 can be attached together using at least one of an interference fit, an adhesive, stitching, welding (e.g., ultrasonic welding), tape, any other suitable method, or combinations thereof.

The reservoir 210 may include one or more sections. For example, the reservoir 210 may include a first section 210a that is defined by the sheath 264. However, as illustrated, the reservoir 210 may include one or more additional sections that are defined by one or more additional components of the urine collection device 202. For example, sump 266 may exhibit a bulbous portion 267 extending from an outlet 220 of the sump 266 towards an open proximal end 242 of the sheath 264. The bulbous portion 267 may define a second section 210b of the reservoir 210. The second section 210b may provide a location to store the fluid that is spaced from a penis of a user that is partially disposed in the urine collection device 202. As such, the second section 210b may decrease the amount of fluids that contact the penis.

The sheath 264 extends from or near an open proximal end 242 of the urine collection device 202 to or near an at least partially closed distal end 244 of the urine collection device 202. However, in an embodiment, the portion of the sheath 264 at or near the at least partially closed distal end 244 defines a hole (e.g., opening). In such an embodiment, the urine collection device 202 may include a porous top layer 276 that at least partially covers the hole. The porous top layer 276 may separate the first section 210*a* of the reservoir 210 from the second section 210*b* of the reservoir 210.

The porous top layer 276 may be the same as or substantially similar to any of the fluid impermeable supports or fluid permeable layers disclosed herein. For example, the porous top layer 276 may include a one-way fluid movement fabric, thereby allowing fluid to flow from the first section 210*a* of the reservoir 210 to the second section 210*b* of the reservoir 210 while preventing the fluid from flowing from the second section 210*b* back to the first section 210*a*. As such, the porous top layer 276 may decrease the amount of fluid that contacts the penis when the porous top layer 276 includes the one-way fluid movement fabric. However, it is noted that the porous top layer 276 may include gauze, other types of fabric, or any other suitable porous material instead of or in addition to the one-way fluid movement fabric.

The sump 266 includes a bulbous portion 267. The sump 266 may also include one or more ridges 269 extending from or near the outlet 220 towards the open proximal end 242. In an embodiment, the ridges 269 may direct any fluids that are in the second section 210*b* of the reservoir 210 towards the outlet 220. In an embodiment, the ridges 269 may provide at least some structural support to the bulbous portion 267 such that ridges 269 resist the deformation and/or collapse of the bulbous portion 267. It is noted that the bulbous portion 267 may include one or more structural elements instead of or in addition to the ridges 269. For example, the bulbous portion 267 may define one or more recesses that resist bending stresses.

The sump 266 may be exposed to the atmosphere, which allows the sump 266 to be visible, and may be exposed to an interior of the urine collection device 202. As such, the sump 266 may provide fluid communication between the atmosphere and the interior of the urine collection device 202 and/or provide information. For example, the sump 266 may be formed from a porous material that is configured to assist in suction balance. In an embodiment, the sump 266 may be formed from a material that is configured to change color or state when exposed to bacteria to indicate that an individual using the urine collection device 202 has an infection.

The urine collection device 202 may include an upper ring 278. The upper ring 278 may be configured to be positioned adjacent to the portion of the sump 266 that is connected to the sheath 264. In an embodiment, the upper ring 278 provides additional strength and/or rigidity to the portion of the sump 266 that is connected to the sheath 264. For example, the sheath 264 may be flexible, thereby allowing the sheath 264 to conform to the environment as well as gravity to create a shape that conforms to the anatomy of the individual wearing the urine collection device 202 thus giving the urine collection device 202 an adjustable length. Meanwhile, the upper ring 278 provides some rigidity to the urine collection device 202, thereby inhibiting leakage and patient injuries that the sheath 264, by itself, cannot prevent. In an embodiment, the upper ring 278 may be connected to the sheath 264. In such an embodiment, the upper ring 278 may be connected to the sheath 264 along with the sump 266 thereby increasing the attachment strength between the sheath 264 and the sump 266 or the upper ring 278 may indirectly connect the sump 266 to the sheath 264 (e.g., only the upper ring 278 is directly connected to the sheath 264).

In an embodiment, the upper ring 278 may include a writeable area that is configured to receiving one or more markings thereon, for example, from a pencil or marker. The writeable area of the upper ring 278 may allow medical practitioners to indicate when the urine collection device 202 was disposed on the individual or to indicate other useful information. In an embodiment, the upper ring 278 may include a material that exhibits a color change at or around a certain time after being exposed to air which allows the upper ring 278 to indicate how long the urine collection device 202 has been in use.

Figure 3A:
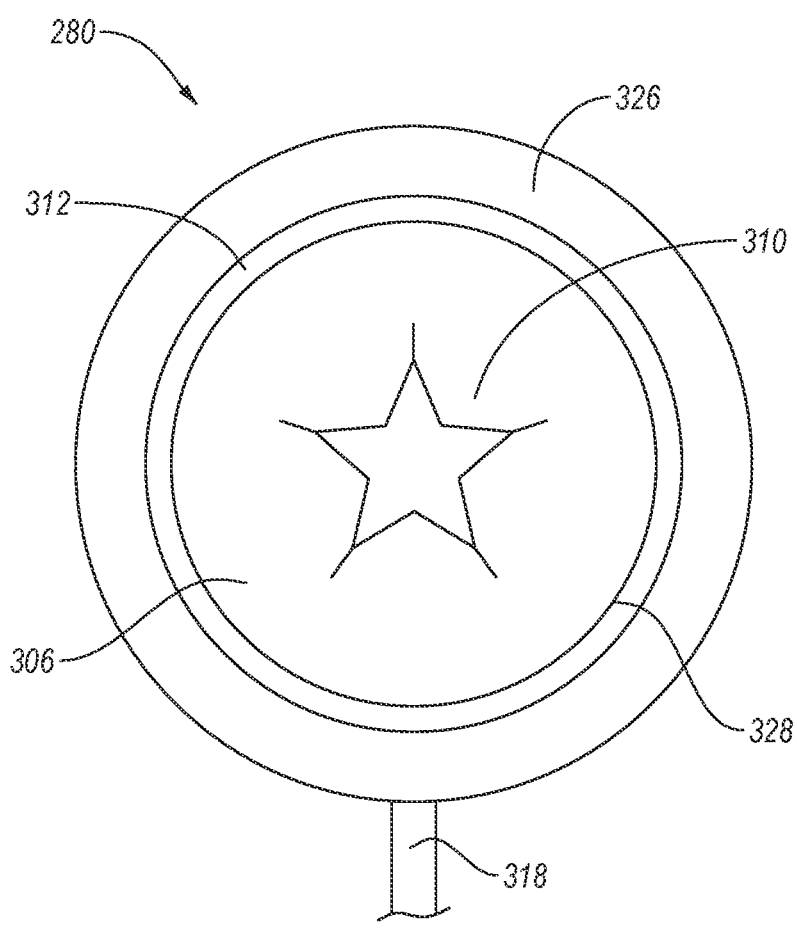
FIG. 3A is a top view of a urine collection device, according to an embodiment.
Figure 3B:
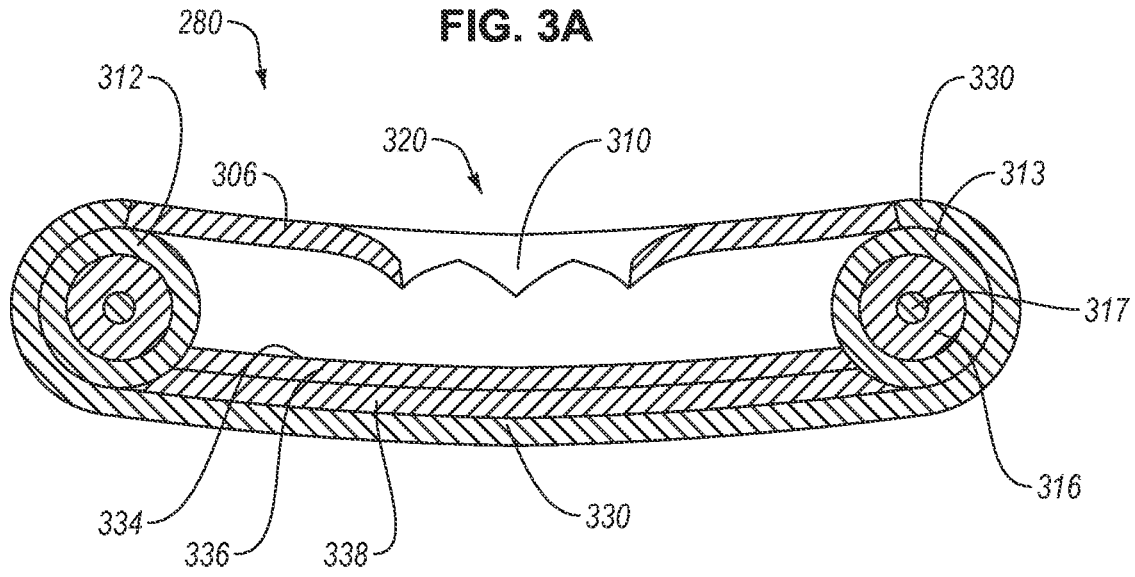
FIG. 3B is a cross-sectional side view of the urine collection device of FIG. 3A.

Referring to FIGS. 34 and 3B, an embodiment of a urine collection device 280 includes a chamber assembly 312. The chamber assembly 312 includes a thin layer of wicking material 313 and a porous material 316. The porous material 316 is configured to form a continuous ring-like chamber 317 in which urine can be collected for transport. The wicking material 313 can be disposed about the porous material 316. The chamber 317 has a port for receiving a tube 318 so that urine collected within the chamber 317 can be transported from the chamber 317 by being drawn from the chamber 317 when a partial vacuum is applied within the chamber 317 via the received tube 318. The received tube 318 can extend within the chamber 317. The chamber assembly 312 is dimensioned and configured to define a perimeter 328. The perimeter 328 can define an opening. An attachment interface 306 comprising a plurality of flaps 310 can extend from the perimeter 328 of the chamber assembly 312 through which the head of a penis can be inserted. The attachment interface 306 can be substantially similar to the attachment interfaces 106 and 206 discussed above.

In another embodiment (not shown), the porous material is configured to form a discontinuous C-shaped chamber in which urine can be collected for transport, with opposing portions of the chamber assembly being sufficiently adjacent as to define an opening through which the head of a penis can be inserted.

As illustrated in FIG. 3B, a flexible sheet of impermeable material 330 is so attached to the chamber assembly 312 to cover one side of the opening formed by the perimeter 328 and thereby provide a receptacle 320 for receiving the head of an inserted penis. Urine flowing into the receptacle 320 from the penis can be drawn through the wicking material 313 and the porous material 316 into the chamber 317 when a partial vacuum is applied within the chamber 317 via the tube 318.

In an embodiment, the sheet of impermeable material 330 is so dimensioned in relation to the breadth of the perimeter 328 as to extend sufficiently away from the chamber assembly 312 to provide adequate space in the receptacle to receive the head of the penis. The attachment interface 306 and the impermeable material 330 can form a volume to house the penis. The layer of impermeable material 330 further covers at least the exterior sides of the chamber assembly 312, The layer of impermeable material 330 can cover a portion of the interior sides of the chamber assembly 312.

The layer of impermeable material 330 can be attached to the chamber assembly 312 by an adhesive material. In another embodiment (not shown), retainer clips or other fasteners attach the impermeable material 330 to the chamber assembly 312. The impermeable material 330 can be integrally formed with the chamber assembly 312. Likewise, the attachment interface 306 can be attached to the chamber assembly 312 by an adhesive or other fastener. The attachment interface 306 can be integrally formed from the chamber assembly 312.

In an embodiment, the urine collection device 280 includes a cushion 334 which is disposed adjacent the impermeable material 330 for receiving the head of an inserted penis. The cushion 334 is so disposed over the layer of impermeable material 330 as to contact the wicking material 313 of the chamber assembly 312. The cushion 334 includes a layer of wicking material 336, such as medical gauze, disposed over a bed of porous material 338.

In an embodiment, the porous material 316 is provided as a web of a, spun plastic material, such as nylon or polyester. In an embodiment, the chamber 317 is formed by folding together opposite sides of a web of spun plastic material, whereby the chamber 317 does not necessarily have a closed cross-section as shown in FIG. 2. In FIGS. 3A and 3B, the relative dimensions of the various components are not necessarily shown to scale.

In operation, when a man's penis is inserted through the flaps 310 of the attachment interface 306, expelled urine can flow between the layer of porous material 338 and the sheet of impermeable material 330 and into the chamber 317 and thence to the outlet tube 318. The urine collection device 280 can thus advantageously capture urine as it flows against gravity without having to attach a catheter to the penis. The attachment interface 306 can further prevent urine from escaping the urine collection device 280 and can direct urine toward the chamber 317.

Figure 4A:
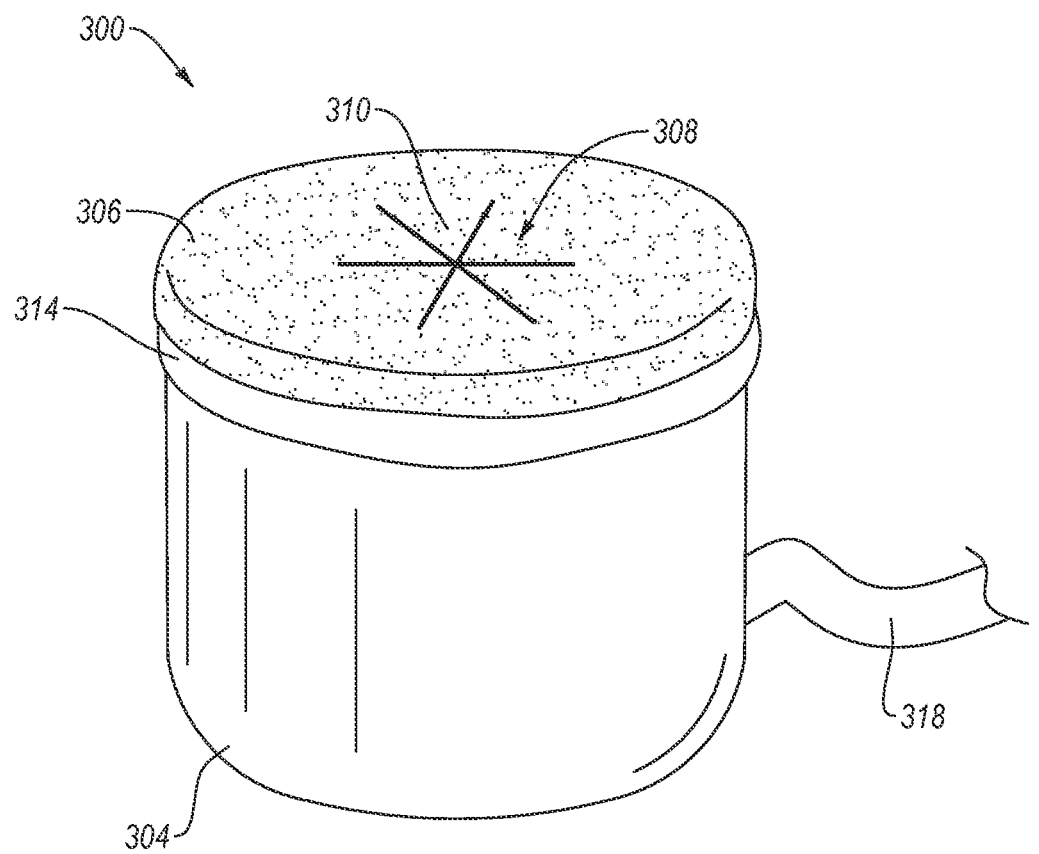
FIG. 4A is an isometric view of a urine collection device, according to an embodiment.

FIG. 4A is an isometric view of a urine collection device 300 (such as a male external catheter), according to an embodiment. The urine collection device 300 can include a receptacle 304 configured to collect urine from a subject. The receptacle 304 can be formed from silicone or other polymer materials. The urine collection device 300 can further include an attachment interface 306 configured to releasably couple to the subject. The attachment interface 306 can be integrally formed with the receptacle 304 or can be a separately formed unit that is coupled to the receptacle 304. For example, the attachment interface 306 can be configured to releasably attach to a penis. The attachment interface 306 can include a plurality of flaps 310 that are formed by one or more slits on the attachment interface 306. The plurality of flaps 310 can form an opening 308 that reveals the interior volume of the receptacle 304. The flaps 310 can be made from a flexible, resilient, and/or elastic material that is configured to retain its shape, such as a polymer material. For example, the flaps can be made from plastics such as polyethylene or polypropylene or from elastomers such as rubber. The flaps 310 can be configured to retain their position after being deformed. In this manner, the flaps 310 can generate an elastic tension against the subject's penis. Thus, a subject's penis can be brought in fluid communication with the interior volume of the receptacle 304 via opening 308. In some embodiments, the urine collection device 300 can include a wicking material 314 positioned proximate the attachment interface 306 within the interior volume of the receptacle 304. The wicking material 314 can be configured to draw fluid away from the opening 308 and the subject's body. For example, the wicking material 314 can be positioned in the V-shaped gaps between the flaps 310 and the subject's penis.

In some embodiments, the internal volume of the receptacle 304 defines an outlet that is in fluid communication with a conduit or tube 318. The tube 318 can be in fluid communication with a vacuum pump configured to draw a vacuum in the receptacle to suck any collected fluid out of the receptacle 304. Further details of the attachment interface 306 are provided below with reference to FIGS. 4 and 5.

Figure 4B:
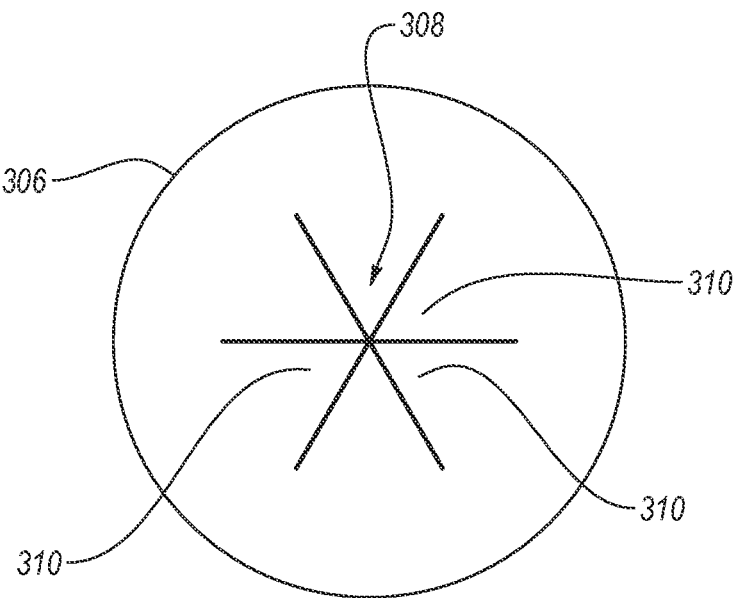
FIG. 4B is a top view of an attachment interface, according to an embodiment.

FIG. 4B is a top view of an example attachment interface 306, according to an embodiment. The attachment interface 306 can include multiple flaps 310 that are formed by slits in the attachment interface 306. The slits allow the flaps to deform, bend, or fold to reveal the opening 308 into the receptacle 304. As shown in FIG. 4B, the slits can be arranged in a star-like pattern. In some embodiments, the flaps 310 are biased toward a neutral or flat position that is in-plane with the attachment interface 306, such that the opening 308 is covered when the flaps 310 are in their natural or unbiased position.

In some embodiments, the attachment interface 306 can include spun plastic. The attachment interface 306 can include multiple layers. In some embodiments, the attachment interface 306 includes an inner layer exposed to the internal volume of the receptacle 304. The inner layer can include a wicking material. The attachment interface 306 can include an outer layer exposed to the outside environment. The outer layer can include a fluid impermeable layer. A middle layer can be disposed between the inner layer and the outer layer. The inner layer can include spun plastic. The flaps 310 can be made from a flexible material that is configured to retain its shape. The flaps 310 can be configured to retain their position after being deformed. In this manner, the flaps 310 can generate an elastic tension against the subject's penis. In some embodiments, the flaps 310 can form a partial or complete seal against the subject's penis. For example, when the subject's penis is inserted through the opening 308. The flaps 310 bias against or press against the shaft of the penis to improve coupling between the receptacle 304 and the penis and to also generate a partial seal between the receptacle and the penis. In some embodiments, the flaps 310 entirely converge such that the opening 308 is entirely covered when the flaps are un-deformed. When the penis is positioned in the opening 308 and the flaps 310 are bent around the shaft of the penis, the shape of the flaps 310 naturally resist the penis exiting the attachment interface 306. In this way, the flaps 310 act as a type of one-way trap, allowing the penis to easily enter the opening 308, while resisting removal of the penis from the opening. However, removal of the penis from the attachment interface 306 can be easily performed and will not result is discomfort or injury to the subject.

Figure 5:
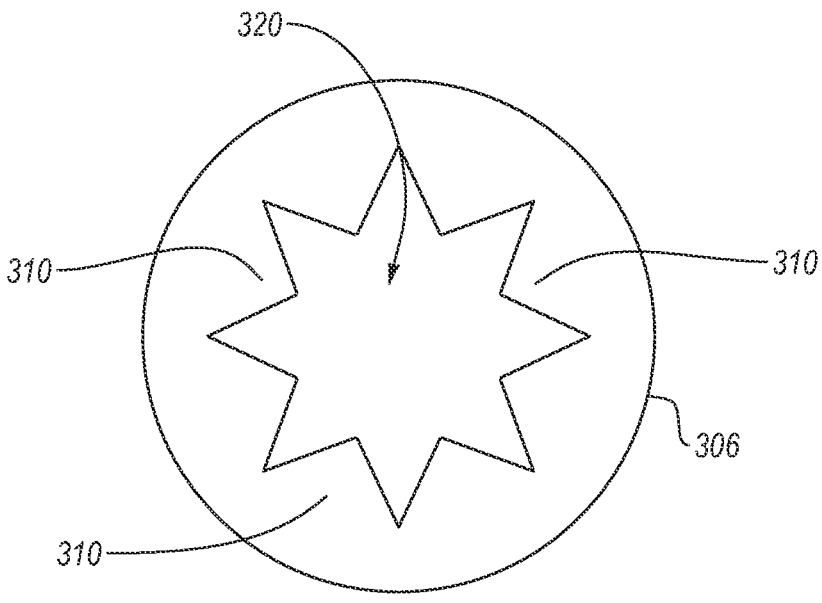
FIG. 5 is a top view of an attachment interface, according to an embodiment.

FIG. 5 is a top view of an example attachment interface 306, according to an embodiment. The attachment interface 306 illustrated in FIG. 5 can be substantially similar to the attachment interface 306 disclosed with reference to FIG. 4B. The attachment interface 306 can include multiple flaps 310 that are formed by slits or cut-outs in the attachment interface 306. As shown in FIG. 5, a star-like cut-out can define an opening 320 into the receptacle 304. In some embodiments, the flaps 310 are biased toward a neutral or flat position. When the flaps 310 are in the neutral or unbiased state the opening 320 can be at a minimum diameter, which is expanded when the flaps 310 are deformed. In the embodiment shown in FIG. 5, the opening 320 remains at least partially exposed even when the flaps are in their unbiased position.

Figure 6:
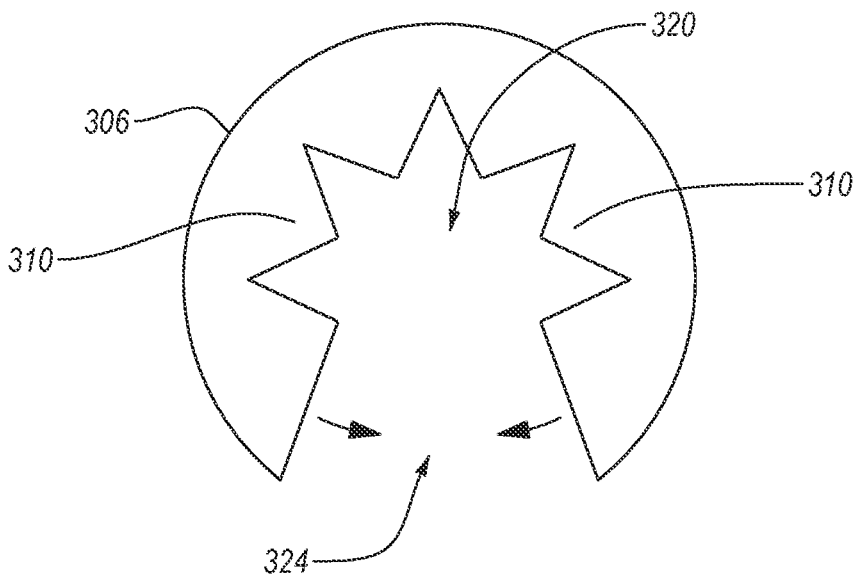
FIG. 6 is a top view of an attachment interface, according to an embodiment.

FIG. 6 illustrates an embodiment of an attachment interface 306 in which two ends of the attachment interface 306 are separated to form a gap 324, according to an embodiment. The gap 324 can be configured to allow a penis to enter the opening 320 through the gap 324. In other words, instead of having the penis enter the opening 320 by inserting the penis passed the flaps 310, the attachment interface 306 can wrap around the penis by permitting passage of the penis into the attachment interface 306. In an open state (i.e., with the gap 324 expanded) the attachment interface 306 can easily be wrapped around the penis, and in a closed state (i.e., with the gap closed or contracted) the penis can be secured within the attachment interface 306. Although the flaps shown herein are generally triangular in shape, it will be understood the other shapes are also possible, for example, the flaps can be semi-circular or rectangular.

Figure 7:
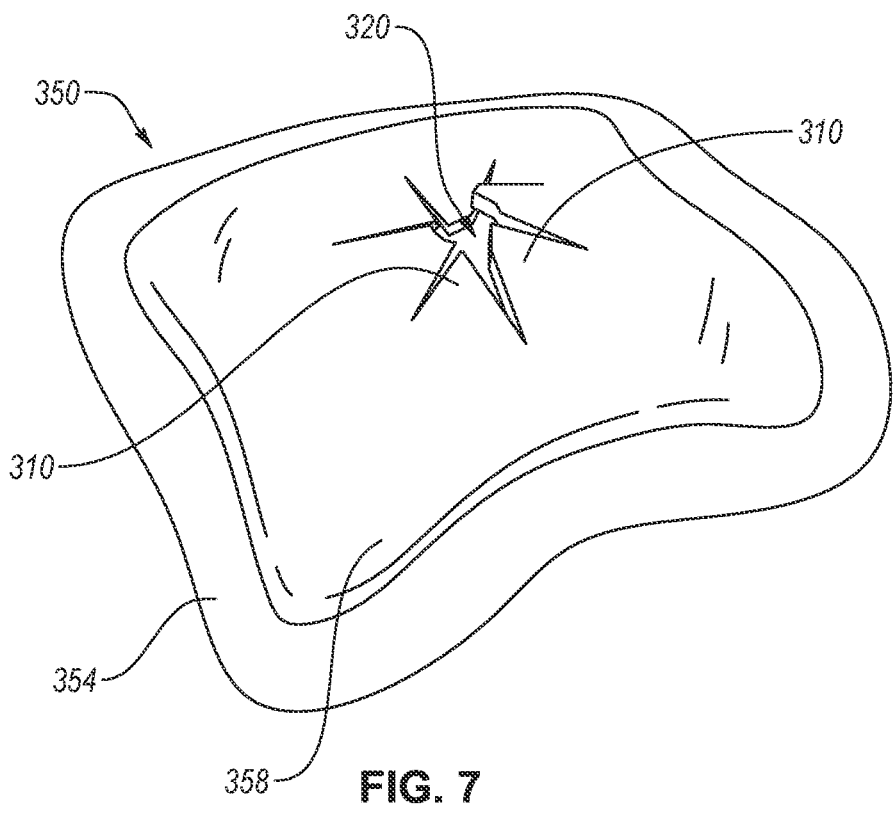
FIG. 7 is an isometric view of a bandage, according to an embodiment.

FIG. 7 illustrates a bandage 350. The bandage 350 can be an attachment interface and can be substantially similar to the attachment interfaces discussed herein, such as the attachment interfaces 306 of FIGS. 3-6, according to an embodiment. The bandage 350 can be configured to operationally couple with a urine collection device, such as with the receptacle 304 of urine collection device 300 discussed above. The bandage 350 can be formed of a silicone contact layer 354 and can include a wicking material 358. In some embodiments, the bandage 350 can comprise a foam dressing. The bandage 350 can include several slits or cut-outs that form a plurality of flaps 310. For example, the bandage 350 can include flaps 310 similar to the flaps discussed above with reference to the attachment interfaces 306 of FIGS. 3-6. In some embodiments, the bandage 350 includes an inner layer configured to directly contact the receptacle 304. The inner layer can include a wicking material and/or a tacky material, such as a silicone contact layer. The bandage 350 can include an outer layer exposed to the outside environment and configured to come into contact with the subject's body. The outer layer can include a fluid impermeable layer. A middle layer can be disposed between the inner layer and the outer layer. The inner layer can include spun plastic.

Figure 8:
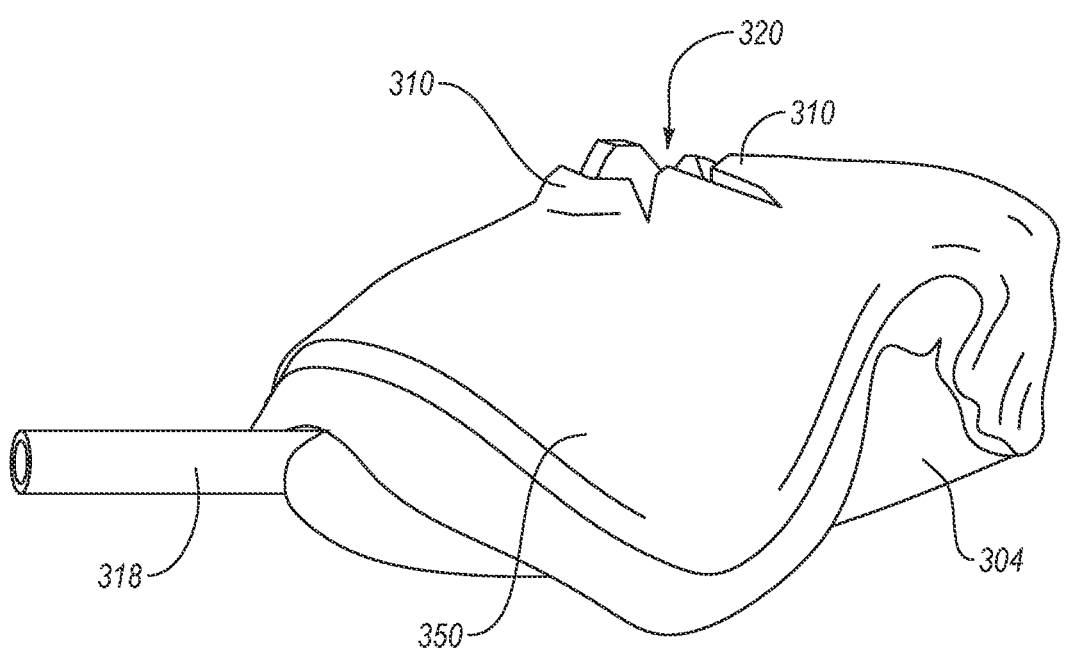
FIG. 8 is an isometric view of the bandage of FIG. 5 coupled to a urine collection device, according to an embodiment.

FIG. 8 illustrates the bandage 350 coupled to a receptacle 304 of a urine collection device, according to an embodiment. In some embodiments, the bandage 350 can include a sticky or tacky material, such as a silicone contact layer 354. For example, a major surface of the bandage 350 can include a tacky material that is capable of adhering to the receptacle 304. A second major surface of the bandage, opposite, the sticky side of the bandage 350 can include a soft material, such as polyurethane foam, intended to be comfortable against the subject's skin. In some embodiments, the bandage 350 does not use an adhesive to attach to the receptacle 304. In some embodiments, an adhesive is used to couple the bandage 350 to the receptacle 304. The hole 320 in the bandage 350 can be positioned adjacent a hole (not shown in FIG. 8) in the receptacle 304, such that the opening 320 is aligned with and in fluid communication with the interior of the receptacle 304 and further in fluid communication with the vacuum tube 318.

In some embodiments, the bandage 350 is coupled to a urine collection device, such as the urine collection devices of FIGS. 1-3. In this manner, a urine collection device could include multiple layers of flaps. For example, a first layer of flaps could be present on a wall of the receptacle 304 and a second layer of flaps could be present on the bandage 350. The layers of flaps can be oriented relative to each other such that the flaps 310 are in line with one another, or the layers can be off-set such that the flaps 310 of the bandage 350 are rotationally off-set from the flaps of the receptacle. In some embodiments, the flaps of each layer are different in shape and/or size. In some embodiments, the bandage 350 include multiple layers of flaps 310.

Figure 9:
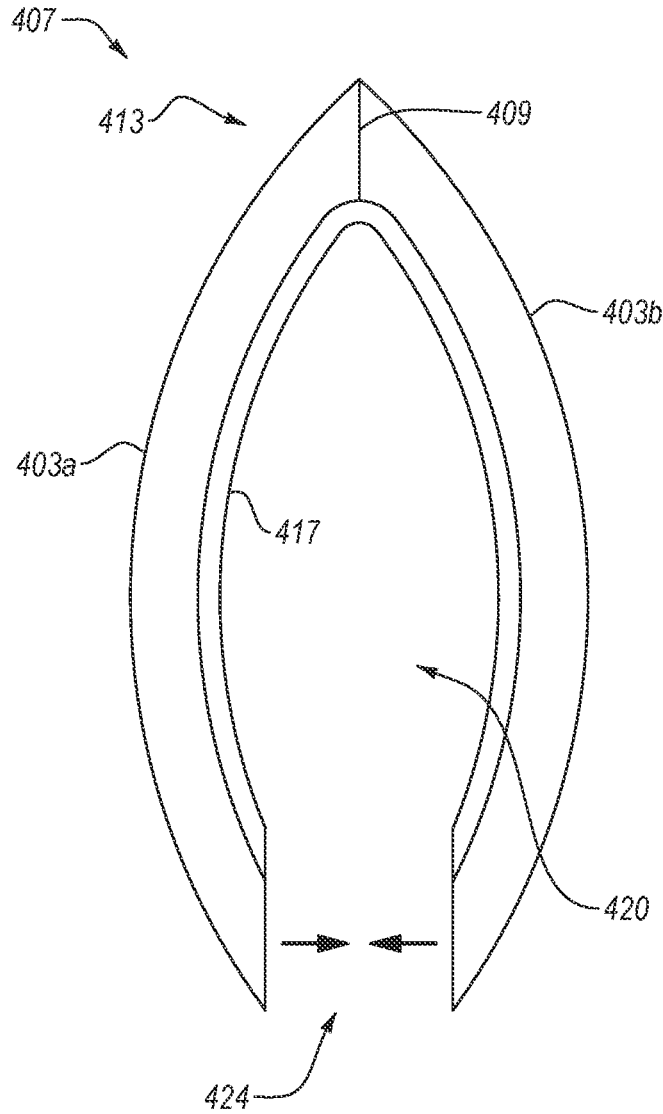
FIG. 9 is a top view of an attachment interface, according to an embodiment.

FIG. 9 illustrates an attachment mechanism or attachment interface 407 for attaching a urine collection device to a subject's penis, according to an embodiment. The attachment interface 407 is referred to herein as a clamshell, however, it will be understood that this term does not necessarily assign any properties, characteristics, or limitations onto the attachment mechanism 407. The clamshell 407 can include a first half 403*a* and a second half 403*b*. The first half 403*a* can be substantially similar or identical to the second half 403*b*, such that the clamshell 407 is symmetrical about an axis. The first half 403*a* can be connected to the second half 403*b* via a pivot point 409 at a distal end 413 of the clamshell 407. The pivot point 409 can include a hinge, joint, axle, pin, spring or any other mechanism capable of allowing relative motion between the first half 403*a* and the second half 403*b*. In some embodiments, the clamshell 407 is flexible such that the first half 403*a* and the second half 403*b* can be bent toward or away from one another. The clamshell 407 can be biased toward a closed position (i.e., where the first half 403*a* and second half 403*b* are closest at a proximal end of the clamshell 407).

In some embodiments, the clamshell 407 can include a vacuum tube and wicking layers such as those discussed above with reference to the urine collection device 280 of FIGS. 3A and 3B. For example, the clamshell 407 can include a layer, of wicking material, such as a matrix of spun plastic that at least partially surrounding a vacuum tube to collect and transport urine. The clamshell 407 can further be in fluid communication with an outlet tube attached to a sump of the clamshell 407. In some embodiments, the clamshell 407 can include a securing feature (not shown in FIG. 9) configured to secure the proximal end of the first half 403*a* to the proximal end of the second half 403*b*. In other words, the securing feature can be configured to secure the clamshell in the closed position. The securing feature can include Velcro, an adhesive, or a strip, such as the strip 500 discussed below with reference to FIGS. 12A-13.

In operation, the clamshell 407 can be position around a penis, with the penis positioned between the first half 403*a* and the second half 403*b* in the opening 420. When in the closed position, the clamshell 407 can be frictionally secured to the penis. In some embodiments, the clamshell 407 can be configured to secure a base of the urine collection device to the base of the penis. The clamshell 407 can be configured to clamp, constrict, or squeeze the penis sufficient to secure the clamshell 407 to the penis, while still allowing urine flow. In some examples, the clamshell 407 can include different levels of constriction or clamping. For example, the degree of clamping or the pressure applied onto the penis can be increased to improve the fit or attachment onto the penis. The clamshell 407 can include an inner layer 417 that is tacky or sticky to enhance the friction securement between the clamshell 407 and the penis. In some embodiments, the inner layer 417 includes a rugged surface with enhanced friction. For example, the inner layer 417 can include spun plastic. In an embodiment, the inner layer 417 includes flaps similar to the flaps 310.

Figure 10:
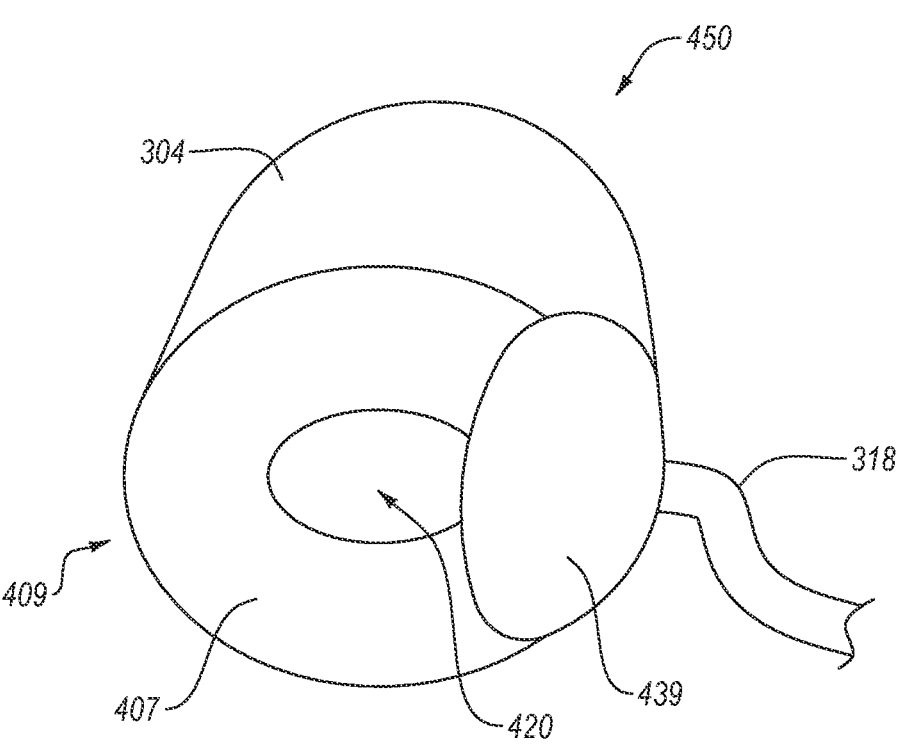
FIG. 10 is a bottom isometric view of a urine collection device, according to an embodiment.

FIG. 10 illustrates a clamshell 407 functionally coupled with the receptacle 304 of a urine collection device 450, according to an embodiment. The urine collection device 450 can be substantially similar to the urine collection device 300 discussed above with reference to FIG. 4A. For example, the urine collection device 450 can include a receptacle 304 in fluid communication with a vacuum tube 318. The clamshell 407 can be integrally formed with the receptacle 304 or can be a separate and distinct piece configured to attach and form a seal with the receptacle 304.

The urine collection device 450 can include a sump 439 configured to collect urine to be suctioned from the receptacle 304. In some embodiments, the sump 439 is coupled to the clamshell 407.

Figure 11:
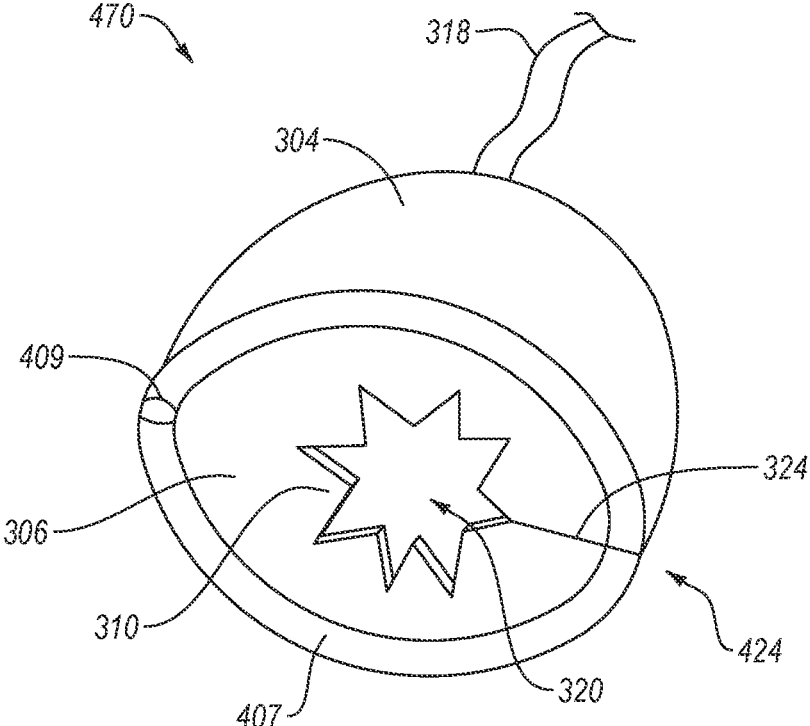
FIG. 11 is a bottom isometric view of a urine collection device having both the attachment interfaces of FIGS. 4B and 7, according to an embodiment.

FIG. 11 illustrates a urine collection device 470 including an attachment interface 306 and a clamshell 407 operationally coupled to the receptacle 304, according to an embodiment. The attachment interface 306 and clamshell 407 can be substantially similar to the attachment interfaces and clamshells discussed herein. In some embodiments, the flaps 310 of the attachment interface 306 can extend from a perimeter of the clamshell 407. The flaps 310 can be integrally formed from the inner sidewall of the clamshell 407. A gap 324 in the attachment interface 306 can coincide with the gap 424 in the clamshell 407. In this manner, the features and improvements of the attachment interfaces can be combined with the features and improvements of the clamshell 407 to produce enhanced attachment methodologies of the urine collection device. The gaps 324 and 424 in the urine collection device 470 could be closed and secured using any securement method, such as Velcro, adhesive, knots, or the strips disclosed herein.

Figure 12A:
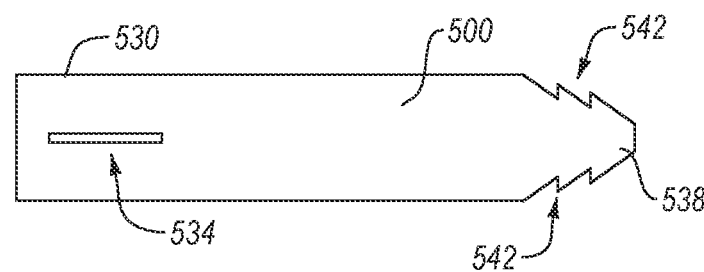
FIG. 12A is a side view of a securement feature, according to an embodiment.

FIG. 12A illustrates a strip 500, according to an embodiment. The strip 500 can be considered an attachment interface and can be used as a closing, tightening, or constricting device. For example, the strip 500 can be used in conjunction with the attachment interfaces discussed herein to further aid is securing the urine collection device to the penis. In some embodiments, the strip 500 can be used to wrap directly around the penis and can, in some cases, be used to constrict the penis to restrict urine flow. The strip 500 can be formed from a piece of coarse spun plastic. The strip 500 can include a tip 538 formed on a first end of the strip 500 and a slot 534 formed on a second end of the strip 500, opposite the first end. The tip 538 can include one or more catches or jagged section 542 configured to pass through the slot 534 in one direction and catch or snag on the slot 534 in a second direction. In this manner, the strip 500 can be a pull-through strap configured to secure to itself via friction.

Figure 12B:
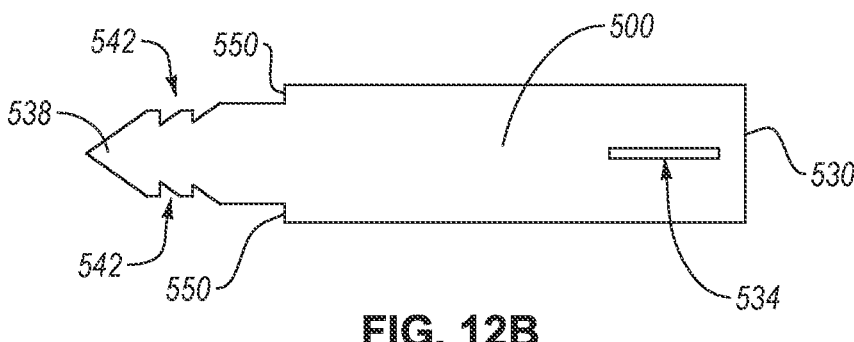
FIG. 12B is a side view of a securement feature, according to an embodiment.
Figure 12C:
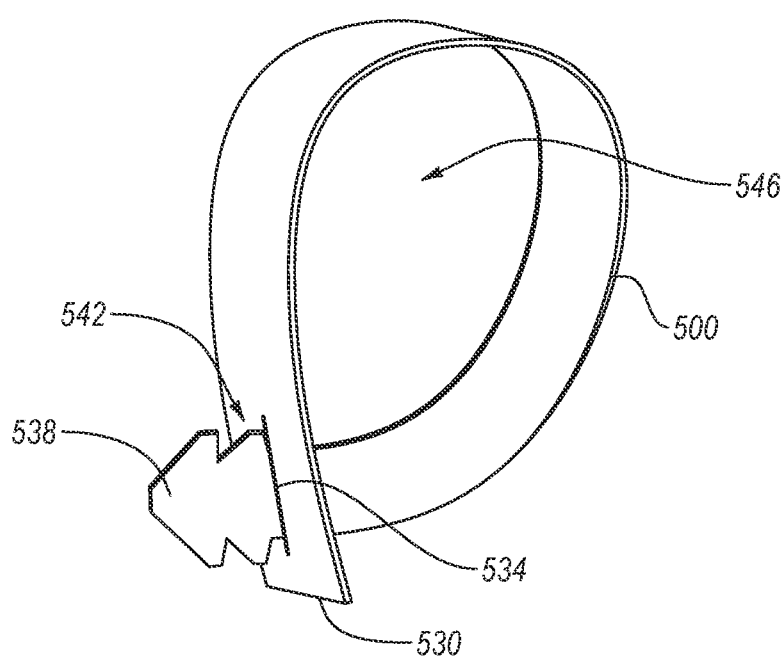
FIG. 12C is an isometric view of the securement feature of FIG. 11B in an engaged state, according to an embodiment.

FIG. 12B illustrates the strip 500 including a shelf or stop 550 configured to prevent the tip 538 from entering any further into the slot 534. FIG. 12C illustrates the strip 500 with the tip 538 engaged in the slot 534. As illustrated, when the tip 538 is fed through the slot 534, the strip 500 forms a loop or noose 546. In some embodiments, the loop formed by the strip 500 can act as an attachment or securement mechanism. The catches 542 can help prevent the tip 538 from backing out of the slot 534, and the shelf 550 can prevent the strip 500 from being pulled too tight. In some embodiments, the strip 500 is formed of a coarse material. The course nature of the strip 500 can aid the tip 538 from slipping out of the slot 534. The coarseness of the strip 500 can also help keep the strip 500 in place against the user's skin and thereby reducing abrasive forces against the user's skin. The strip 500 can be used in conjunction with any of the attachment interfaces or clamshell devices disclosed herein. For example, the strip 500 can be used to close or tighten the gap 324 of the attachment interface 306 and the gap 424 of the clamshell 407.

Figure 13:
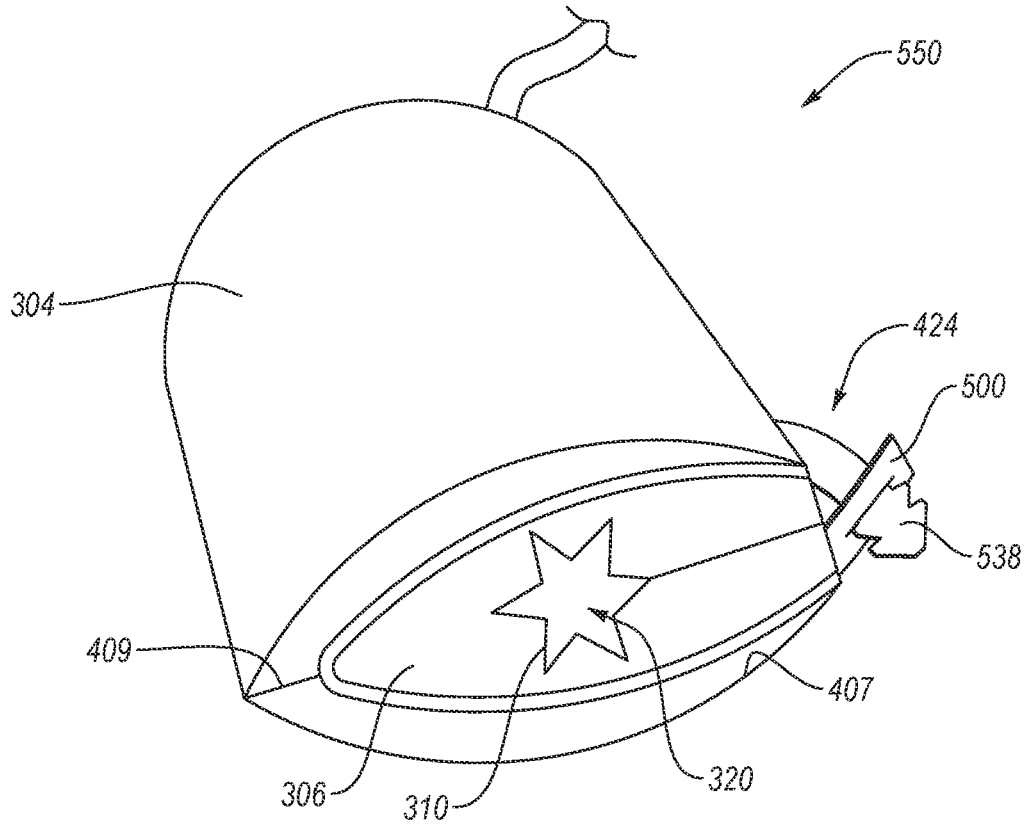
FIG. 13 is a bottom isometric view of a urine collection device having the attachment interfaces of FIGS. 4B and 7 and the securement feature of FIG. 11B, according to an embodiment.

FIG. 13 is a bottom isometric view of a urine collection device 550 having multiple attachment features as described herein, according to an embodiment. The urine collection device 550 of FIG. 13 can include an attachment interface 306 and clamshell 407 for removably securing the urine collection device to the penis. Further, a strip 500, similar to the strips disclosed herein, can be positioned on either ends of the attachment interface 306 and/or the clamshell 407 such that the clamshell 407 and the attachment interface 306 can be closed around the penis when the strip 500 is pulled through itself, thereby closing the gap 424. The strip 500 can be integrally formed with either of the clamshell 407 or attachment interface 306, such that cinching the strip 500 also causes the clamshell 407 or attachment interface 306 to tighten around the penis. In an embodiment, the strip 500 is positioned along an inner circumference of the receptacle 304. In an embodiment, the strip 500 wraps around the circumference of the receptacle 304. Thus, it will be understood that each of the attachment interfaces described herein (e.g., attachment interface 306, clamshell 407, and strip 500) can be used individually or in combination to improve attachment of the urine collection device to the penis.

Figure 14:
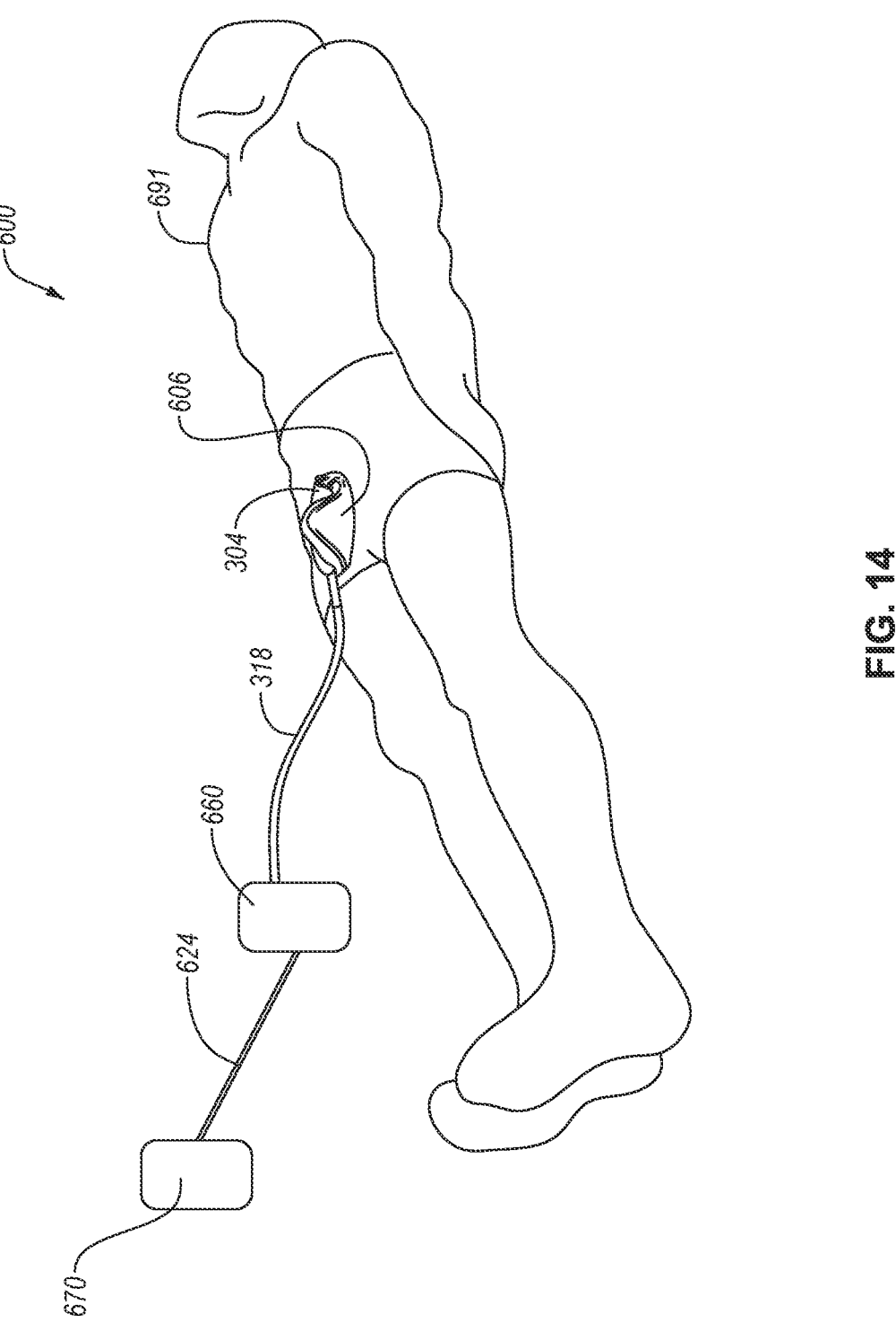
FIG. 14 is a schematic illustration of a urine collection device disposed on the body of a user, according to an embodiment.

FIG. 14 is a schematic illustration of a urine collecting system 600 disposed on the body of a subject 691, according to an embodiment. The urine collecting system 600 can utilize any of the urine collection devices and attachment interfaces disclosed herein. The urine collecting system 600 can include a receptacle 304 to collect urine and an attachment interface 606. The attachment interface 606 can be the same or similar in structure and/or function to any of the attachment interfaces described herein, such as attachment interfaces 106, 306, 350, 407, 500, and any combination thereof. The urine collecting system 600 can include an external receptacle 660 and a vacuum source 670. The external receptacle 660 can be a temporary storage location for urine drawn from the receptacle 304. In an embodiment, the vacuum source 670 can assist and/or provide the pressure differential needed to draw fluid voided from the urethral opening of a user into the receptacle 104, and from the receptacle 304 into the external receptacle 660. The vacuum source 670 can be fluidly coupled to the external receptacle 660 via a vacuum line 624 such that urine is drawn from the external receptacle 660 via the vacuum line 624. As a result of the decrease in pressure within the external receptacle 660 caused by the drawing of fluid out of the external receptacle 660, liquid and/or gaseous fluid can be drawn from the receptacle 304, through the tube 318, and into the external receptacle 660. In an embodiment, the vacuum source 670 can apply sufficient suction to capture all or substantially all of the urine voided by a user in a variety of positions (e.g., when a user is lying on his side).

In an embodiment, the vacuum source 670 can be a pump that is readily available, inexpensive, relatively quiet, and/or configured to run continuously. For example, the vacuum source 670 can be a pump. In an embodiment, the vacuum source 670 can be powered by electrical AC or DC power. For example, in mobile applications when the user is away from an AC power source, such as when the user is using the urine collecting system 600 during transportation via a wheel chair or motor vehicle, the vacuum source 670 can be powered by DC power. One suitable non-limiting example of a pump that can be used is the DryDoc Vacuum Station, available from PureWick, Inc.

In use, as shown in FIG. 14, the urine collecting system 600 can be positioned such that the attachment interface 606 encloses a portion of the penis of the subject 491. For example, the attachment interface 606 can be positioned such that the urethral opening of the user 691 is within an internal volume of the receptacle 304.

While various embodiments of the urine collecting system, methods and devices have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and such modifications are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

For example, although various embodiments have been described as having particular features and/or combinations of components, other embodiments are possible having any combination or sub-combination of any features and/or components from any of the embodiments described herein. In addition, the specific configurations of the various components can also be varied. For example, the size and specific shape of the various components can be different than the embodiments shown, while still providing the functions as described herein.

The invention claimed is:

1. A male urine collection device for collection of urine discharged from a subject, the male urine collection device comprising:

a receptacle defining an internal volume, the receptacle configured to receive a penis and to collect urine;

an attachment interface including two attachment interface terminating ends and a plurality of flaps movable to access the internal volume of the receptacle, the attachment interface being shaped such that the two attachment interface terminating ends are positioned or positionable at least proximate to one another at a discontinuous region of the attachment interface and the attachment interface extends continuously between the two attachment interface terminating ends, the plurality of flaps configured to bias against the penis when the penis is at least partially received by the receptacle; and a clamshell having two halves movable with respect to each other via a hinge, the clamshell configured to close around the penis to secure the receptacle about the penis when the penis is at least partially received by the receptacle;

wherein the clamshell includes the plurality of flaps extending from a perimeter of the clamshell and two clamshell terminating ends substantially aligned with discontinuous region and the two attachment interface terminating ends of the attachment interface, and wherein each half of the two halves of the clamshell includes an end region positioned generally opposite to the hinge, the end region of the two halves being spaced from one another with the attachment interface positioned between the end regions of the two halves.

2. The male urine collection device of claim 1, wherein the plurality of flaps at least partially define an opening into the receptacle.

3. The male urine collection device of claim 1, wherein the plurality of flaps are configured to bend into the internal volume of the receptacle when the penis is received.

4. The male urine collection device of claim 1, wherein the plurality of flaps are positioned on a contact layer that is coupled to the receptacle.

5. The male urine collection device of claim 1, wherein the receptacle includes a wicking material therein.

6. The male urine collection device of claim 1, wherein the plurality of flaps include three or more flaps.

7. The male urine collection device of claim 1, wherein the plurality of flaps define a first layer of flaps that are offset from a second layer of flaps.

8. The male urine collection device of claim 1, wherein the plurality of flaps are configured to constrict around the penis, when the penis is at least partially received by the receptacle, to removably secure to the flaps to the penis by elastic tension in the plurality of flaps.

9. The male urine collection device of claim 1, wherein the attachment interface defines a first gap between the two attachment interface terminating ends of the attachment interface and the clamshell defines a second gap between the two clamshell terminating ends of the clamshell and coinciding with the first gap, the first gap and the second gap configured to allow the clamshell to receive the penis.

10. The male urine collection device of claim 1, wherein the receptacle includes a sump that is configured to be in fluid communication with a vacuum.

11. The male urine collection device of claim 1, wherein the plurality of flaps form a tacky, non-adhesive interface with the penis.

12. The male urine collection device of claim 1, further comprising a pull-through strip configured to secure the receptacle around the penis via friction.

13. A male urine collection device for collection of urine discharged from a penis, the male urine collection device comprising:

a receptacle defining an internal volume, the receptacle configured to collect urine;

an attachment interface including two attachment interface terminating ends and a plurality of flaps movable to access the internal volume of the receptacle, the attachment interface being shaped such that the two attachment interface terminating ends are positioned or positionable at least proximate to one another at a discontinuous region of the attachment interface and the attachment interface extends continuously between the two attachment interface terminating ends, the plurality of flaps configured to bias against the penis when the penis is at least partially received by the receptacle;

and a clamshell having two halves movable with respect to each other via a hinge, the clamshell configured to close around the penis to secure the receptacle about the penis when the penis is at least partially received by the receptacle; and a pull-through strip including a first portion extending from a first half of the two halves of clamshell and a second portion extending from a second half of the two halves of the clamshell and configured to pull through the first portion to close a gap of the clamshell around the penis and/or tighten the clamshell around the penis, wherein the pull-through strip is sized and dimensioned to selectively constrict the penis to restrict urine flow from the penis;

wherein the clamshell is removably secured to the penis via friction, and wherein each half of the two halves of the clamshell includes an end region positioned generally opposite to the hinge, the end region of the two halves being spaced from one another with the attachment interface positioned between the end regions of the two halves.

14. The male urine collection device of 13, wherein the clamshell forms a tacky, non-adhesive interface with the penis.

15. The male urine collection device of claim 13, wherein the hinge is biased to keep the two halves of the clamshell together in a closed position.

16. The male urine collection device of claim 13, wherein the clamshell includes a closing mechanism to secure the two halves in a closed position.

17. The male urine collection device of claim 16, wherein the closing mechanism includes at least one of an adhesive, Velcro, or a knot.

\* \* \* \* \*